(12) United States Patent
Fasan

(10) Patent No.: US 10,294,273 B2
(45) Date of Patent: May 21, 2019

(54) MACROCYCLIC PEPTIDOMIMETICS FOR ALPHA-HELIX MIMICRY

(71) Applicant: UNIVERSITY OF ROCHESTER, Rochester, NY (US)

(72) Inventor: Rudi Fasan, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 15/301,084

(22) PCT Filed: Apr. 1, 2015

(86) PCT No.: PCT/US2015/023883
§ 371 (c)(1),
(2) Date: Sep. 30, 2016

(87) PCT Pub. No.: WO2015/153761
PCT Pub. Date: Oct. 8, 2015

(65) Prior Publication Data
US 2017/0037084 A1    Feb. 9, 2017

Related U.S. Application Data

(60) Provisional application No. 61/973,994, filed on Apr. 2, 2014.

(51) Int. Cl.
| | |
|---|---|
| *C07K 7/06* | (2006.01) |
| *C07K 7/08* | (2006.01) |
| *C07K 7/54* | (2006.01) |
| *A61K 38/00* | (2006.01) |
| *A61K 38/12* | (2006.01) |
| *C07K 14/00* | (2006.01) |

(52) U.S. Cl.
CPC .............. *C07K 7/54* (2013.01); *C07K 7/06* (2013.01); *C07K 7/08* (2013.01); *C07K 14/001* (2013.01); *A61K 38/00* (2013.01); *A61K 38/12* (2013.01)

(58) Field of Classification Search
CPC ...... A61K 38/00; A61K 38/12; C07K 14/001; C07K 7/06; C07K 7/08; C07K 7/54
See application file for complete search history.

(56) References Cited

U.S. PATENT DOCUMENTS

| | | |
|---|---|---|
| 7,083,983 B2 | 8/2006 | Lane et al. |
| 8,343,760 B2 | 1/2013 | Lu et al. |
| 2013/0330773 A1 | 12/2013 | Fasan et al. |
| 2014/0057857 A1 | 2/2014 | Lin et al. |

FOREIGN PATENT DOCUMENTS

| | | |
|---|---|---|
| JP | 2013535514 A | 9/2013 |
| WO | WO-2005/090388 A1 | 9/2005 |

OTHER PUBLICATIONS

Frost, John R., et al., "Macrocyclization of Organo-Peptide Hybrids through a Dual bio-orthogonal Ligation; Insights from Structure-Reactivity Studies", Chembiochem, vol. 14, No. 1, Nov. 30, 2012 (pp. 147-160).
Satyanarayana, Maragani, et al., "Diverse organo-peptide macrocycles via a fast and catalyst-free oxime/intein-mediated dual ligation", Chemical Communications, vol. 48, No. 10, Sep. 7, 2011 (pp. 1461-1463).
Smith, Jessica M., et al., "Modular assembly of macrocyclic organo-peptide hybrids using synthetic and genetically encoded precursors", Angewandte Chemie International Edition, Verlag Chemie, vol. 50, No. 22, May 23, 2011, (pp. 5075-5080).
European Patent Office, Extended European Search Report, corresponding European Application No. 15773413.8, dated Jan. 3, 2018 (9 pages).
Frost, et al., "Design, synthesis, and diversification of ribosomally derived peptide macrocycles," Aug. 2013, Current Opinion in Structural Biology, vol. 23, Issue 4 (pp. 571-580). Available online Jul. 12, 2013.
Smith, et al., "Designer macrocyclic organo-peptide hybrids inhibit the interaction between p53 and HDM2/X by accommodating a functional α-helix", 2014, Chemical Communications, vol. 50, (pp. 5027-5030 and S1-S11).
Smith, J., et al., "Emerging Strategies to Access Peptide Macrocycles from Genetically Encoded Polypeptides", The Journal of Organic Chemistry, vol. 78, No. 8, (2013-03-21) pp. 3525-3531.
ISA/US, International Search Report, for corresponding International Application No. PCT/US2015/023883, dated Oct. 1, 2015 (23 pages).
Pazgier, Marzena, et al., "Structural basis for high-affinity peptide inhibition of p53 interactions with MDM2 and MDMX", PNAS, 2009, vol. 106, No. 12, p. 4665-4670.
Office Action for corresponding Japanese Patent Application No. 2016-560695 dated Feb. 19, 2019.

*Primary Examiner* — Marcela M Cordero Garcia
(74) *Attorney, Agent, or Firm* — Harris Beach PLLC

(57) ABSTRACT

Methods and compositions are provided for generating macrocyclic peptides constrained by side-chain-to-C-terminus non-peptidic tethers for use as functional and structural mimics of α-helical motifs, including in therapeutic applications. These methods can be used to produce libraries of conformationally constrained peptidomimetics to identify compounds with desired activity properties.

Figure 1:
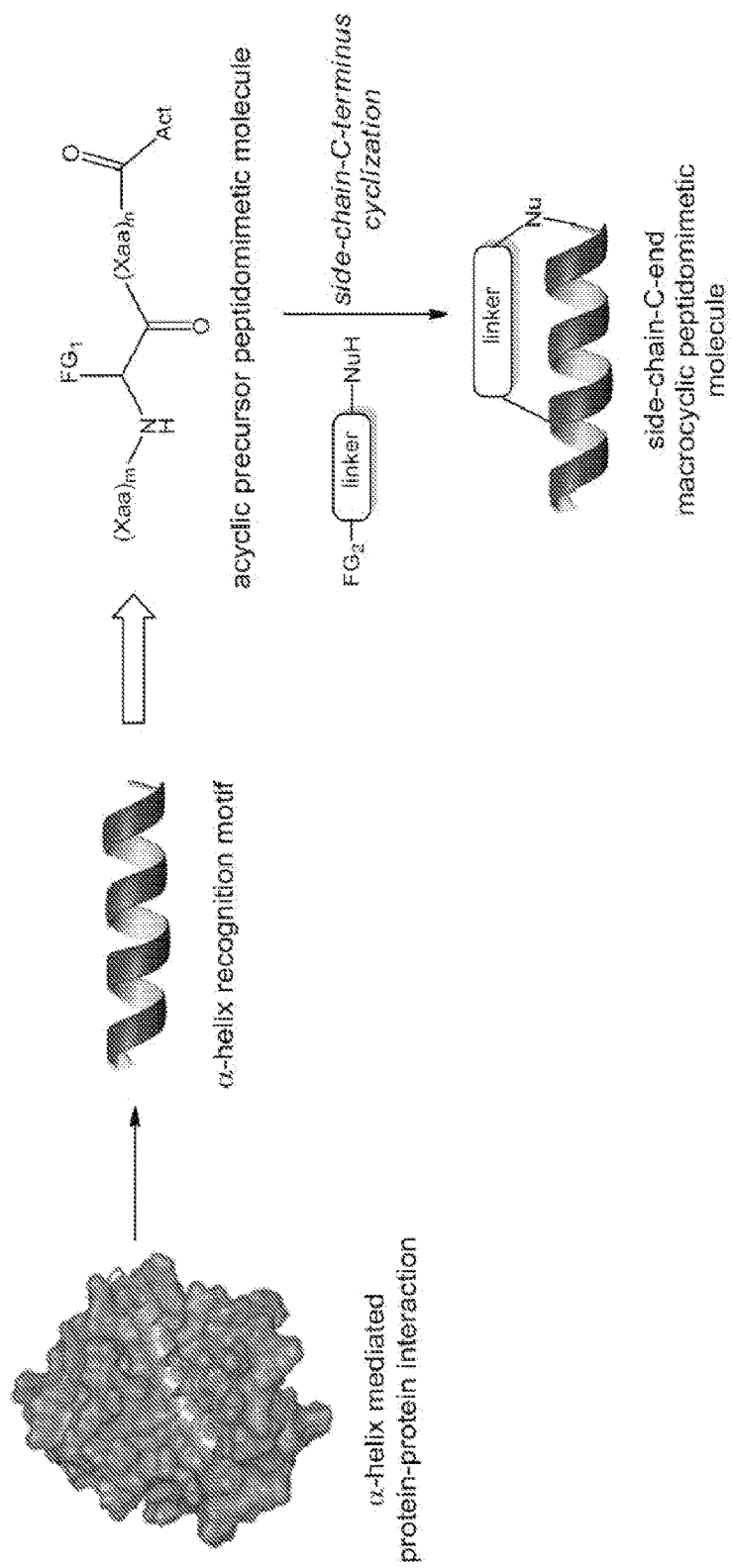

34 Claims, 21 Drawing Sheets
Specification includes a Sequence Listing.

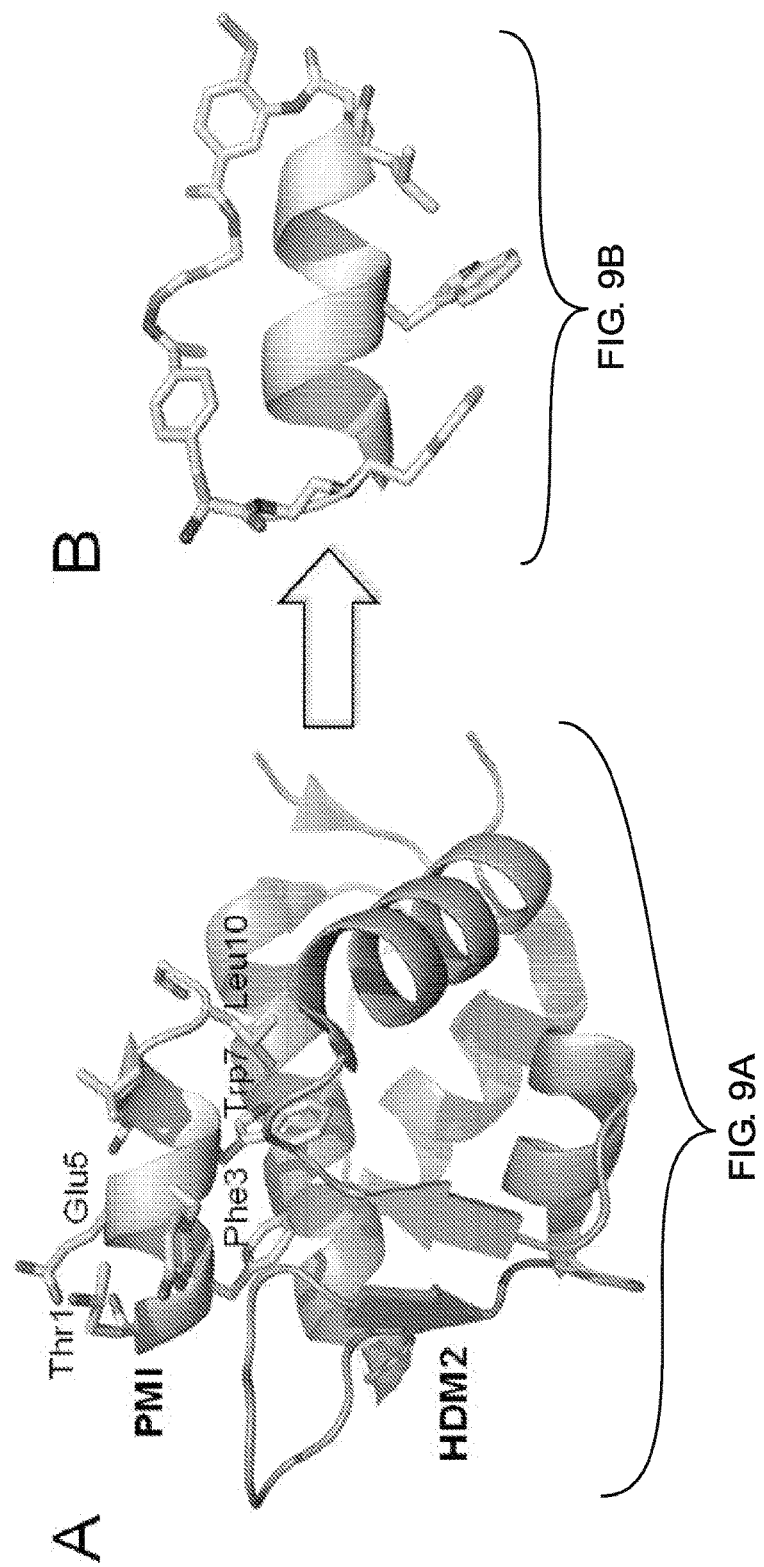

| Name | SEQ ID NO: | Sequence | linkage | HDM2 IC$_{50}$ (nM) | HDMX IC$_{50}$ (nM) |
|---|---|---|---|---|---|
| P1 | 1 | H-SQETFSDLWKLLPEN-NH$_2$ | linear | 920 | 1,200 |
| P2 | 43 | Ac-GTSFAYYWNLLA-NH$_2$ | linear | 1,510 | 7,500 |
| P3 | 38 | H-GTSFA(pAcF)YWNLLA  [SP6] | i/i+6(CO) | 870 | 4,100 |
| P4 | 38 | H-GTSFA-pAcF)YWNLLA  [SP8] | i/i+6(CO) | 1,500 | 3,500 |
| P5 | 38 | H-GTSFA-pAcF)YWNLLA  [SP4] | i/i+6(CO) | 10,000 | ND |
| P6 | 44 | Ac-GYSFAEYWNLLA-NH$_2$ | linear | 65 | 355 |
| P7 | 39 | H-G(pAcF)SFAEYWNLLA  [SP6] | i/i+10(CO) | 475 | 910 |
| P8 | 39 | H-G(pAcF)SFAEYWNLLA  [SP8] | i/i+10(CO) | 110 | 340 |
| P9 | 39 | H-G(pAcF)SFAEYWNLLA  [SP4] | i/i+10(CO) | > 50,000 | > 50,000 |
| P10 | 12 | Ac-(pAcF)SFAEYWNLLA-NH$_2$ | linear | 110 | |
| P11 | 12 | Ac-(pAcF)SFAEY(6ClW)ALLA-NH$_2$ | linear | 30 | |
| P12 | 39 | Ac-G(pAcF)SFAEYWNLLA  [SP8] | i/i+10(CO) | 145 | |
| P13 | 12 | Ac-(pAcF)SFAEYWNLLA  [SP8] | i/i+10(CO) | 135 | |
| P14 | 12 | Ac-(mAcF)SFAEYWNLLA  [SP8] | i/i+10(CO) | 255 | |
| P15 | 12 | Ac-(pAcF)SFAEY(6ClW)ALLA  [SP8] | i/i+10(CO) | 50 | |
| P16 | 12 | Ac-(mAcF)SFAEY(6ClW)ALLA  [SP8] | i/i+10(CO) | 105 | |
| P17 | 12 | Ac-(pAcF)SFAEY(6ClW)ALLA  [SP9] | i/i+10(CO) | 305 | |
| P18 | 12 | Ac-(mAcF)SFAEY(6ClW)ALLA  [SP9] | i/i+10(CO) | 400 | |
| P19 | 12 | Ac-(pAcF)SFAEY(6ClW)ALLA  [SP4] | > i/i+10(CO) | >50,000 | |

FIG. 10

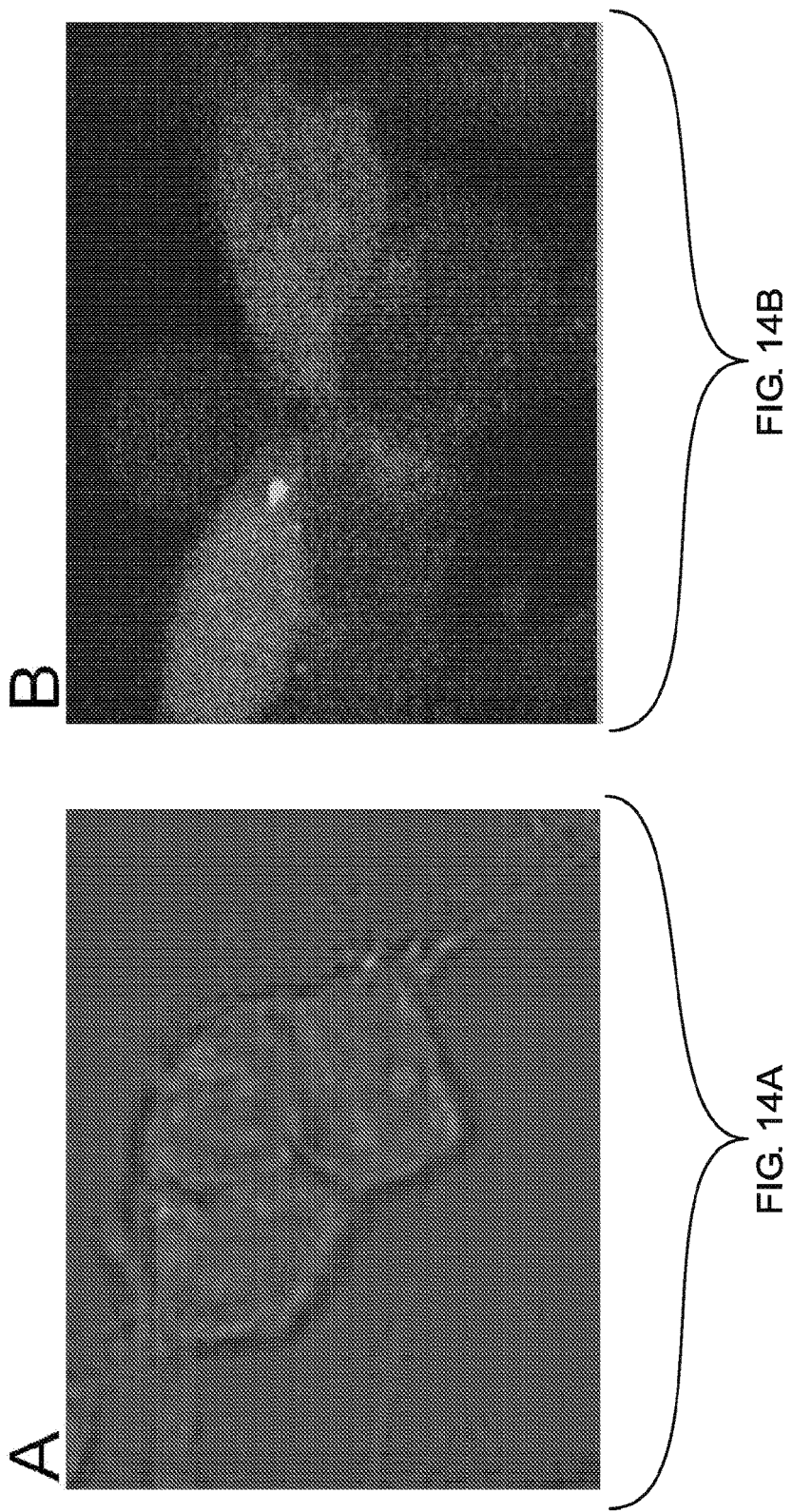

SEQUENCE LISTING

<160> NUMBER OF SEQ ID NOS: 44

<210> SEQ ID NO 1
<211> LENGTH: 15
<212> TYPE: PRT
<213> ORGANISM: Artificial Sequence
<220> FEATURE:
<223> OTHER INFORMATION: Engineered sequence

<400> SEQUENCE: 1

Ser Gln Glu Thr Phe Ser Asp Leu Trp Lys Leu Leu Pro Glu Asn
1               5                   10                  15

<210> SEQ ID NO 2
<211> LENGTH: 12
<212> TYPE: PRT
<213> ORGANISM: Artificial Sequence
<220> FEATURE:
<223> OTHER INFORMATION: Engineered sequence

<400> SEQUENCE: 2

Thr Ser Phe Ala Glu Tyr Trp Asn Leu Leu Ser Pro
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Engineered sequence

<400> SEQUENCE: 3

Leu Thr Phe Glu His Tyr Trp Ala Gln Leu Thr Ser
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Engineered sequence
<220> FEATURE:
<221> NAME/KEY: VARIANT
<222> LOCATION: (1)..(1)
<223> OTHER INFORMATION: G or para-acetyl-phenylalanine (pAcF)
<220> FEATURE:
<221> NAME/KEY: MISC_FEATURE
<222> LOCATION: (1)..(13)
<223> OTHER INFORMATION: Amino acid linked to carboxy terminus via
      macrocycle-forming linker
<220> FEATURE:
<221> NAME/KEY: VARIANT
<222> LOCATION: (8)..(8)
<223> OTHER INFORMATION: L or Y
<220> FEATURE:
<221> NAME/KEY: VARIANT
<222> LOCATION: (9)..(9)
<223> OTHER INFORMATION: W or 6-chloro-tryptophan (6Cl-W)
<220> FEATURE:
<221> NAME/KEY: VARIANT
<222> LOCATION: (13)..(13)
<223> OTHER INFORMATION: P or A

<400> SEQUENCE: 4

Xaa Ser Gln Thr Phe Ser Asn Xaa Xaa Arg Leu Leu Xaa
1               5                   10

<210> SEQ ID NO 5
<211> LENGTH: 13
<212> TYPE: PRT

```
<213> ORGANISM: Artificial Sequence
<220> FEATURE:
<223> OTHER INFORMATION: engineered sequence
<220> FEATURE:
<221> NAME/KEY: VARIANT
<222> LOCATION: (2)..(2)
<223> OTHER INFORMATION: G or para-acetyl-phenylalanine (pAcF)
<220> FEATURE:
<221> NAME/KEY: MISC_FEATURE
<222> LOCATION: (2)..(13)
<223> OTHER INFORMATION: Amino acid linked to carboxy terminus via
      macrocycle-forming linker
<220> FEATURE:
<221> NAME/KEY: VARIANT
<222> LOCATION: (8)..(8)
<223> OTHER INFORMATION: L or Y
<220> FEATURE:
<221> NAME/KEY: VARIANT
<222> LOCATION: (9)..(9)
<223> OTHER INFORMATION: W or 6-chloro-tryptophan (6Cl-W)
<220> FEATURE:
<221> NAME/KEY: VARIANT
<222> LOCATION: (13)..(13)
<223> OTHER INFORMATION: P or A

<400> SEQUENCE: 5

Gln Xaa Gln Thr Phe Ser Asn Xaa Xaa Arg Leu Leu Xaa
1               5                   10

<210> SEQ ID NO 6
<211> LENGTH: 13
<212> TYPE: PRT
<213> ORGANISM: Artificial Sequence
<220> FEATURE:
<223> OTHER INFORMATION: engineered sequence
<220> FEATURE:
<221> NAME/KEY: VARIANT
<222> LOCATION: (3)..(3)
<223> OTHER INFORMATION: G or para-acetyl-phenylalanine (pAcF)
<220> FEATURE:
<221> NAME/KEY: MISC_FEATURE
<222> LOCATION: (3)..(13)
<223> OTHER INFORMATION: Amino acid linked to carboxy terminus via
      macrocycle-forming linker
<220> FEATURE:
<221> NAME/KEY: VARIANT
<222> LOCATION: (8)..(8)
<223> OTHER INFORMATION: L or Y
<220> FEATURE:
<221> NAME/KEY: VARIANT
<222> LOCATION: (9)..(9)
<223> OTHER INFORMATION: W or 6-chloro-tryptophan (6Cl-W)
<220> FEATURE:
<221> NAME/KEY: VARIANT
<222> LOCATION: (13)..(13)
<223> OTHER INFORMATION: P or A

<400> SEQUENCE: 6

Gln Ser Xaa Thr Phe Ser Asn Xaa Xaa Arg Leu Leu Xaa
1               5                   10

<210> SEQ ID NO 7
<211> LENGTH: 13
<212> TYPE: PRT
<213> ORGANISM: Artificial Sequence
<220> FEATURE:
<223> OTHER INFORMATION: engineered sequence
<220> FEATURE:
<221> NAME/KEY: VARIANT
<222> LOCATION: (4)..(4)
<223> OTHER INFORMATION: G or para-acetyl-phenylalanine (pAcF)
<220> FEATURE:
<221> NAME/KEY: MISC_FEATURE
<222> LOCATION: (4)..(13)
<223> OTHER INFORMATION: Amino acid linked to carboxy terminus via
```

```
        macrocycle-forming linker
<220> FEATURE:
<221> NAME/KEY: VARIANT
<222> LOCATION: (8)..(8)
<223> OTHER INFORMATION: L or Y
<220> FEATURE:
<221> NAME/KEY: VARIANT
<222> LOCATION: (9)..(9)
<223> OTHER INFORMATION: W or 6-chloro-tryptophan (6Cl-W)
<220> FEATURE:
<221> NAME/KEY: VARIANT
<222> LOCATION: (13)..(13)
<223> OTHER INFORMATION: P or A

<400> SEQUENCE: 7

Gln Ser Gln Xaa Phe Ser Asn Xaa Xaa Arg Leu Leu Xaa
1               5                   10

<210> SEQ ID NO 8
<211> LENGTH: 13
<212> TYPE: PRT
<213> ORGANISM: Artificial Sequence
<220> FEATURE:
<223> OTHER INFORMATION: engineered sequence
<220> FEATURE:
<221> NAME/KEY: VARIANT
<222> LOCATION: (6)..(6)
<223> OTHER INFORMATION: G or para-acetyl-phenylalanine (pAcF)
<220> FEATURE:
<221> NAME/KEY: MISC_FEATURE
<222> LOCATION: (6)..(13)
<223> OTHER INFORMATION: Amino acid linked to carboxy terminus via
        macrocycle-forming linker
<220> FEATURE:
<221> NAME/KEY: VARIANT
<222> LOCATION: (8)..(8)
<223> OTHER INFORMATION: L or Y
<220> FEATURE:
<221> NAME/KEY: VARIANT
<222> LOCATION: (9)..(9)
<223> OTHER INFORMATION: W or 6-chloro-tryptophan (6Cl-W)
<220> FEATURE:
<221> NAME/KEY: VARIANT
<222> LOCATION: (13)..(13)
<223> OTHER INFORMATION: P or A

<400> SEQUENCE: 8

Gln Ser Gln Thr Phe Xaa Asn Xaa Xaa Arg Leu Leu Xaa
1               5                   10

<210> SEQ ID NO 9
<211> LENGTH: 13
<212> TYPE: PRT
<213> ORGANISM: Artificial Sequence
<220> FEATURE:
<223> OTHER INFORMATION: engineered sequence
<220> FEATURE:
<221> NAME/KEY: VARIANT
<222> LOCATION: (7)..(7)
<223> OTHER INFORMATION: G or para-acetyl-phenylalanine (pAcF)
<220> FEATURE:
<221> NAME/KEY: MISC_FEATURE
<222> LOCATION: (7)..(13)
<223> OTHER INFORMATION: Amino acid linked to carboxy terminus via
        macrocycle-forming linker
<220> FEATURE:
<221> NAME/KEY: VARIANT
<222> LOCATION: (8)..(8)
<223> OTHER INFORMATION: L or Y
<220> FEATURE:
<221> NAME/KEY: VARIANT
<222> LOCATION: (9)..(9)
<223> OTHER INFORMATION: W or 6-chloro-tryptophan (6Cl-W)
<220> FEATURE:
<221> NAME/KEY: VARIANT
```

-continued

```
<222> LOCATION: (13)..(13)
<223> OTHER INFORMATION: P or A

<400> SEQUENCE: 9

Gln Ser Gln Thr Phe Ser Xaa Xaa Xaa Arg Leu Leu Xaa
1               5                   10

<210> SEQ ID NO 10
<211> LENGTH: 13
<212> TYPE: PRT
<213> ORGANISM: Artificial Sequence
<220> FEATURE:
<223> OTHER INFORMATION: engineered sequence
<220> FEATURE:
<221> NAME/KEY: VARIANT
<222> LOCATION: (8)..(8)
<223> OTHER INFORMATION: G or para-acetyl-phenylalanine (pAcF)
<220> FEATURE:
<221> NAME/KEY: MISC_FEATURE
<222> LOCATION: (8)..(13)
<223> OTHER INFORMATION: Amino acid linked to carboxy terminus via
      macrocycle-forming linker
<220> FEATURE:
<221> NAME/KEY: VARIANT
<222> LOCATION: (9)..(9)
<223> OTHER INFORMATION: W or 6-chloro-tryptophan (6Cl-W)
<220> FEATURE:
<221> NAME/KEY: VARIANT
<222> LOCATION: (13)..(13)
<223> OTHER INFORMATION: P or A

<400> SEQUENCE: 10

Gln Ser Gln Thr Phe Ser Asn Xaa Xaa Arg Leu Leu Xaa
1               5                   10

<210> SEQ ID NO 11
<211> LENGTH: 13
<212> TYPE: PRT
<213> ORGANISM: Artificial Sequence
<220> FEATURE:
<223> OTHER INFORMATION: engineered sequence
<220> FEATURE:
<221> NAME/KEY: VARIANT
<222> LOCATION: (8)..(8)
<223> OTHER INFORMATION: L or Y
<220> FEATURE:
<221> NAME/KEY: VARIANT
<222> LOCATION: (9)..(9)
<223> OTHER INFORMATION: W or 6-chloro-tryptophan (6Cl-W)
<220> FEATURE:
<221> NAME/KEY: VARIANT
<222> LOCATION: (10)..(10)
<223> OTHER INFORMATION: G or para-acetyl-phenylalanine (pAcF)
<220> FEATURE:
<221> NAME/KEY: MISC_FEATURE
<222> LOCATION: (10)..(13)
<223> OTHER INFORMATION: Amino acid linked to carboxy terminus via
      macrocycle-forming linker
<220> FEATURE:
<221> NAME/KEY: VARIANT
<222> LOCATION: (13)..(13)
<223> OTHER INFORMATION: P or A

<400> SEQUENCE: 11

Gln Ser Gln Thr Phe Ser Asn Xaa Xaa Xaa Leu Leu Xaa
1               5                   10

<210> SEQ ID NO 12
<211> LENGTH: 11
<212> TYPE: PRT
<213> ORGANISM: Artificial Sequence
<220> FEATURE:
<223> OTHER INFORMATION: engineered sequence
```

```
<220> FEATURE:
<221> NAME/KEY: VARIANT
<222> LOCATION: (1)..(1)
<223> OTHER INFORMATION: G or para-acetyl-phenylalanine (pAcF) or
      meta-acetyl-phenylalanine (mAcF)
<220> FEATURE:
<221> NAME/KEY: MISC_FEATURE
<222> LOCATION: (1)..(11)
<223> OTHER INFORMATION: Amino acid linked to carboxy terminus via
      macrocycle-forming linker
<220> FEATURE:
<221> NAME/KEY: VARIANT
<222> LOCATION: (4)..(4)
<223> OTHER INFORMATION: A or E or M
<220> FEATURE:
<221> NAME/KEY: VARIANT
<222> LOCATION: (5)..(5)
<223> OTHER INFORMATION: E or Q or A or H
<220> FEATURE:
<221> NAME/KEY: VARIANT
<222> LOCATION: (7)..(7)
<223> OTHER INFORMATION: W or 6-chloro-tryptophan (6Cl-W)
<220> FEATURE:
<221> NAME/KEY: VARIANT
<222> LOCATION: (8)..(8)
<223> OTHER INFORMATION: N or A
<220> FEATURE:
<221> NAME/KEY: VARIANT
<222> LOCATION: (9)..(9)
<223> OTHER INFORMATION: Leu or Q or 1-aminocyclopropanecarboxylic
      acid (Ac3c)
<220> FEATURE:
<221> NAME/KEY: VARIANT
<222> LOCATION: (10)..(10)
<223> OTHER INFORMATION: L or 2-amino-3-cyclobutylpropanoic acid (Cba)
<220> FEATURE:
<221> NAME/KEY: VARIANT
<222> LOCATION: (11)..(11)
<223> OTHER INFORMATION: A or G

<400> SEQUENCE: 12

Xaa Ser Phe Xaa Xaa Tyr Xaa Xaa Xaa Xaa Xaa
1               5                   10

<210> SEQ ID NO 13
<211> LENGTH: 11
<212> TYPE: PRT
<213> ORGANISM: Artificial Sequence
<220> FEATURE:
<223> OTHER INFORMATION: engineered sequence
<220> FEATURE:
<221> NAME/KEY: VARIANT
<222> LOCATION: (1)..(1)
<223> OTHER INFORMATION: T or L
<220> FEATURE:
<221> NAME/KEY: VARIANT
<222> LOCATION: (2)..(2)
<223> OTHER INFORMATION: G or para-acetyl-phenylalanine (pAcF)
<220> FEATURE:
<221> NAME/KEY: MISC_FEATURE
<222> LOCATION: (2)..(11)
<223> OTHER INFORMATION: Amino acid linked to carboxy terminus via
      macrocycle-forming linker
<220> FEATURE:
<221> NAME/KEY: VARIANT
<222> LOCATION: (4)..(4)
<223> OTHER INFORMATION: A or E or M
<220> FEATURE:
<221> NAME/KEY: VARIANT
<222> LOCATION: (5)..(5)
<223> OTHER INFORMATION: E or Q or A or H
<220> FEATURE:
<221> NAME/KEY: VARIANT
<222> LOCATION: (7)..(7)
<223> OTHER INFORMATION: W or 6-chloro-tryptophan (6Cl-W)
<220> FEATURE:
<221> NAME/KEY: VARIANT
```

```
<222> LOCATION: (8)..(8)
<223> OTHER INFORMATION: N or A
<220> FEATURE:
<221> NAME/KEY: VARIANT
<222> LOCATION: (9)..(9)
<223> OTHER INFORMATION: Leu or Q or 1-aminocyclopropanecarboxylic acid
      (Ac3c)
<220> FEATURE:
<221> NAME/KEY: VARIANT
<222> LOCATION: (10)..(10)
<223> OTHER INFORMATION: L or 2-amino-3-cyclobutylpropanoic acid (Cba)
<220> FEATURE:
<221> NAME/KEY: VARIANT
<222> LOCATION: (11)..(11)
<223> OTHER INFORMATION: A or G

<400> SEQUENCE: 13

Xaa Xaa Phe Xaa Xaa Tyr Xaa Xaa Xaa Xaa Xaa
1               5                   10

<210> SEQ ID NO 14
<211> LENGTH: 11
<212> TYPE: PRT
<213> ORGANISM: Artificial Sequence
<220> FEATURE:
<223> OTHER INFORMATION: engineered sequence
<220> FEATURE:
<221> NAME/KEY: VARIANT
<222> LOCATION: (1)..(1)
<223> OTHER INFORMATION: T or L
<220> FEATURE:
<221> NAME/KEY: VARIANT
<222> LOCATION: (4)..(4)
<223> OTHER INFORMATION: G or para-acetyl-phenylalanine (pAcF)
<220> FEATURE:
<221> NAME/KEY: MISC_FEATURE
<222> LOCATION: (4)..(11)
<223> OTHER INFORMATION: Amino acid linked to carboxy terminus via
      macrocycle-forming linker
<220> FEATURE:
<221> NAME/KEY: VARIANT
<222> LOCATION: (5)..(5)
<223> OTHER INFORMATION: E or Q or A or H
<220> FEATURE:
<221> NAME/KEY: VARIANT
<222> LOCATION: (7)..(7)
<223> OTHER INFORMATION: W or 6-chloro-tryptophan (6Cl-W)
<220> FEATURE:
<221> NAME/KEY: VARIANT
<222> LOCATION: (8)..(8)
<223> OTHER INFORMATION: N or A
<220> FEATURE:
<221> NAME/KEY: VARIANT
<222> LOCATION: (9)..(9)
<223> OTHER INFORMATION: Leu or Q or 1-aminocyclopropanecarboxylic acid
      (Ac3c)
<220> FEATURE:
<221> NAME/KEY: VARIANT
<222> LOCATION: (10)..(10)
<223> OTHER INFORMATION: L or 2-amino-3-cyclobutylpropanoic acid (Cba)
<220> FEATURE:
<221> NAME/KEY: VARIANT
<222> LOCATION: (11)..(11)
<223> OTHER INFORMATION: A or G

<400> SEQUENCE: 14

Xaa Ser Phe Xaa Xaa Tyr Xaa Xaa Xaa Xaa Xaa
1               5                   10

<210> SEQ ID NO 15
<211> LENGTH: 11
<212> TYPE: PRT
<213> ORGANISM: Artificial Sequence
<220> FEATURE:
<223> OTHER INFORMATION: engineered sequence
```

```
<220> FEATURE:
<221> NAME/KEY: VARIANT
<222> LOCATION: (1)..(1)
<223> OTHER INFORMATION: T or L
<220> FEATURE:
<221> NAME/KEY: VARIANT
<222> LOCATION: (4)..(4)
<223> OTHER INFORMATION: A or E or M
<220> FEATURE:
<221> NAME/KEY: VARIANT
<222> LOCATION: (5)..(5)
<223> OTHER INFORMATION: G or para-acetyl-phenylalanine (pAcF)
<220> FEATURE:
<221> NAME/KEY: MISC_FEATURE
<222> LOCATION: (5)..(11)
<223> OTHER INFORMATION: Amino acid linked to carboxy terminus via
      macrocycle-forming linker
<220> FEATURE:
<221> NAME/KEY: VARIANT
<222> LOCATION: (7)..(7)
<223> OTHER INFORMATION: W or 6-chloro-tryptophan (6Cl-W)
<220> FEATURE:
<221> NAME/KEY: VARIANT
<222> LOCATION: (8)..(8)
<223> OTHER INFORMATION: N or A
<220> FEATURE:
<221> NAME/KEY: VARIANT
<222> LOCATION: (9)..(9)
<223> OTHER INFORMATION: Leu or Q or 1-aminocyclopropanecarboxylic acid
      (Ac3c)
<220> FEATURE:
<221> NAME/KEY: VARIANT
<222> LOCATION: (10)..(10)
<223> OTHER INFORMATION: L or 2-amino-3-cyclobutylpropanoic acid (Cba)
<220> FEATURE:
<221> NAME/KEY: VARIANT
<222> LOCATION: (11)..(11)
<223> OTHER INFORMATION: A or G

<400> SEQUENCE: 15

Xaa Ser Phe Xaa Xaa Tyr Xaa Xaa Xaa Xaa Xaa
1               5                   10

<210> SEQ ID NO 16
<211> LENGTH: 11
<212> TYPE: PRT
<213> ORGANISM: Artificial Sequence
<220> FEATURE:
<223> OTHER INFORMATION: engineered sequence
<220> FEATURE:
<221> NAME/KEY: VARIANT
<222> LOCATION: (1)..(1)
<223> OTHER INFORMATION: T or L
<220> FEATURE:
<221> NAME/KEY: VARIANT
<222> LOCATION: (4)..(4)
<223> OTHER INFORMATION: A or E or M
<220> FEATURE:
<221> NAME/KEY: VARIANT
<222> LOCATION: (5)..(5)
<223> OTHER INFORMATION: E or Q or A or H
<220> FEATURE:
<221> NAME/KEY: VARIANT
<222> LOCATION: (6)..(6)
<223> OTHER INFORMATION: G or para-acetyl-phenylalanine (pAcF)
<220> FEATURE:
<221> NAME/KEY: MISC_FEATURE
<222> LOCATION: (6)..(11)
<223> OTHER INFORMATION: Amino acid linked to carboxy terminus via
      macrocycle-forming linker
<220> FEATURE:
<221> NAME/KEY: VARIANT
<222> LOCATION: (7)..(7)
<223> OTHER INFORMATION: W or 6-chloro-tryptophan (6Cl-W)
<220> FEATURE:
<221> NAME/KEY: VARIANT
<222> LOCATION: (8)..(8)
```

```
<223> OTHER INFORMATION: N or A
<220> FEATURE:
<221> NAME/KEY: VARIANT
<222> LOCATION: (9)..(9)
<223> OTHER INFORMATION: Leu or Q or 1-aminocyclopropanecarboxylic acid
      (Ac3c)
<220> FEATURE:
<221> NAME/KEY: VARIANT
<222> LOCATION: (10)..(10)
<223> OTHER INFORMATION: L or 2-amino-3-cyclobutylpropanoic acid (Cba)
<220> FEATURE:
<221> NAME/KEY: VARIANT
<222> LOCATION: (11)..(11)
<223> OTHER INFORMATION: A or G

<400> SEQUENCE: 16

Xaa Ser Phe Xaa Xaa Xaa Xaa Xaa Xaa Xaa Xaa
1               5                   10

<210> SEQ ID NO 17
<211> LENGTH: 11
<212> TYPE: PRT
<213> ORGANISM: Artificial Sequence
<220> FEATURE:
<223> OTHER INFORMATION: engineered sequence
<220> FEATURE:
<221> NAME/KEY: VARIANT
<222> LOCATION: (1)..(1)
<223> OTHER INFORMATION: T or L
<220> FEATURE:
<221> NAME/KEY: VARIANT
<222> LOCATION: (4)..(4)
<223> OTHER INFORMATION: A or E or M
<220> FEATURE:
<221> NAME/KEY: VARIANT
<222> LOCATION: (5)..(5)
<223> OTHER INFORMATION: E or Q or A or H
<220> FEATURE:
<221> NAME/KEY: VARIANT
<222> LOCATION: (7)..(7)
<223> OTHER INFORMATION: W or 6-chloro-tryptophan (6Cl-W)
<220> FEATURE:
<221> NAME/KEY: VARIANT
<222> LOCATION: (8)..(8)
<223> OTHER INFORMATION: G or para-acetyl-phenylalanine (pAcF)
<220> FEATURE:
<221> NAME/KEY: MISC_FEATURE
<222> LOCATION: (8)..(11)
<223> OTHER INFORMATION: Amino acid linked to carboxy terminus via
      macrocycle-forming linker
<220> FEATURE:
<221> NAME/KEY: VARIANT
<222> LOCATION: (9)..(9)
<223> OTHER INFORMATION: Leu or Q or 1-aminocyclopropanecarboxylic acid
      (Ac3c)
<220> FEATURE:
<221> NAME/KEY: VARIANT
<222> LOCATION: (10)..(10)
<223> OTHER INFORMATION: L or 2-amino-3-cyclobutylpropanoic acid (Cba)
<220> FEATURE:
<221> NAME/KEY: VARIANT
<222> LOCATION: (11)..(11)
<223> OTHER INFORMATION: A or G

<400> SEQUENCE: 17

Xaa Ser Phe Xaa Xaa Tyr Xaa Xaa Xaa Xaa Xaa
1               5                   10

<210> SEQ ID NO 18
<211> LENGTH: 11
<212> TYPE: PRT
<213> ORGANISM: Artificial Sequence
<220> FEATURE:
<223> OTHER INFORMATION: engineered sequence
<220> FEATURE:
```

```
<221> NAME/KEY: VARIANT
<222> LOCATION: (1)..(1)
<223> OTHER INFORMATION: G or para-acetyl-phenylalanine (pAcF)
<220> FEATURE:
<221> NAME/KEY: MISC_FEATURE
<222> LOCATION: (1)..(11)
<223> OTHER INFORMATION: Amino acid linked to carboxy terminus via
      macrocycle-forming linker
<220> FEATURE:
<221> NAME/KEY: VARIANT
<222> LOCATION: (4)..(4)
<223> OTHER INFORMATION: E or M
<220> FEATURE:
<221> NAME/KEY: VARIANT
<222> LOCATION: (5)..(5)
<223> OTHER INFORMATION: A or H or N or E
<220> FEATURE:
<221> NAME/KEY: VARIANT
<222> LOCATION: (7)..(7)
<223> OTHER INFORMATION: W or 6-chloro-tryptophan (6Cl-W)
<220> FEATURE:
<221> NAME/KEY: VARIANT
<222> LOCATION: (8)..(8)
<223> OTHER INFORMATION: N or A
<220> FEATURE:
<221> NAME/KEY: VARIANT
<222> LOCATION: (9)..(9)
<223> OTHER INFORMATION: Leu or Q or 1-aminocyclopropanecarboxylic acid
      (Ac3c)
<220> FEATURE:
<221> NAME/KEY: VARIANT
<222> LOCATION: (10)..(10)
<223> OTHER INFORMATION: L or 2-amino-3-cyclobutylpropanoic acid (Cba)
<220> FEATURE:
<221> NAME/KEY: VARIANT
<222> LOCATION: (11)..(11)
<223> OTHER INFORMATION: T or A or G

<400> SEQUENCE: 18

Xaa Thr Phe Xaa Xaa Tyr Xaa Xaa Xaa Xaa Xaa
1               5                   10

<210> SEQ ID NO 19
<211> LENGTH: 11
<212> TYPE: PRT
<213> ORGANISM: Artificial Sequence
<220> FEATURE:
<223> OTHER INFORMATION: engineered sequence
<220> FEATURE:
<221> NAME/KEY: VARIANT
<222> LOCATION: (1)..(1)
<223> OTHER INFORMATION: L or Q
<220> FEATURE:
<221> NAME/KEY: VARIANT
<222> LOCATION: (2)..(2)
<223> OTHER INFORMATION: G or para-acetyl-phenylalanine (pAcF)
<220> FEATURE:
<221> NAME/KEY: MISC_FEATURE
<222> LOCATION: (2)..(11)
<223> OTHER INFORMATION: Amino acid linked to carboxy terminus via
      macrocycle-forming linker
<220> FEATURE:
<221> NAME/KEY: VARIANT
<222> LOCATION: (4)..(4)
<223> OTHER INFORMATION: E or M
<220> FEATURE:
<221> NAME/KEY: VARIANT
<222> LOCATION: (5)..(5)
<223> OTHER INFORMATION: A or H or N or E
<220> FEATURE:
<221> NAME/KEY: VARIANT
<222> LOCATION: (7)..(7)
<223> OTHER INFORMATION: W or 6-chloro-tryptophan (6Cl-W)
<220> FEATURE:
<221> NAME/KEY: VARIANT
<222> LOCATION: (8)..(8)
<223> OTHER INFORMATION: N or A
```

```
<220> FEATURE:
<221> NAME/KEY: VARIANT
<222> LOCATION: (9)..(9)
<223> OTHER INFORMATION: Leu or Q or 1-aminocyclopropanecarboxylic acid
      (Ac3c)
<220> FEATURE:
<221> NAME/KEY: VARIANT
<222> LOCATION: (10)..(10)
<223> OTHER INFORMATION: L or 2-amino-3-cyclobutylpropanoic acid (Cba)
<220> FEATURE:
<221> NAME/KEY: VARIANT
<222> LOCATION: (11)..(11)
<223> OTHER INFORMATION: T or A or G

<400> SEQUENCE: 19

Xaa Xaa Phe Xaa Xaa Tyr Xaa Xaa Xaa Xaa Xaa
1               5                   10

<210> SEQ ID NO 20
<211> LENGTH: 11
<212> TYPE: PRT
<213> ORGANISM: Artificial Sequence
<220> FEATURE:
<223> OTHER INFORMATION: engineered sequence
<220> FEATURE:
<221> NAME/KEY: VARIANT
<222> LOCATION: (1)..(1)
<223> OTHER INFORMATION: L or Q
<220> FEATURE:
<221> NAME/KEY: VARIANT
<222> LOCATION: (4)..(4)
<223> OTHER INFORMATION: G or para-acetyl-phenylalanine (pAcF)
<220> FEATURE:
<221> NAME/KEY: MISC_FEATURE
<222> LOCATION: (4)..(11)
<223> OTHER INFORMATION: Amino acid linked to carboxy terminus via
      macrocycle-forming linker
<220> FEATURE:
<221> NAME/KEY: VARIANT
<222> LOCATION: (5)..(5)
<223> OTHER INFORMATION: A or H or N or E
<220> FEATURE:
<221> NAME/KEY: VARIANT
<222> LOCATION: (7)..(7)
<223> OTHER INFORMATION: W or 6-chloro-tryptophan (6Cl-W)
<220> FEATURE:
<221> NAME/KEY: VARIANT
<222> LOCATION: (8)..(8)
<223> OTHER INFORMATION: N or A
<220> FEATURE:
<221> NAME/KEY: VARIANT
<222> LOCATION: (9)..(9)
<223> OTHER INFORMATION: Leu or Q or 1-aminocyclopropanecarboxylic acid
      (Ac3c)
<220> FEATURE:
<221> NAME/KEY: VARIANT
<222> LOCATION: (10)..(10)
<223> OTHER INFORMATION: L or 2-amino-3-cyclobutylpropanoic acid (Cba)
<220> FEATURE:
<221> NAME/KEY: VARIANT
<222> LOCATION: (11)..(11)
<223> OTHER INFORMATION: T or A or G

<400> SEQUENCE: 20

Xaa Thr Phe Xaa Xaa Tyr Xaa Xaa Xaa Xaa Xaa
1               5                   10

<210> SEQ ID NO 21
<211> LENGTH: 11
<212> TYPE: PRT
<213> ORGANISM: Artificial Sequence
<220> FEATURE:
<223> OTHER INFORMATION: engineered sequence
<220> FEATURE:
<221> NAME/KEY: VARIANT
```

```
<222> LOCATION: (1)..(1)
<223> OTHER INFORMATION: L or Q
<220> FEATURE:
<221> NAME/KEY: VARIANT
<222> LOCATION: (4)..(4)
<223> OTHER INFORMATION: E or M
<220> FEATURE:
<221> NAME/KEY: VARIANT
<222> LOCATION: (5)..(5)
<223> OTHER INFORMATION: G or para-acetyl-phenylalanine (pAcF)
<220> FEATURE:
<221> NAME/KEY: MISC_FEATURE
<222> LOCATION: (5)..(11)
<223> OTHER INFORMATION: Amino acid linked to carboxy terminus via
      macrocycle-forming linker
<220> FEATURE:
<221> NAME/KEY: VARIANT
<222> LOCATION: (7)..(7)
<223> OTHER INFORMATION: W or 6-chloro-tryptophan (6Cl-W)
<220> FEATURE:
<221> NAME/KEY: VARIANT
<222> LOCATION: (8)..(8)
<223> OTHER INFORMATION: N or A
<220> FEATURE:
<221> NAME/KEY: VARIANT
<222> LOCATION: (9)..(9)
<223> OTHER INFORMATION: Leu or Q or 1-aminocyclopropanecarboxylic acid
      (Ac3c)
<220> FEATURE:
<221> NAME/KEY: VARIANT
<222> LOCATION: (10)..(10)
<223> OTHER INFORMATION: L or 2-amino-3-cyclobutylpropanoic acid (Cba)
<220> FEATURE:
<221> NAME/KEY: VARIANT
<222> LOCATION: (11)..(11)
<223> OTHER INFORMATION: T or A or G

<400> SEQUENCE: 21

Xaa Thr Phe Xaa Xaa Tyr Xaa Xaa Xaa Xaa Xaa
1               5                   10

<210> SEQ ID NO 22
<211> LENGTH: 11
<212> TYPE: PRT
<213> ORGANISM: Artificial Sequence
<220> FEATURE:
<223> OTHER INFORMATION: engineered sequence
<220> FEATURE:
<221> NAME/KEY: VARIANT
<222> LOCATION: (1)..(1)
<223> OTHER INFORMATION: L or Q
<220> FEATURE:
<221> NAME/KEY: VARIANT
<222> LOCATION: (4)..(4)
<223> OTHER INFORMATION: E or M
<220> FEATURE:
<221> NAME/KEY: VARIANT
<222> LOCATION: (5)..(5)
<223> OTHER INFORMATION: A or H or N or E
<220> FEATURE:
<221> NAME/KEY: VARIANT
<222> LOCATION: (6)..(6)
<223> OTHER INFORMATION: G or para-acetyl-phenylalanine (pAcF)
<220> FEATURE:
<221> NAME/KEY: MISC_FEATURE
<222> LOCATION: (6)..(11)
<223> OTHER INFORMATION: Amino acid linked to carboxy terminus via
      macrocycle-forming linker
<220> FEATURE:
<221> NAME/KEY: VARIANT
<222> LOCATION: (7)..(7)
<223> OTHER INFORMATION: W or 6-chloro-tryptophan (6Cl-W)
<220> FEATURE:
<221> NAME/KEY: VARIANT
<222> LOCATION: (8)..(8)
<223> OTHER INFORMATION: N or A
<220> FEATURE:
```

```
<221> NAME/KEY: VARIANT
<222> LOCATION: (9)..(9)
<223> OTHER INFORMATION: Leu or Q or 1-aminocyclopropanecarboxylic acid
      (Ac3c)
<220> FEATURE:
<221> NAME/KEY: VARIANT
<222> LOCATION: (10)..(10)
<223> OTHER INFORMATION: L or 2-amino-3-cyclobutylpropanoic acid (Cba)
<220> FEATURE:
<221> NAME/KEY: VARIANT
<222> LOCATION: (11)..(11)
<223> OTHER INFORMATION: T or A or G

<400> SEQUENCE: 22

Xaa Thr Phe Xaa Xaa Xaa Xaa Xaa Xaa Xaa Xaa
1               5                   10

<210> SEQ ID NO 23
<211> LENGTH: 11
<212> TYPE: PRT
<213> ORGANISM: Artificial Sequence
<220> FEATURE:
<223> OTHER INFORMATION: engineered sequence
<220> FEATURE:
<221> NAME/KEY: VARIANT
<222> LOCATION: (1)..(1)
<223> OTHER INFORMATION: L or Q
<220> FEATURE:
<221> NAME/KEY: VARIANT
<222> LOCATION: (4)..(4)
<223> OTHER INFORMATION: E or M
<220> FEATURE:
<221> NAME/KEY: VARIANT
<222> LOCATION: (5)..(5)
<223> OTHER INFORMATION: A or H or N or E
<220> FEATURE:
<221> NAME/KEY: VARIANT
<222> LOCATION: (7)..(7)
<223> OTHER INFORMATION: W or 6-chloro-tryptophan (6Cl-W)
<220> FEATURE:
<221> NAME/KEY: VARIANT
<222> LOCATION: (8)..(8)
<223> OTHER INFORMATION: G or para-acetyl-phenylalanine (pAcF)
<220> FEATURE:
<221> NAME/KEY: MISC_FEATURE
<222> LOCATION: (8)..(11)
<223> OTHER INFORMATION: Amino acid linked to carboxy terminus via
      macrocycle-forming linker
<220> FEATURE:
<221> NAME/KEY: VARIANT
<222> LOCATION: (9)..(9)
<223> OTHER INFORMATION: Leu or Q or 1-aminocyclopropanecarboxylic acid
      (Ac3c)
<220> FEATURE:
<221> NAME/KEY: VARIANT
<222> LOCATION: (10)..(10)
<223> OTHER INFORMATION: L or 2-amino-3-cyclobutylpropanoic acid (Cba)
<220> FEATURE:
<221> NAME/KEY: VARIANT
<222> LOCATION: (11)..(11)
<223> OTHER INFORMATION: T or A or G

<400> SEQUENCE: 23

Xaa Thr Phe Xaa Xaa Tyr Xaa Xaa Xaa Xaa Xaa
1               5                   10

<210> SEQ ID NO 24
<211> LENGTH: 10
<212> TYPE: PRT
<213> ORGANISM: Artificial Sequence
<220> FEATURE:
<223> OTHER INFORMATION: engineered sequence
<220> FEATURE:
<221> NAME/KEY: VARIANT
<222> LOCATION: (1)..(1)
```

```
<223> OTHER INFORMATION: G or para-acetyl-phenylalanine (pAcF)
<220> FEATURE:
<221> NAME/KEY: MISC_FEATURE
<222> LOCATION: (1)..(10)
<223> OTHER INFORMATION: Amino acid linked to carboxy terminus via
      macrocycle-forming linker
<220> FEATURE:
<221> NAME/KEY: VARIANT
<222> LOCATION: (4)..(4)
<223> OTHER INFORMATION: E or M
<220> FEATURE:
<221> NAME/KEY: VARIANT
<222> LOCATION: (5)..(5)
<223> OTHER INFORMATION: A or H or N or E
<220> FEATURE:
<221> NAME/KEY: VARIANT
<222> LOCATION: (7)..(7)
<223> OTHER INFORMATION: W or 6-chloro-tryptophan (6Cl-W)
<220> FEATURE:
<221> NAME/KEY: VARIANT
<222> LOCATION: (8)..(8)
<223> OTHER INFORMATION: E or A
<220> FEATURE:
<221> NAME/KEY: VARIANT
<222> LOCATION: (9)..(9)
<223> OTHER INFORMATION: Leu or Q or 1-aminocyclopropanecarboxylic acid
      (Ac3c)
<220> FEATURE:
<221> NAME/KEY: VARIANT
<222> LOCATION: (10)..(10)
<223> OTHER INFORMATION: L or 2-amino-3-cyclobutylpropanoic acid (Cba)

<400> SEQUENCE: 24

Xaa Thr Phe Xaa Xaa Tyr Xaa Xaa Xaa Xaa
1               5                   10

<210> SEQ ID NO 25
<211> LENGTH: 10
<212> TYPE: PRT
<213> ORGANISM: Artificial Sequence
<220> FEATURE:
<223> OTHER INFORMATION: engineered sequence
<220> FEATURE:
<221> NAME/KEY: VARIANT
<222> LOCATION: (1)..(1)
<223> OTHER INFORMATION: L or Q
<220> FEATURE:
<221> NAME/KEY: VARIANT
<222> LOCATION: (2)..(2)
<223> OTHER INFORMATION: G or para-acetyl-phenylalanine (pAcF)
<220> FEATURE:
<221> NAME/KEY: MISC_FEATURE
<222> LOCATION: (2)..(10)
<223> OTHER INFORMATION: Amino acid linked to carboxy terminus via
      macrocycle-forming linker
<220> FEATURE:
<221> NAME/KEY: VARIANT
<222> LOCATION: (4)..(4)
<223> OTHER INFORMATION: E or M
<220> FEATURE:
<221> NAME/KEY: VARIANT
<222> LOCATION: (5)..(5)
<223> OTHER INFORMATION: A or H or N or E
<220> FEATURE:
<221> NAME/KEY: VARIANT
<222> LOCATION: (7)..(7)
<223> OTHER INFORMATION: W or 6-chloro-tryptophan (6Cl-W)
<220> FEATURE:
<221> NAME/KEY: VARIANT
<222> LOCATION: (8)..(8)
<223> OTHER INFORMATION: E or A
<220> FEATURE:
<221> NAME/KEY: VARIANT
<222> LOCATION: (9)..(9)
<223> OTHER INFORMATION: Leu or Q or 1-aminocyclopropanecarboxylic acid
      (Ac3c)
<220> FEATURE:
```

```
<221> NAME/KEY: VARIANT
<222> LOCATION: (10)..(10)
<223> OTHER INFORMATION: L or 2-amino-3-cyclobutylpropanoic acid (Cba)

<400> SEQUENCE: 25

Xaa Xaa Phe Xaa Xaa Tyr Xaa Xaa Xaa Xaa
1               5                   10

<210> SEQ ID NO 26
<211> LENGTH: 10
<212> TYPE: PRT
<213> ORGANISM: Artificial Sequence
<220> FEATURE:
<223> OTHER INFORMATION: engineered sequence
<220> FEATURE:
<221> NAME/KEY: VARIANT
<222> LOCATION: (1)..(1)
<223> OTHER INFORMATION: L or Q
<220> FEATURE:
<221> NAME/KEY: VARIANT
<222> LOCATION: (4)..(4)
<223> OTHER INFORMATION: G or para-acetyl-phenylalanine (pAcF)
<220> FEATURE:
<221> NAME/KEY: MISC_FEATURE
<222> LOCATION: (4)..(10)
<223> OTHER INFORMATION: Amino acid linked to carboxy terminus via
      macrocycle-forming linker
<220> FEATURE:
<221> NAME/KEY: VARIANT
<222> LOCATION: (5)..(5)
<223> OTHER INFORMATION: A or H or N or E
<220> FEATURE:
<221> NAME/KEY: VARIANT
<222> LOCATION: (7)..(7)
<223> OTHER INFORMATION: W or 6-chloro-tryptophan (6Cl-W)
<220> FEATURE:
<221> NAME/KEY: VARIANT
<222> LOCATION: (8)..(8)
<223> OTHER INFORMATION: E or A
<220> FEATURE:
<221> NAME/KEY: VARIANT
<222> LOCATION: (9)..(9)
<223> OTHER INFORMATION: Leu or Q or 1-aminocyclopropanecarboxylic acid
      (Ac3c)
<220> FEATURE:
<221> NAME/KEY: VARIANT
<222> LOCATION: (10)..(10)
<223> OTHER INFORMATION: L or 2-amino-3-cyclobutylpropanoic acid (Cba)

<400> SEQUENCE: 26

Xaa Thr Phe Xaa Xaa Tyr Xaa Xaa Xaa Xaa
1               5                   10

<210> SEQ ID NO 27
<211> LENGTH: 10
<212> TYPE: PRT
<213> ORGANISM: Artificial Sequence
<220> FEATURE:
<223> OTHER INFORMATION: engineered sequence
<220> FEATURE:
<221> NAME/KEY: VARIANT
<222> LOCATION: (1)..(1)
<223> OTHER INFORMATION: L or Q
<220> FEATURE:
<221> NAME/KEY: VARIANT
<222> LOCATION: (4)..(4)
<223> OTHER INFORMATION: E or M
<220> FEATURE:
<221> NAME/KEY: VARIANT
<222> LOCATION: (5)..(5)
<223> OTHER INFORMATION: G or para-acetyl-phenylalanine (pAcF)
<220> FEATURE:
<221> NAME/KEY: MISC_FEATURE
<222> LOCATION: (5)..(10)
<223> OTHER INFORMATION: Amino acid linked to carboxy terminus via
```

```
            macrocycle-forming linker
<220> FEATURE:
<221> NAME/KEY: VARIANT
<222> LOCATION: (7)..(7)
<223> OTHER INFORMATION: W or 6-chloro-tryptophan (6Cl-W)
<220> FEATURE:
<221> NAME/KEY: VARIANT
<222> LOCATION: (8)..(8)
<223> OTHER INFORMATION: E or A
<220> FEATURE:
<221> NAME/KEY: VARIANT
<222> LOCATION: (9)..(9)
<223> OTHER INFORMATION: Leu or Q or 1-aminocyclopropanecarboxylic acid
      (Ac3c)
<220> FEATURE:
<221> NAME/KEY: VARIANT
<222> LOCATION: (10)..(10)
<223> OTHER INFORMATION: L or 2-amino-3-cyclobutylpropanoic acid (Cba)

<400> SEQUENCE: 27

Xaa Thr Phe Xaa Xaa Tyr Xaa Xaa Xaa Xaa
1               5                   10

<210> SEQ ID NO 28
<211> LENGTH: 10
<212> TYPE: PRT
<213> ORGANISM: Artificial Sequence
<220> FEATURE:
<223> OTHER INFORMATION: engineered sequence
<220> FEATURE:
<221> NAME/KEY: VARIANT
<222> LOCATION: (1)..(1)
<223> OTHER INFORMATION: L or Q
<220> FEATURE:
<221> NAME/KEY: VARIANT
<222> LOCATION: (4)..(4)
<223> OTHER INFORMATION: E or M
<220> FEATURE:
<221> NAME/KEY: VARIANT
<222> LOCATION: (5)..(5)
<223> OTHER INFORMATION: A or H or N or E
<220> FEATURE:
<221> NAME/KEY: VARIANT
<222> LOCATION: (6)..(6)
<223> OTHER INFORMATION: G or para-acetyl-phenylalanine (pAcF)
<220> FEATURE:
<221> NAME/KEY: MISC_FEATURE
<222> LOCATION: (6)..(10)
<223> OTHER INFORMATION: Amino acid linked to carboxy terminus via
      macrocycle-forming linker
<220> FEATURE:
<221> NAME/KEY: VARIANT
<222> LOCATION: (7)..(7)
<223> OTHER INFORMATION: W or 6-chloro-tryptophan (6Cl-W)
<220> FEATURE:
<221> NAME/KEY: VARIANT
<222> LOCATION: (8)..(8)
<223> OTHER INFORMATION: E or A
<220> FEATURE:
<221> NAME/KEY: VARIANT
<222> LOCATION: (9)..(9)
<223> OTHER INFORMATION: Leu or Q or 1-aminocyclopropanecarboxylic acid
      (Ac3c)
<220> FEATURE:
<221> NAME/KEY: VARIANT
<222> LOCATION: (10)..(10)
<223> OTHER INFORMATION: L or 2-amino-3-cyclobutylpropanoic acid (Cba)

<400> SEQUENCE: 28

Xaa Thr Phe Xaa Xaa Xaa Xaa Xaa Xaa Xaa
1               5                   10

<210> SEQ ID NO 29
<211> LENGTH: 10
<212> TYPE: PRT
```

```
<213> ORGANISM: Artificial Sequence
<220> FEATURE:
<223> OTHER INFORMATION: engineered sequence
<220> FEATURE:
<221> NAME/KEY: VARIANT
<222> LOCATION: (1)..(1)
<223> OTHER INFORMATION: G or para-acetyl-phenylalanine (pAcF)
<220> FEATURE:
<221> NAME/KEY: MISC_FEATURE
<222> LOCATION: (1)..(10)
<223> OTHER INFORMATION: Amino acid linked to carboxy terminus via
      macrocycle-forming linker
<220> FEATURE:
<221> NAME/KEY: VARIANT
<222> LOCATION: (4)..(4)
<223> OTHER INFORMATION: 2-aminoisobutyric acid (Aib) or H or N
<220> FEATURE:
<221> NAME/KEY: VARIANT
<222> LOCATION: (6)..(6)
<223> OTHER INFORMATION: W or 6-chloro-tryptophan (6Cl-W)
<220> FEATURE:
<221> NAME/KEY: VARIANT
<222> LOCATION: (7)..(7)
<223> OTHER INFORMATION: E or A
<220> FEATURE:
<221> NAME/KEY: VARIANT
<222> LOCATION: (8)..(8)
<223> OTHER INFORMATION: Leu or Q or 1-aminocyclopropanecarboxylic acid
      (Ac3c)
<220> FEATURE:
<221> NAME/KEY: VARIANT
<222> LOCATION: (9)..(9)
<223> OTHER INFORMATION: L or 2-amino-3-cyclobutylpropanoic acid (Cba)
<220> FEATURE:
<221> NAME/KEY: VARIANT
<222> LOCATION: (10)..(10)
<223> OTHER INFORMATION: T or A or G

<400> SEQUENCE: 29

Xaa Phe Met Xaa Tyr Xaa Xaa Xaa Xaa Xaa
1               5                   10

<210> SEQ ID NO 30
<211> LENGTH: 9
<212> TYPE: PRT
<213> ORGANISM: Artificial Sequence
<220> FEATURE:
<223> OTHER INFORMATION: engineered sequence
<220> FEATURE:
<221> NAME/KEY: VARIANT
<222> LOCATION: (2)..(2)
<223> OTHER INFORMATION: G or para-acetyl-phenylalanine (pAcF)
<220> FEATURE:
<221> NAME/KEY: MISC_FEATURE
<222> LOCATION: (2)..(9)
<223> OTHER INFORMATION: Amino acid linked to carboxy terminus via
      macrocycle-forming linker
<220> FEATURE:
<221> NAME/KEY: VARIANT
<222> LOCATION: (3)..(3)
<223> OTHER INFORMATION: 2-aminoisobutyric acid (Aib) or H or N
<220> FEATURE:
<221> NAME/KEY: VARIANT
<222> LOCATION: (5)..(5)
<223> OTHER INFORMATION: W or 6-chloro-tryptophan (6Cl-W)
<220> FEATURE:
<221> NAME/KEY: VARIANT
<222> LOCATION: (6)..(6)
<223> OTHER INFORMATION: E or A
<220> FEATURE:
<221> NAME/KEY: VARIANT
<222> LOCATION: (7)..(7)
<223> OTHER INFORMATION: Leu or Q or 1-aminocyclopropanecarboxylic acid
      (Ac3c)
<220> FEATURE:
<221> NAME/KEY: VARIANT
<222> LOCATION: (8)..(8)
```

```
<223> OTHER INFORMATION: L or 2-amino-3-cyclobutylpropanoic acid (Cba)
<220> FEATURE:
<221> NAME/KEY: VARIANT
<222> LOCATION: (9)..(9)
<223> OTHER INFORMATION: T or A or G

<400> SEQUENCE: 30

Phe Xaa Xaa Tyr Xaa Xaa Xaa Xaa Xaa
1               5

<210> SEQ ID NO 31
<211> LENGTH: 9
<212> TYPE: PRT
<213> ORGANISM: Artificial Sequence
<220> FEATURE:
<223> OTHER INFORMATION: engineered sequence
<220> FEATURE:
<221> NAME/KEY: VARIANT
<222> LOCATION: (3)..(3)
<223> OTHER INFORMATION: G or para-acetyl-phenylalanine (pAcF)
<220> FEATURE:
<221> NAME/KEY: MISC_FEATURE
<222> LOCATION: (3)..(9)
<223> OTHER INFORMATION: Amino acid linked to carboxy terminus via
      macrocycle-forming linker
<220> FEATURE:
<221> NAME/KEY: VARIANT
<222> LOCATION: (5)..(5)
<223> OTHER INFORMATION: W or 6-chloro-tryptophan (6Cl-W)
<220> FEATURE:
<221> NAME/KEY: VARIANT
<222> LOCATION: (6)..(6)
<223> OTHER INFORMATION: E or A
<220> FEATURE:
<221> NAME/KEY: VARIANT
<222> LOCATION: (7)..(7)
<223> OTHER INFORMATION: Leu or Q or 1-aminocyclopropanecarboxylic acid
      (Ac3c)
<220> FEATURE:
<221> NAME/KEY: VARIANT
<222> LOCATION: (8)..(8)
<223> OTHER INFORMATION: L or 2-amino-3-cyclobutylpropanoic acid (Cba)
<220> FEATURE:
<221> NAME/KEY: VARIANT
<222> LOCATION: (9)..(9)
<223> OTHER INFORMATION: T or A or G

<400> SEQUENCE: 31

Phe Met Xaa Tyr Xaa Xaa Xaa Xaa Xaa
1               5

<210> SEQ ID NO 32
<211> LENGTH: 9
<212> TYPE: PRT
<213> ORGANISM: Artificial Sequence
<220> FEATURE:
<223> OTHER INFORMATION: engineered sequence
<220> FEATURE:
<221> NAME/KEY: VARIANT
<222> LOCATION: (3)..(3)
<223> OTHER INFORMATION: 2-aminoisobutyric acid (Aib) or H or N
<220> FEATURE:
<221> NAME/KEY: VARIANT
<222> LOCATION: (4)..(4)
<223> OTHER INFORMATION: G or para-acetyl-phenylalanine (pAcF)
<220> FEATURE:
<221> NAME/KEY: MISC_FEATURE
<222> LOCATION: (4)..(9)
<223> OTHER INFORMATION: Amino acid linked to carboxy terminus via
      macrocycle-forming linker
<220> FEATURE:
<221> NAME/KEY: VARIANT
<222> LOCATION: (5)..(5)
<223> OTHER INFORMATION: W or 6-chloro-tryptophan (6Cl-W)
<220> FEATURE:
```

```
<221> NAME/KEY: VARIANT
<222> LOCATION: (6)..(6)
<223> OTHER INFORMATION: E or A
<220> FEATURE:
<221> NAME/KEY: VARIANT
<222> LOCATION: (7)..(7)
<223> OTHER INFORMATION: Leu or Q or 1-aminocyclopropanecarboxylic acid
      (Ac3c)
<220> FEATURE:
<221> NAME/KEY: VARIANT
<222> LOCATION: (8)..(8)
<223> OTHER INFORMATION: L or 2-amino-3-cyclobutylpropanoic acid (Cba)
<220> FEATURE:
<221> NAME/KEY: VARIANT
<222> LOCATION: (9)..(9)
<223> OTHER INFORMATION: T or A or G

<400> SEQUENCE: 32

Phe Met Xaa Xaa Xaa Xaa Xaa Xaa Xaa
1               5

<210> SEQ ID NO 33
<211> LENGTH: 9
<212> TYPE: PRT
<213> ORGANISM: Artificial Sequence
<220> FEATURE:
<223> OTHER INFORMATION: engineered sequence
<220> FEATURE:
<221> NAME/KEY: VARIANT
<222> LOCATION: (3)..(3)
<223> OTHER INFORMATION: 2-aminoisobutyric acid (Aib) or H or N
<220> FEATURE:
<221> NAME/KEY: VARIANT
<222> LOCATION: (5)..(5)
<223> OTHER INFORMATION: W or 6-chloro-tryptophan (6Cl-W)
<220> FEATURE:
<221> NAME/KEY: VARIANT
<222> LOCATION: (6)..(6)
<223> OTHER INFORMATION: G or para-acetyl-phenylalanine (pAcF)
<220> FEATURE:
<221> NAME/KEY: MISC_FEATURE
<222> LOCATION: (6)..(9)
<223> OTHER INFORMATION: Amino acid linked to carboxy terminus via
      macrocycle-forming linker
<220> FEATURE:
<221> NAME/KEY: VARIANT
<222> LOCATION: (7)..(7)
<223> OTHER INFORMATION: Leu or Q or 1-aminocyclopropanecarboxylic acid
      (Ac3c)
<220> FEATURE:
<221> NAME/KEY: VARIANT
<222> LOCATION: (8)..(8)
<223> OTHER INFORMATION: L or 2-amino-3-cyclobutylpropanoic acid (Cba)
<220> FEATURE:
<221> NAME/KEY: VARIANT
<222> LOCATION: (9)..(9)
<223> OTHER INFORMATION: T or A or G

<400> SEQUENCE: 33

Phe Met Xaa Tyr Xaa Xaa Xaa Xaa Xaa
1               5

<210> SEQ ID NO 34
<211> LENGTH: 9
<212> TYPE: PRT
<213> ORGANISM: Artificial Sequence
<220> FEATURE:
<223> OTHER INFORMATION: engineered sequence
<220> FEATURE:
<221> NAME/KEY: VARIANT
<222> LOCATION: (1)..(1)
<223> OTHER INFORMATION: G or para-acetyl-phenylalanine (pAcF)
<220> FEATURE:
<221> NAME/KEY: MISC_FEATURE
<222> LOCATION: (1)..(9)
```

```
<223> OTHER INFORMATION: Amino acid linked to carboxy terminus via
      macrocycle-forming linker
<220> FEATURE:
<221> NAME/KEY: VARIANT
<222> LOCATION: (4)..(4)
<223> OTHER INFORMATION: 2-aminoisobutyric acid (Aib) or H or N
<220> FEATURE:
<221> NAME/KEY: VARIANT
<222> LOCATION: (6)..(6)
<223> OTHER INFORMATION: W or 6-chloro-tryptophan (6Cl-W)
<220> FEATURE:
<221> NAME/KEY: VARIANT
<222> LOCATION: (7)..(7)
<223> OTHER INFORMATION: E or A
<220> FEATURE:
<221> NAME/KEY: VARIANT
<222> LOCATION: (8)..(8)
<223> OTHER INFORMATION: Leu or Q or 1-aminocyclopropanecarboxylic acid
      (Ac3c)
<220> FEATURE:
<221> NAME/KEY: VARIANT
<222> LOCATION: (9)..(9)
<223> OTHER INFORMATION: L or 2-amino-3-cyclobutylpropanoic acid (Cba)

<400> SEQUENCE: 34

Xaa Phe Met Xaa Tyr Xaa Xaa Xaa Xaa
1               5

<210> SEQ ID NO 35
<211> LENGTH: 8
<212> TYPE: PRT
<213> ORGANISM: Artificial Sequence
<220> FEATURE:
<223> OTHER INFORMATION: engineered sequence
<220> FEATURE:
<221> NAME/KEY: VARIANT
<222> LOCATION: (2)..(2)
<223> OTHER INFORMATION: G or para-acetyl-phenylalanine (pAcF)
<220> FEATURE:
<221> NAME/KEY: MISC_FEATURE
<222> LOCATION: (2)..(8)
<223> OTHER INFORMATION: Amino acid linked to carboxy terminus via
      macrocycle-forming linker
<220> FEATURE:
<221> NAME/KEY: VARIANT
<222> LOCATION: (3)..(3)
<223> OTHER INFORMATION: 2-aminoisobutyric acid (Aib) or H or N
<220> FEATURE:
<221> NAME/KEY: VARIANT
<222> LOCATION: (5)..(5)
<223> OTHER INFORMATION: W or 6-chloro-tryptophan (6Cl-W)
<220> FEATURE:
<221> NAME/KEY: VARIANT
<222> LOCATION: (6)..(6)
<223> OTHER INFORMATION: E or A
<220> FEATURE:
<221> NAME/KEY: VARIANT
<222> LOCATION: (7)..(7)
<223> OTHER INFORMATION: Leu or Q or 1-aminocyclopropanecarboxylic acid
      (Ac3c)
<220> FEATURE:
<221> NAME/KEY: VARIANT
<222> LOCATION: (8)..(8)
<223> OTHER INFORMATION: L or 2-amino-3-cyclobutylpropanoic acid (Cba)

<400> SEQUENCE: 35

Phe Xaa Xaa Tyr Xaa Xaa Xaa Xaa
1               5

<210> SEQ ID NO 36
<211> LENGTH: 8
<212> TYPE: PRT
<213> ORGANISM: Artificial Sequence
<220> FEATURE:
<223> OTHER INFORMATION: engineered sequence
```

```
<220> FEATURE:
<221> NAME/KEY: VARIANT
<222> LOCATION: (3)..(3)
<223> OTHER INFORMATION: G or para-acetyl-phenylalanine (pAcF)
<220> FEATURE:
<221> NAME/KEY: MISC_FEATURE
<222> LOCATION: (3)..(8)
<223> OTHER INFORMATION: Amino acid linked to carboxy terminus via
      macrocycle-forming linker
<220> FEATURE:
<221> NAME/KEY: VARIANT
<222> LOCATION: (5)..(5)
<223> OTHER INFORMATION: W or 6-chloro-tryptophan (6Cl-W)
<220> FEATURE:
<221> NAME/KEY: VARIANT
<222> LOCATION: (6)..(6)
<223> OTHER INFORMATION: E or A
<220> FEATURE:
<221> NAME/KEY: VARIANT
<222> LOCATION: (7)..(7)
<223> OTHER INFORMATION: Leu or Q or 1-aminocyclopropanecarboxylic acid
      (Ac3c)
<220> FEATURE:
<221> NAME/KEY: VARIANT
<222> LOCATION: (8)..(8)
<223> OTHER INFORMATION: L or 2-amino-3-cyclobutylpropanoic acid (Cba)

<400> SEQUENCE: 36

Phe Met Xaa Tyr Xaa Xaa Xaa Xaa
1               5

<210> SEQ ID NO 37
<211> LENGTH: 8
<212> TYPE: PRT
<213> ORGANISM: Artificial Sequence
<220> FEATURE:
<223> OTHER INFORMATION: engineered sequence
<220> FEATURE:
<221> NAME/KEY: VARIANT
<222> LOCATION: (3)..(3)
<223> OTHER INFORMATION: 2-aminoisobutyric acid (Aib) or H or N
<220> FEATURE:
<221> NAME/KEY: VARIANT
<222> LOCATION: (4)..(4)
<223> OTHER INFORMATION: G or para-acetyl-phenylalanine (pAcF)
<220> FEATURE:
<221> NAME/KEY: MISC_FEATURE
<222> LOCATION: (4)..(8)
<223> OTHER INFORMATION: Amino acid linked to carboxy terminus via
      macrocycle-forming linker
<220> FEATURE:
<221> NAME/KEY: VARIANT
<222> LOCATION: (5)..(5)
<223> OTHER INFORMATION: W or 6-chloro-tryptophan (6Cl-W)
<220> FEATURE:
<221> NAME/KEY: VARIANT
<222> LOCATION: (6)..(6)
<223> OTHER INFORMATION: E or A
<220> FEATURE:
<221> NAME/KEY: VARIANT
<222> LOCATION: (7)..(7)
<223> OTHER INFORMATION: Leu or Q or 1-aminocyclopropanecarboxylic acid
      (Ac3c)
<220> FEATURE:
<221> NAME/KEY: VARIANT
<222> LOCATION: (8)..(8)
<223> OTHER INFORMATION: L or 2-amino-3-cyclobutylpropanoic acid (Cba)

<400> SEQUENCE: 37

Phe Met Xaa Xaa Xaa Xaa Xaa Xaa
1               5

<210> SEQ ID NO 38
<211> LENGTH: 12
<212> TYPE: PRT
```

```
<213> ORGANISM: Artificial Sequence
<220> FEATURE:
<223> OTHER INFORMATION: engineered sequence
<220> FEATURE:
<221> NAME/KEY: VARIANT
<222> LOCATION: (6)..(6)
<223> OTHER INFORMATION: G or para-acetyl-phenylalanine (pAcF)
<220> FEATURE:
<221> NAME/KEY: MISC_FEATURE
<222> LOCATION: (6)..(12)
<223> OTHER INFORMATION: Amino acid linked to carboxy terminus via
      macrocycle-forming linker

<400> SEQUENCE: 38

Gly Thr Ser Phe Ala Xaa Tyr Trp Asn Leu Leu Ala
1               5                   10

<210> SEQ ID NO 39
<211> LENGTH: 12
<212> TYPE: PRT
<213> ORGANISM: Artificial Sequence
<220> FEATURE:
<223> OTHER INFORMATION: engineered sequence
<220> FEATURE:
<221> NAME/KEY: VARIANT
<222> LOCATION: (2)..(2)
<223> OTHER INFORMATION: G or para-acetyl-phenylalanine (pAcF)
<220> FEATURE:
<221> NAME/KEY: MISC_FEATURE
<222> LOCATION: (2)..(12)
<223> OTHER INFORMATION: Amino acid linked to carboxy terminus via
      macrocycle-forming linker

<400> SEQUENCE: 39

Gly Xaa Ser Phe Ala Glu Tyr Trp Asn Leu Leu Ala
1               5                   10

<210> SEQ ID NO 40
<211> LENGTH: 43
<212> TYPE: DNA
<213> ORGANISM: Artificial Sequence
<220> FEATURE:
<223> OTHER INFORMATION: engineered sequence

<400> SEQUENCE: 40
gcgattggaa cctgctggcg tgcatcacgg gagatgcact agt                         43

<210> SEQ ID NO 41
<211> LENGTH: 52
<212> TYPE: DNA
<213> ORGANISM: Artificial Sequence
<220> FEATURE:
<223> OTHER INFORMATION: engineered sequence

<400> SEQUENCE: 41
ctagacatat gggctagagc ttcgcggaat attggaacct gctggcgtgc at               52

<210> SEQ ID NO 42
<211> LENGTH: 23
<212> TYPE: DNA
<213> ORGANISM: Artificial Sequence
<220> FEATURE:
<223> OTHER INFORMATION: engineered sequence

<400> SEQUENCE: 42
gctagttatt gctcagcggt ggc                                               23

<210> SEQ ID NO 43
<211> LENGTH: 12
```

```
<212> TYPE: PRT
<213> ORGANISM: Artificial Sequence
<220> FEATURE:
<223> OTHER INFORMATION: Engineered Sequence

<400> SEQUENCE: 43

Gly Thr Ser Phe Ala Tyr Tyr Trp Asn Leu Leu Ala
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Engineered Sequence

<400> SEQUENCE: 44

Gly Tyr Ser Phe Ala Glu Tyr Trp Asn Leu Leu Ala
1               5                   10
```

MACROCYCLIC PEPTIDOMIMETICS FOR ALPHA-HELIX MIMICRY

CROSS-REFERENCE TO RELATED APPLICATIONS

This application is a national stage application under 35 U.S.C. § 371 of PCT Application No. PCT/US15/23883, filed Apr. 1, 2015, which claims priority to and the benefit of U.S. provisional patent application Ser. No. 61/973,994, entitled MACROCYCLIC PEPTIDOMIMETICS FOR ALPHA-HELIX MIMICRY, filed Apr. 2, 2014, which is incorporated herein by reference in its entirety.

STATEMENT REGARDING FEDERALLY SPONSORED RESEARCH OR DEVELOPMENT

This invention was made with government support under contract no. CHE-1112342 awarded by the National Science Foundation and under contract no. CA187502 awarded by the National Institutes of Health. The government has certain rights in the invention.

1. TECHNICAL FIELD

The present invention relates to macrocyclic peptides constrained by side-chain-to-C-end non-peptidic tethers for use as functional and structural mimics of α-helical motifs. The invention also relates to methods of preparing such macrocycles as well as methods for using them in therapeutic applications.

2. BACKGROUND

Peptides represent valuable tools for investigating biological systems, studying the binding and activity properties of biomolecules (e.g., enzymes, cell receptors, antibodies, kinases), and for validating pharmacological targets. Peptide-based molecules have also attracted increasing attention as therapeutic agents, in particular in the context of challenging drug targets such protein-protein and protein-nucleic acids interactions. While many peptides exhibit interesting biological activity, linear peptides do not generally represent suitable pharmacological agents due to poor proteolytic and metabolic stability, limited cell permeability, and promiscuous binding as a result of conformational flexibility. The use of molecular constraints to restrict the conformational freedom of the molecule backbone can be used to overcome these limitations. In many cases, conformationally constrained peptides exhibit enhanced enzymatic stability (Fairlie, Tyndall et al. 2000; Wang, Liao et al. 2005), membrane permeability (Walensky, Kung et al. 2004; Rezai, Bock et al. 2006; Rezai, Yu et al. 2006), and protein binding affinity (Tang, Yuan et al. 1999; Dias, Fasan et al. 2006) and selectivity (Henchey, Porter et al. 2010), compared to their linear counterparts. Constraints that lock-in the active conformation of a peptide molecule can result in increased affinity due to the reduced conformational entropy loss upon binding to the receptor. Macrocyclic peptides have thus emerged as promising molecular scaffolds for the development of bioactive compounds and therapeutic agents (Katsara, Tselios et al. 2006; Driggers, Hale et al. 2008; Obrecht, Robinson et al. 2009; Marsault and Peterson 2011).

Reflecting its abundance in protein structures, α-helices are often encountered at the interface of protein-protein and protein-nucleic acids complexes (Jochim and Arora 2009). Once excised from the protein context, linear peptides encompassing these secondary structural motifs rarely adopt a stable α-helical conformation in solution. Accordingly, a number of strategies have been developed for stabilization and mimicry of α-helical peptides (Henchey, Jochim et al. 2008) as a means to generate bioactive molecules that can target and modulate these biomolecular interactions. A common approach in this area has involved the use of covalent inter-side-chain linkages such as disulfide bonds (Jackson, King et al. 1991), lactam (Osapay and Taylor 1992), thio-ether (Brunel and Dawson 2005) or triazole (Scrima, Le Chevalier-Isaad et al. 2010; Kawamoto, Coleska et al. 2012) bridges, 'hydrocarbon staples' (Blackwell and Grubbs 1998; Schafmeister, Po et al. 2000; Bernal, Wade et al. 2010), and cysteine cross-linking moieties (Zhang, Sadovski et al. 2007; Muppidi, Wang et al. 2011; Jo, Meinhardt et al. 2012; Spokoyny, Zou et al. 2013). Another approach has entailed the stabilization of α-helical peptides via the introduction of so-called 'hydrogen bond surrogates', i.e. hydrocarbon linkages replacing an N-terminal i/i+4 hydrogen bond (Wang, Liao et al. 2005).

Citation or identification of any reference in Section 2, or in any other section of this application, shall not be considered an admission that such reference is available as prior art to the present invention.

3. SUMMARY

Provided is a macrocyclic peptidomimetic molecule of Formula (I):

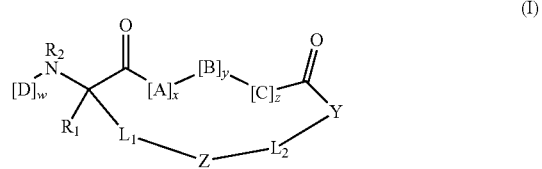

wherein:
each of A, C, and D is independently a natural or non-natural amino acid;
B is a natural amino acid, non-natural amino acid, an amino acid comprising at least one additional methylene groups between the amino and carboxyl group, an amino acid comprising an amino group which is a secondary or tertiary amine, an amino acid comprising a carboxy group replaced by an ester, [—NHN($R_3$)C(O)—], [—NH-$L_3$-CO—], [—NH-$L_3$-SO$_2$—], or [—NH-$L_3$-];
Y is —NH—, —N($R_4$)—, —NHN($R_4$)—, —NH—O—, —O—, or —S—;
Z is —SCH($R_6$)—, —CHR$_6$S—, —C≡C—, —N($R_5$)CO—, —CON($R_6$)—, —C($R_5$)=N($R_6$)—, —CH($R_5$)—NH($R_6$)—, —C($R_5$)=N—O—, —CH($R_5$)—NH—O—, —C($R_5$)=N—NH($R_6$)—, —CH($R_5$)—NH—NH($R_6$)—, or a triazole group;
$L_1$, $L_2$, and $L_3$ are independently aliphatic, aryl, substituted aliphatic, substituted aryl, heteroatom-containing aliphatic, heteroatom-containing aryl, substituted heteroatom-containing aliphatic, or substituted heteroatom-containing aryl groups, each being unsubstituted or substituted with $R_7$;
$R_1$, $R_2$, $R_3$, $R_4$, $R_5$, and $R_6$ are independently —H, an aliphatic, a substituted aliphatic, aryl, or a substituted aryl group;

each $R_7$ is independently —H, an aliphatic, a substituted aliphatic, an aryl, a substituted aryl group;

x is an integer from 0-10;

y is an integer from 0-10;

z is an integer from 0-10;

w is an integer from 1-1000;

x+y+z is at least 3; and wherein the macrocyclic peptidomimetic molecule comprises an alpha-helix.

In one embodiment, the macrocyclic peptidomimetic molecule has increased stability compared to a corresponding non-macrocyclic polypeptide, wherein the non-macrocyclic polypeptide lacks [Z-$L_2$-Y].

In another embodiment, terminal D comprises a capping group.

In another embodiment of the macrocyclic peptidomimetic molecule, a secondary structure of the macrocyclic peptidomimetic molecule is more stable than a corresponding secondary structure of a corresponding non-macrocyclic polypeptide, wherein the non-macrocyclic polypeptide lacks [Z-$L_2$-Y].

In another embodiment of the macrocyclic peptidomimetic molecule, the secondary structure of the macrocyclic peptidomimetic molecule corresponds to an alpha-helix.

In another embodiment of the macrocyclic peptidomimetic molecule, the macrocyclic peptidomimetic molecule has increased proteolytic stability compared to a corresponding non-macrocyclic polypeptide, wherein the non-macrocyclic polypeptide lacks [Z-$L_2$-Y].

In another embodiment of the macrocyclic peptidomimetic molecule, the macrocyclic peptidomimetic molecule has increased biological activity compared to a corresponding non-macrocyclic polypeptide, wherein the non-macrocyclic polypeptide lacks [Z-$L_2$-Y].

In another embodiment of the macrocyclic peptidomimetic molecule, the macrocyclic peptidomimetic molecule has ability to penetrate living cells compared to a corresponding non-macrocyclic polypeptide, wherein the non-macrocyclic polypeptide lacks [Z-$L_2$-Y].

In another embodiment of the macrocyclic peptidomimetic molecule, the alpha-helix comprises from one (1) turn to 5 turns.

In another embodiment of the macrocyclic peptidomimetic molecule, [-$L_1$-Z-$L_2$-Y-] spans from one (1) turn to 5 turns of the alpha-helix.

In another embodiment of the macrocyclic peptidomimetic molecule, the length of [-$L_1$-Z-$L_2$-Y-] is about 4 Å to about 12 Å per turn of the alpha-helix.

In another embodiment of the macrocyclic peptidomimetic molecule, [-$L_1$-Z-$L_2$-Y-] spans approximately one (1) turn of the alpha-helix.

In another embodiment of the macrocyclic peptidomimetic molecule, the length of [-$L_1$-Z-$L_2$-Y-] is approximately equal to the length of from about 5 carbon-carbon bonds to about 11 carbon-carbon bonds.

In another embodiment of the macrocyclic peptidomimetic molecule, the macrocycle comprises a ring of about 15 atoms to 21 atoms.

In another embodiment of the macrocyclic peptidomimetic molecule, [-$L_1$-Z-$L_2$-Y-] spans approximately two (2) turns of the alpha-helix.

In another embodiment of the macrocyclic peptidomimetic molecule, the length of [-$L_1$-Z-$L_2$-Y-] is approximately equal to the length of from about 7 carbon-carbon bonds to about 17 carbon-carbon bonds.

In another embodiment of the macrocyclic peptidomimetic molecule, the macrocycle comprises a ring of about 28 atoms to 38 atoms.

In another embodiment of the macrocyclic peptidomimetic molecule, [-$L_1$-Z-$L_2$-Y-] spans approximately three (3) turns of the alpha-helix.

In another embodiment of the macrocyclic peptidomimetic molecule, the length of [-$L_1$-Z-$L_2$-Y-] is approximately equal to the length of from about 12 carbon-carbon bonds to about 22 carbon-carbon bonds.

In another embodiment of the macrocyclic peptidomimetic molecule, the macrocycle comprises a ring of about 43 atoms to 53 atoms.

In another embodiment of the macrocyclic peptidomimetic molecule, [-$L_1$-Z-$L_2$-Y-] spans approximately four (4) turns of the alpha-helix.

In another embodiment of the macrocyclic peptidomimetic molecule, the length of [-$L_1$-Z-$L_2$-Y-] is approximately equal to the length of from about 17 carbon-carbon bonds to about 28 carbon-carbon bonds.

In another embodiment of the macrocyclic peptidomimetic molecule, the macrocycle comprises a ring of about 59 atoms to 70 atoms.

In another embodiment of the macrocyclic peptidomimetic molecule, [-$L_1$-Z-$L_2$-Y-] spans approximately five (5) turns of the alpha-helix.

In another embodiment of the macrocyclic peptidomimetic molecule, the length of [-$L_1$-Z-$L_2$-Y-] is approximately equal to the length of from about 22 carbon-carbon bonds to about 35 carbon-carbon bonds.

In another embodiment of the macrocyclic peptidomimetic molecule, the macrocycle comprises a ring of about 75 atoms to 88 atoms.

In another embodiment of the macrocyclic peptidomimetic molecule, $R_1$ is methyl.

In another embodiment of the macrocyclic peptidomimetic molecule, the macrocyclic peptidomimetic molecule further comprises a fluorescent label, an affinity label, a radioisotopic label, a targeting agent, or a therapeutic agent.

In another embodiment of the macrocyclic peptidomimetic molecule, the macrocycle-forming linker [-$L_1$-Z-$L_2$-Y-] is selected from a group of macrocycle-forming linkers consisting of

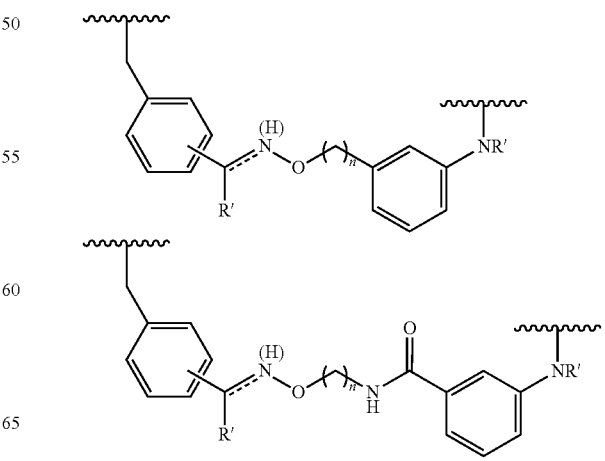

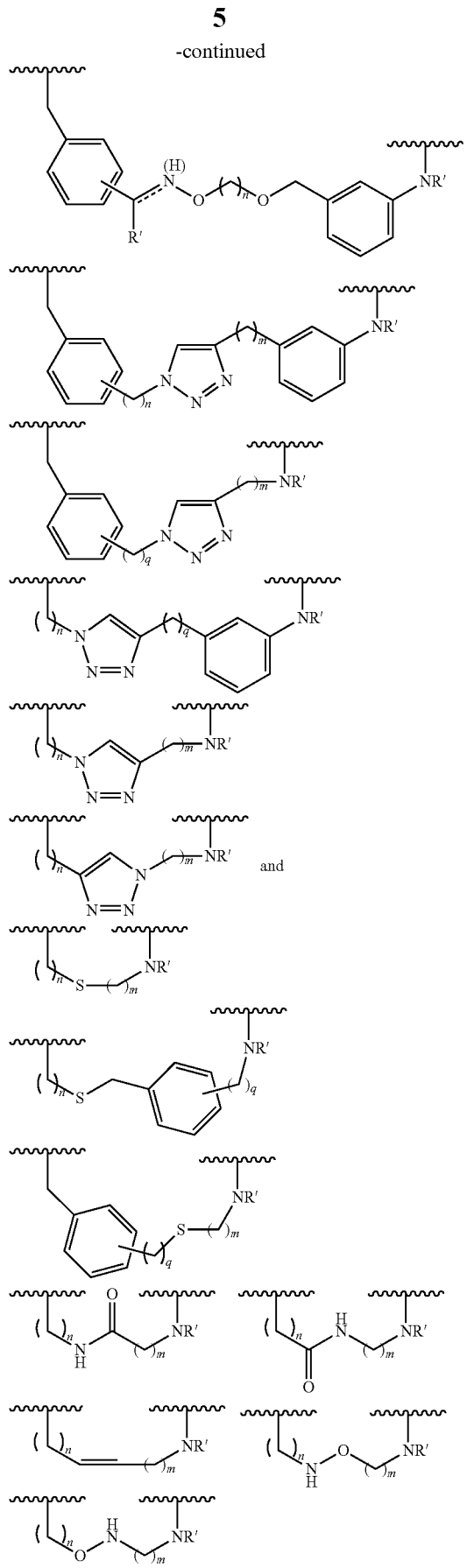

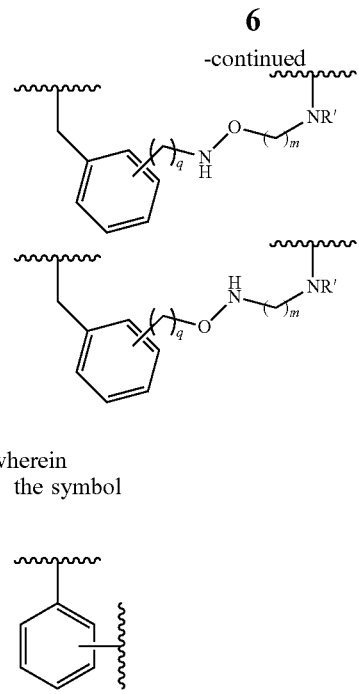

wherein
the symbol

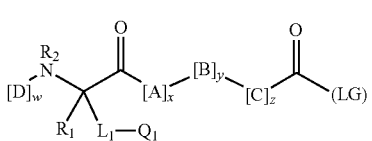

indicates an ortho-, meta- or para-disubstituted phenyl ring;

'm' and 'n' are each independently an integer number ranging from 1 to 10;

'q' is an integer number from 0 to 5; and each R' is independently —H or —CH$_3$.

Also provided is a method for synthesizing a macrocyclic peptidomimetic molecule, comprising contacting a precursor peptidomimetic molecule of Formula (IV):

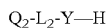

with a compound of Formula (V):

$$Q_2\text{-}L_2\text{-}Y\text{—}H \qquad (V)$$

wherein each of A, C, and D is independently a natural or non-natural amino acid;

B is a natural amino acid, non-natural amino acid, an amino acid comprising at least one additional methylene groups between the amino and carboxyl group, an amino acid comprising an amino group which is a secondary or tertiary amine, an amino acid comprising a carboxy group replaced by an ester, [—NHN(R$_3$)C(O)—], [—NH-L$_3$-SO$_2$—], or [—NH-L$_3$-];

Y is —NH—, —N(R$_4$)—, —NHN(R$_4$)—, —O—NH—, —O—, or —S—;

L$_1$, L$_2$, and L$_3$ are independently aliphatic, aryl, substituted aliphatic, substituted aryl, heteroatom-containing aliphatic, heteroatom-containing aryl, substituted heteroatom-containing aliphatic, substituted heteroatom-containing aryl groups, each being unsubstituted or substituted with R$_7$;

Q$_1$ is selected from a group consisting of sulphydryl (—SH), amino (—NHR$_5$), alkenyl (—C=CH$_2$), alkynyl (—C≡CH), azido (—N₃), keto (—C(O)R₅—), and carboxy (—C(O)OH) group;

$Q_2$ is selected from a group consisting of —CH(R₆)X, where X is F, Cl, Br, or I, amino (—NHR₆), oxyamino (—ONH₂), hydrazino (—NR₆NH₂), alkenyl (—C=CH₂), alkynyl (—C≡CH), azido (—N₃), keto (—C(O)R₆—), and carboxy (—COOH) group;

$R_1$, $R_2$, $R_3$, $R_4$, $R_5$, and $R_6$ are independently —H, aliphatic, substituted aliphatic, aryl, or substituted aryl group;

each $R_7$ is independently —H, an aliphatic, substituted aliphatic, an aryl, a substituted aryl group;

x is an integer from 0-10;
y is an integer from 0-10;
z is an integer from 0-10;
w is an integer from 1-1000;
x+y+z is at least 3;

(LG) is a group that activates the terminal carboxylic acid carbonyl group toward nucleophilic substitution;

wherein the contacting results in a covalent linkage being formed between the side-chain group, $L_1$, and the C-terminal carboxyl group of the compound of Formula (IV) via a linker moiety, and wherein the macrocyclic peptidomimetic molecule comprises an α-helix.

In one embodiment of the method, the LG group activating the C-terminal carboxylic acid group toward nucleophilic substitution is an acid chloride, an acid anhydride, an acyl azide, an O-acylisourea, a phosphonium compound, an activated ester or a thioester.

In another embodiment of the method, terminal D comprises a capping group.

In another embodiment, the method comprises expressing the precursor peptidomimetic molecule in cells prior to the contacting.

In another embodiment of the method, the LG group in the precursor peptidomimetic molecule is an intein.

In another embodiment of the method, the method is performed in solution.

In another embodiment of the method, the method is performed on a solid support.

In another embodiment, the method comprises synthesizing a library of macrocyclic peptidomimetic molecules.

In another embodiment of the method, the macrocyclic peptidomimetic molecule is a compound of Formula (I) as defined in claim 1.

In another embodiment of the method, the precursor peptidomimetic molecule comprises an amino acid analog selected from a group consisting of Group A amino acid analogs:

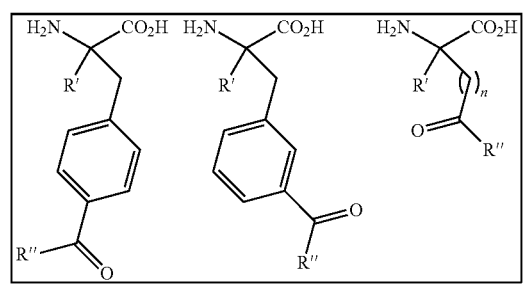

Group B amino acid analogs:

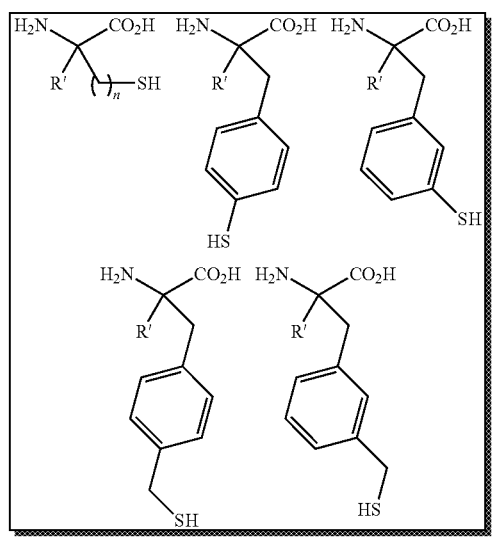

Group C amino acid analogs:

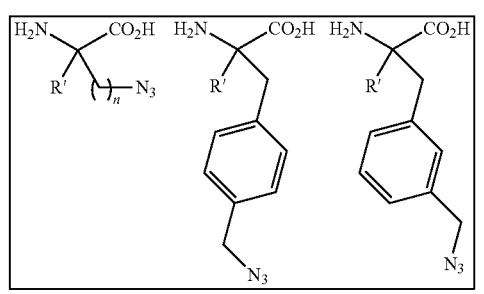

Group D amino acid analogs:

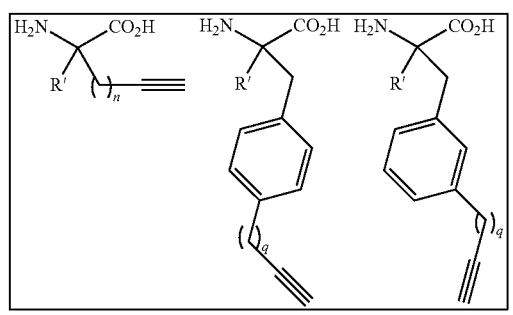

Group E amino acid analogs:

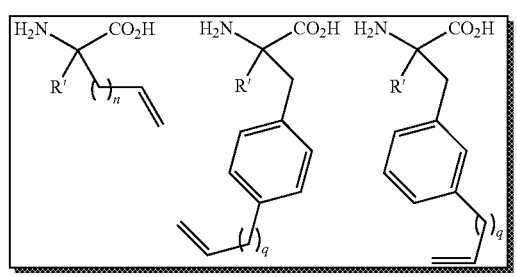

and the macrocycle-forming linker reagent of formula (V) is selected from a group of compatible macrocycle-forming linker reagents consisting of where in the selected amino acid analog and macrocycle-forming linker reagent the symbol

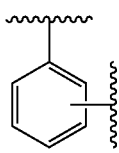

indicates an ortho-, meta- or para-disubstituted phenyl ring;

'm' and 'n' are each independently an integer number ranging from 1 to 10;

'q' is an integer number from 0 to 5;

R' is —H or —CH$_3$;

R" is —H, —CH$_3$ or —OH; and X is —Cl, —Br, —I, —OTs, —OMs, or —OTf.

Also provided is a macrocyclic peptidomimetic molecule is for use in the treatment of a p53/HDM2/HDMX-related disease in a subject, this macrocyclic peptidomimetic molecule having the structure of Formula (VII):

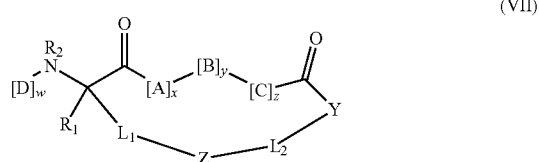

(VII)

wherein:

each A, C, and D is independently a natural or non-natural amino acid, and the terminal D optionally includes a capping group;

B is a natural amino acid, non-natural amino acid, an amino acid comprising at least one additional methylene groups between the amino and carboxyl group, an amino acid comprising an amino group which is a secondary or tertiary amine, an amino acid comprising a carboxy group replaced by an ester, [—NHN(R$_3$)C(O)—], [—NH-L$_3$-CO—], [—NH-L$_3$-SO$_2$—], or [—NH-L$_3$-];

Y is —NH—, —N(R$_4$)—, —NHN(R$_4$)—, —NH—O—, —O—, or —S—;

Z is —SCHR$_6$—, —CHR$_6$S—, —C≡C—, —N(R$_5$)CO—, —CON(R$_6$)—, —C(R$_5$)=N(R$_6$)—, —CH(R$_5$)—NH(R$_6$)—, —C(R$_5$)=N—O—, —CH(R$_5$)—NH—O—, —C(R$_5$)=N—NH(R$_6$)—, —CH(R$_5$)—NH—NH(R$_6$)—, or a triazole group;

L$_1$, L$_2$, and L$_3$ are independently aliphatic, aryl, substituted aliphatic, substituted aryl, heteroatom-containing aliphatic, heteroatom-containing aryl, substituted heteroatom-containing aliphatic, substituted heteroatom-containing aryl groups, each being unsubstituted or substituted with R$_7$;

R$_1$, R$_2$, R$_3$, R$_4$, R$_5$, and R$_6$ are independently —H, aliphatic, substituted aliphatic, aryl, or substituted aryl group;

each R$_7$ is independently —H, an aliphatic, substituted aliphatic, an aryl, and a substituted aryl group;

x is an integer from 0-10;

y is an integer from 0-10;

z is an integer from 0-10;

w is an integer from 1-1000;

x+y+z is at least 3; and wherein the macrocyclic peptidomimetic molecule comprises an amino acid sequence which is at least 50% identical to an amino acid sequence selected from a group consisting of the amino acid sequences of SEQ ID NOS. 1 through 37.

In one embodiment of the macrocyclic peptidomimetic molecule, the amino acid sequence comprised in the macrocyclic peptidomimetic molecule is at least 80%, 90%, or 95% identical to an amino acid sequence selected from a group consisting of the amino acid sequences of SEQ ID NOS. 1 through 37.

In another embodiment of the macrocyclic peptidomimetic molecule, the amino acid sequence comprised in the macrocyclic peptidomimetic molecule is an amino acid sequence selected from a group consisting of the amino acid sequences of SEQ ID NOS. 1 through 37.

In another embodiment of the macrocyclic peptidomimetic molecule, the macrocyclic peptidomimetic molecule comprises at least one α,α-disubstituted amino acid.

In another embodiment of the macrocyclic peptidomimetic molecule, the macrocyclic peptidomimetic molecule comprises at least one N-methylated amino acid.

In another embodiment of the macrocyclic peptidomimetic molecule, the macrocyclic peptidomimetic molecule comprises a fluorescent label, an affinity label, a radioisotopic label, a targeting agent, or a therapeutic agent.

In another embodiment of the macrocyclic peptidomimetic molecule, the macrocycle-forming linker [-L$_1$-Z-L$_2$-Y-] is selected from a group of macrocycle-forming linkers consisting of

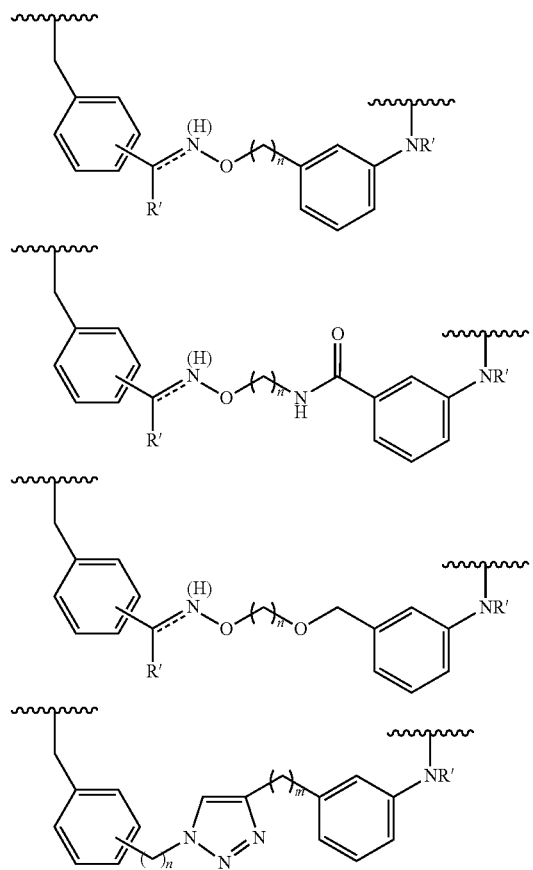

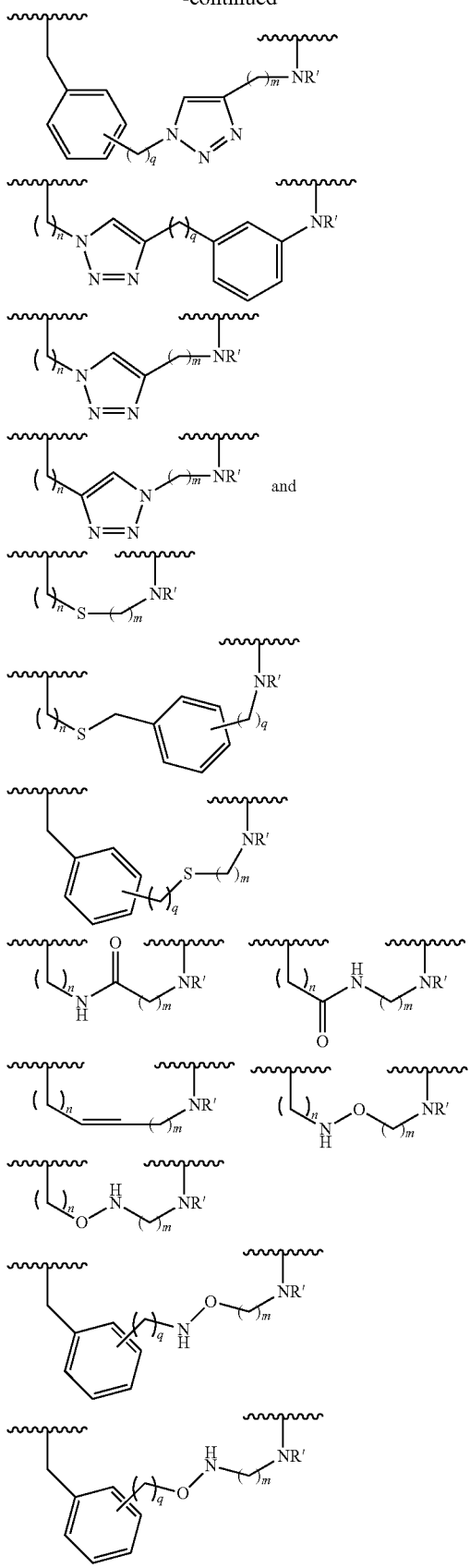

wherein
the symbol

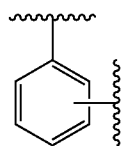

indicates an ortho-, meta- or para-disubstituted phenyl ring;

'm' and 'n' are each independently an integer number ranging from 1 to 10;

'q' is an integer number from 0 to 5; and each R' is independently —H or —CH$_3$.

In another embodiment of the macrocyclic peptidomimetic molecule, the amino acid sequence comprised in the p53 macrocyclic peptidomimetic molecule is at least about 50% identical to the polypeptide sequences corresponding to SEQ ID NOS: 1 through 37, and the side-chain-to-C-terminus macrocyclization is mediated by an amino acid analog selected from a group of amino acid analogs consisting of Group A amino acid analogs:

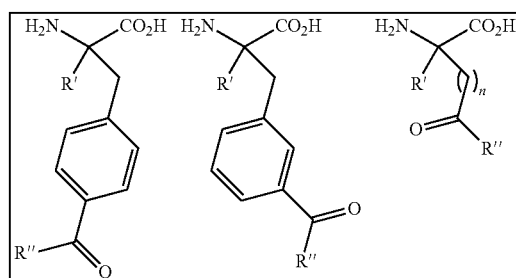

Group B amino acid analogs:

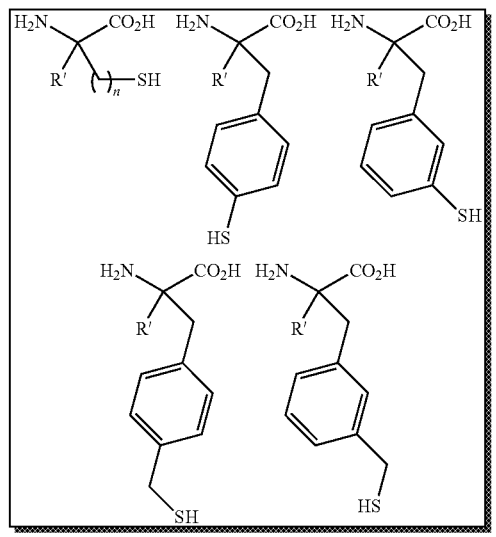

Group C amino acid analogs:

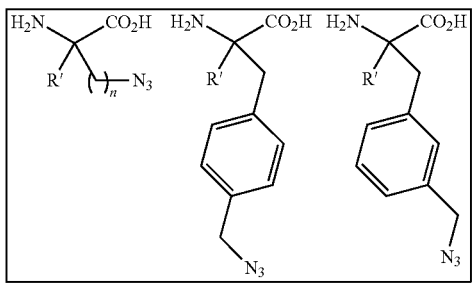

Group D amino acid analogs:

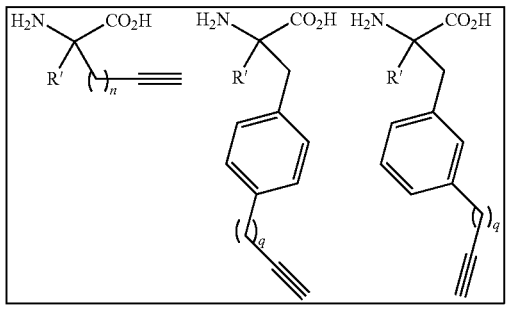

Group E amino acid analogs:

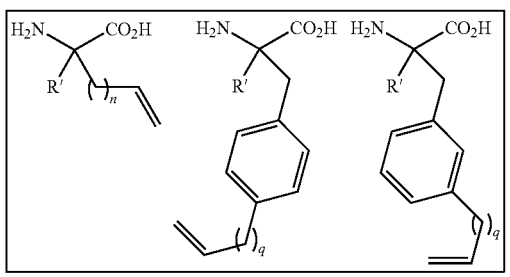

and by a compatible macrocycle-forming linker reagent selected from a group of macrocycle-forming linker reagents consisting of Group A macrocycle-forming linker reagents:

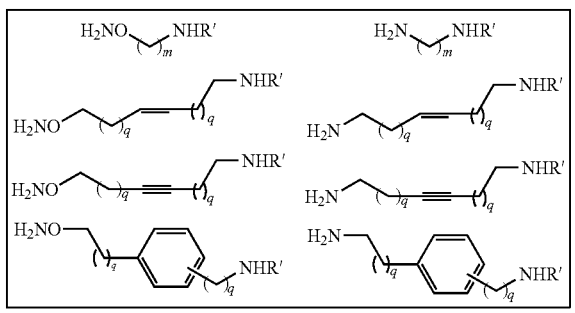

Group B macrocycle-forming linker reagents:

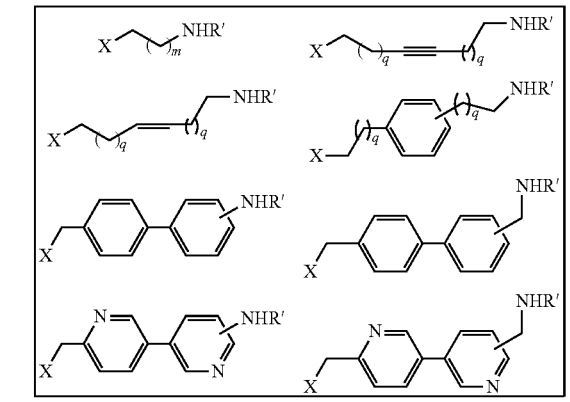

Group C macrocycle-forming reagents:

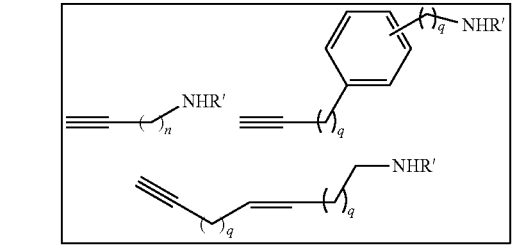

Group D macrocycle-forming reagents:

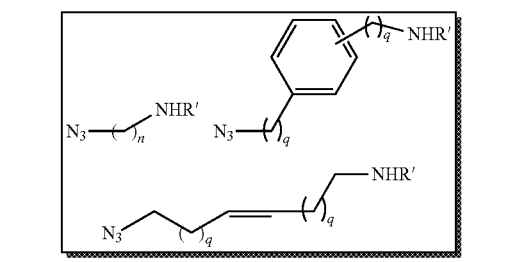

Group E macrocycle-forming reagents:

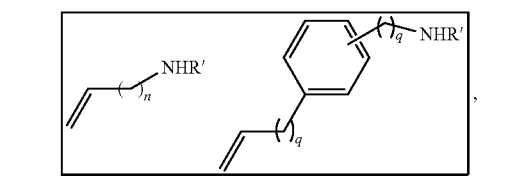

where in the selected amino acid analog and macrocycle-forming linker reagent, the symbol

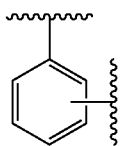

indicates an ortho-, meta- or para-disubstituted phenyl ring;
'm' and 'n' are independently an integer number ranging from 1 to 10;
'q' is an integer number from 0 to 5;
each R' is independently —H or —CH$_3$;
R" is —H, —CH$_3$ or —OH; and
X is —Cl, —Br, —I, —OTs, —OMs, or —OTf.

In another embodiment of the macrocyclic peptidomimetic molecule, the p53/HDM2/HDMX-related disease is a cancer or a neoplastic disease.

In another embodiment of the macrocyclic peptidomimetic molecule, the p53/HDM2/HDMX-related disease is sarcoma, gastric cancer, esophageal cancer, rectal cancer, pancreatic cancer, ovarian cancer, prostate cancer, uterine cancer, skin cancer, brain cancer, carcinoma, cervical cancer, testicular cancer, lung cancer, bladder cancer, leukemia, or lymphoma.

In another embodiment of the macrocyclic peptidomimetic molecule, the p53/HDM2/HDMX-related disease is an inflammatory, a neurodegenerative, or an autoimmune disease.

Also provided is method for treating (or ameliorating) a p53/HDM2/HDMX-related disease in a subject, comprising:
administering to a subject to be treated (e.g., suffering from a p53/HDM2/HDMX-related disease) a macrocyclic peptidomimetic molecule having the structure of Formula (VII):

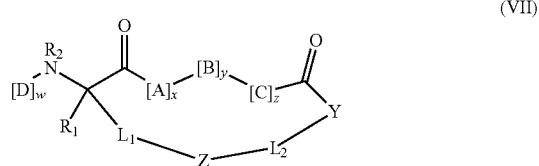

(VII)

wherein:
each A, C, and D is independently a natural or non-natural amino acid, and the terminal D optionally includes a capping group;
B is a natural amino acid, non-natural amino acid, an amino acid comprising at least one additional methylene groups between the amino and carboxyl group, an amino acid comprising an amino group which is a secondary or tertiary amine, an amino acid comprising a carboxy group replaced by an ester, [—NHN($R_3$)C(O)—], [—NH-$L_3$-CO—], [—NH-$L_3$-$SO_2$—], or [—NH-$L_3$-];
Y is —NH—, —N($R_4$)—, —NHN($R_4$)—, —NH—O—, —O—, or —S—;
Z is —SCH$R_6$—, —CH$R_6$S—, —C≡C—, —N($R_5$)CO—, —CON($R_6$)—, —C($R_5$)=N($R_6$)—, —CH($R_5$)—NH($R_6$)—, —C($R_5$)=N—O—, —CH($R_5$)—NH—O—, —C($R_5$)=N—NH($R_6$)—, —CH($R_5$)—NH—NH($R_6$)—, or a triazole group;
$L_1$, $L_2$, and $L_3$ are independently aliphatic, aryl, substituted aliphatic, substituted aryl, heteroatom-containing aliphatic, heteroatom-containing aryl, substituted heteroatom-containing aliphatic, substituted heteroatom-containing aryl groups, each being unsubstituted or substituted with $R_7$;
$R_1$, $R_2$, $R_3$, $R_4$, $R_5$, and $R_6$ are independently —H, aliphatic, substituted aliphatic, aryl, or substituted aryl group;
each $R_7$ is independently —H, an aliphatic, substituted aliphatic, an aryl, and a substituted aryl group;
x is an integer from 0-10;
y is an integer from 0-10;
z is an integer from 0-10;
w is an integer from 1-1000;
x+y+z is at least 3; and
wherein the macrocyclic peptidomimetic molecule comprises an amino acid sequence which is at least 50% identical to an amino acid sequence selected from a group consisting of the amino acid sequences of SEQ ID NOS. 1 through 37.

In one embodiment of the method, the amino acid sequence comprised in the macrocyclic peptidomimetic molecule is at least 80%, 90%, or 95% identical to an amino acid sequence selected from a group consisting of the amino acid sequences of SEQ ID NOS. 1 through 37.

In another embodiment of the method, the amino acid sequence comprised in the macrocyclic peptidomimetic molecule is an amino acid sequence selected from a group consisting of the amino acid sequences of SEQ ID NOS. 1 through 37.

In another embodiment of the method, the macrocyclic peptidomimetic molecule comprises at least one α,α-disubstituted amino acid.

In another embodiment of the method, the macrocyclic peptidomimetic molecule comprises at least one N-methylated amino acid.

In another embodiment of the method, the e macrocyclic peptidomimetic molecule comprises a fluorescent label, an affinity label, a radioisotopic label, a targeting agent, or a therapeutic agent.

In another embodiment of the method, the macrocycle-forming linker [-$L_1$-Z-$L_2$-Y-] is selected from a group of macrocycle-forming linkers consisting of

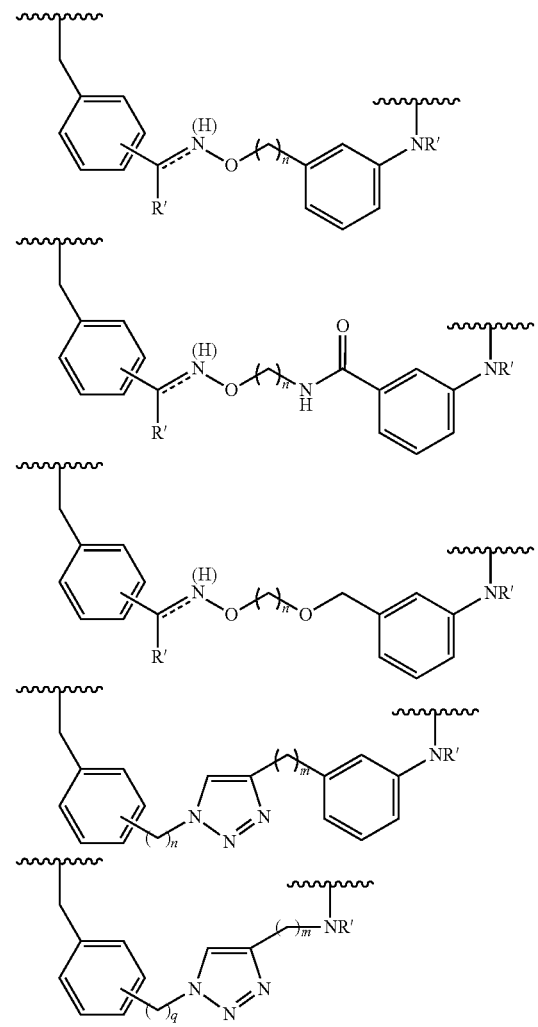

-continued

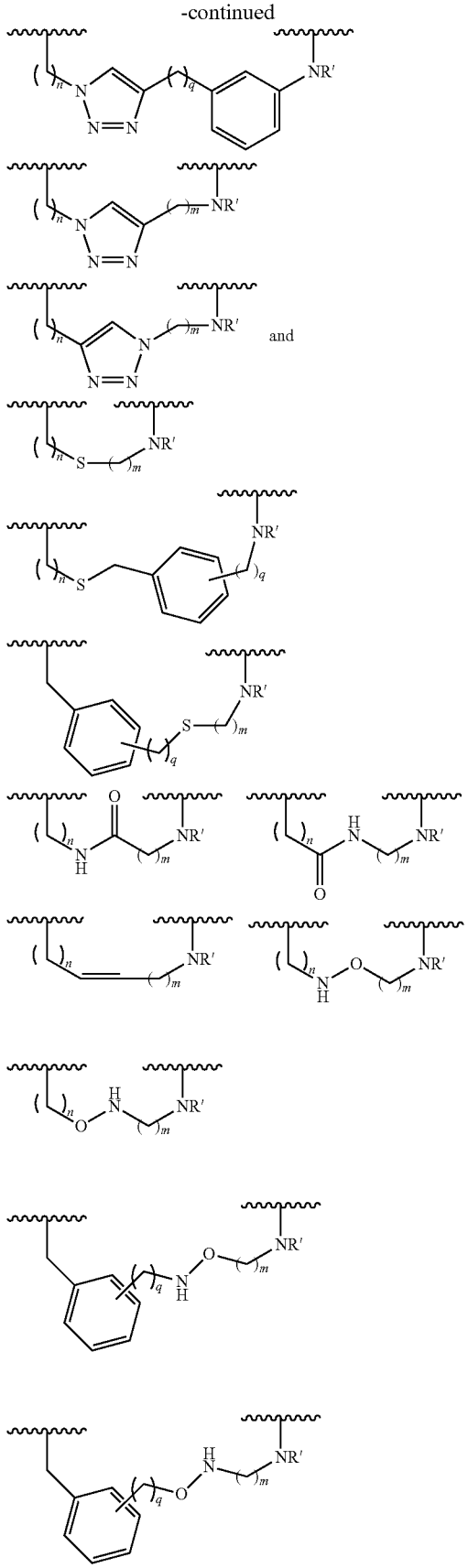

wherein
the symbol

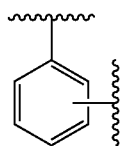

indicates an ortho-, meta- or para-disubstituted phenyl ring;

'm' and 'n' are each independently an integer number ranging from 1 to 10;

'q' is an integer number from 0 to 5; and each R' is independently —H or —CH$_3$.

In another embodiment of the method, the amino acid sequence comprised in the p53 macrocyclic peptidomimetic molecule is at least about 50% identical to the polypeptide sequences corresponding to SEQ ID NOS: 1 through 37, and the side-chain-to-C-terminus macrocyclization is mediated by an amino acid analog selected from a group of amino acid analogs consisting of Group A amino acid analogs:

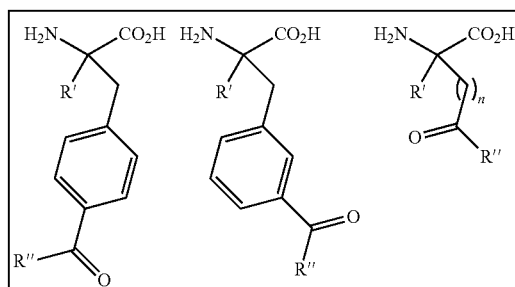

Group B amino acid analogs:

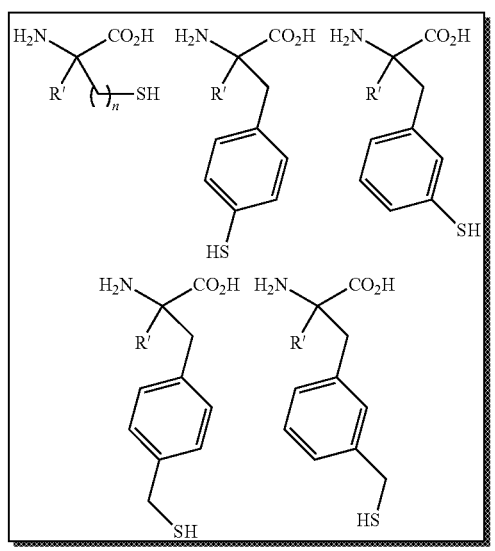

Group C amino acid analogs:

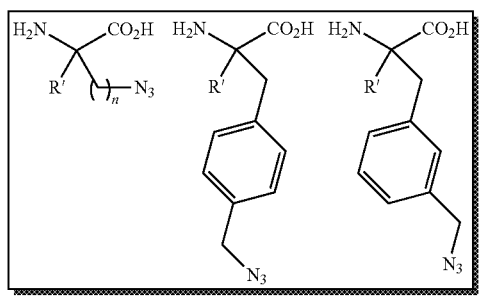

Group D amino acid analogs:

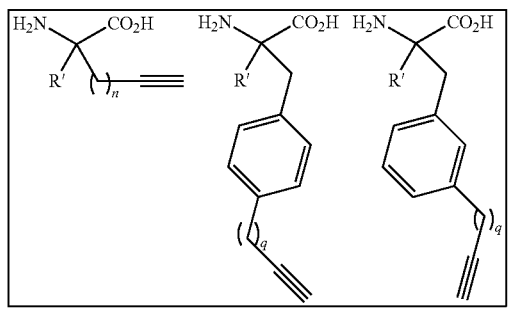

Group E amino acid analogs:

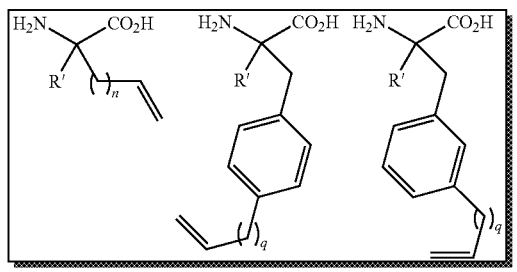

and by a compatible macrocycle-forming linker reagent selected from a group of macrocycle-forming linker reagents consisting of Group A macrocycle-forming linker reagents:

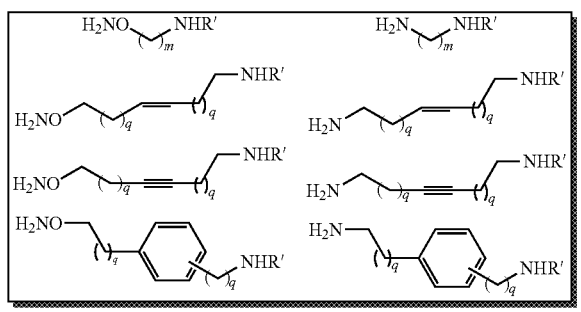

Group B macrocycle-forming linker reagents:

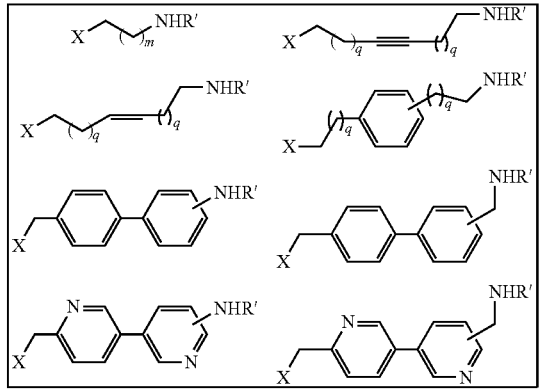

Group C macrocycle-forming reagents:

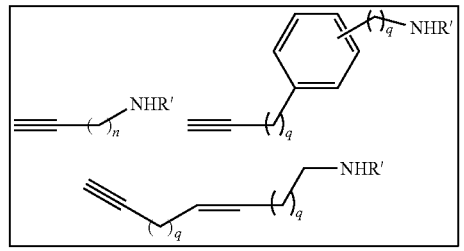

Group D macrocycle-forming reagents:

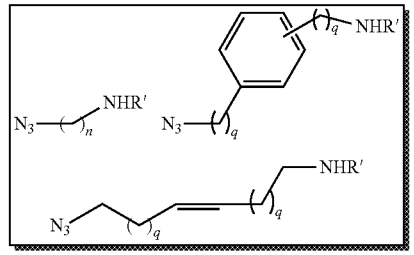

Group E macrocycle-forming reagents:

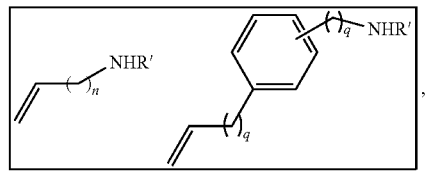

where in the selected amino acid analog and macrocycle-forming linker reagent, the symbol

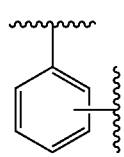

indicates an ortho-, meta- or para-disubstituted phenyl ring;
'm' and 'n' are independently an integer number ranging from 1 to 10;
'q' is an integer number from 0 to 5;
each R' is independently —H or —CH$_3$;
R" is —H, —CH$_3$ or —OH; and
X is —Cl, —Br, —I, —OTs, —OMs, or —OTf.

In another embodiment of the method, the p53/HDM2/HDMX-related disease is a cancer or a neoplastic disease.

In another embodiment of the method, the p53/HDM2/HDMX-related disease is sarcoma, gastric cancer, esophageal cancer, rectal cancer, pancreatic cancer, ovarian cancer, prostate cancer, uterine cancer, skin cancer, brain cancer, carcinoma, cervical cancer, testicular cancer, lung cancer, bladder cancer, leukemia, or lymphoma.

In another embodiment of the method, the p53/HDM2/HDMX-related disease is an inflammatory, a neurodegenerative, or an autoimmune disease.

4. BRIEF DESCRIPTION OF THE DRAWINGS

FIG. 1. General scheme illustrating the design and preparation of macrocyclic peptidomimetics of α-helical motifs according to the methods described herein. A target α-helical recognition motif is first identified, for example, based on the crystal structure of a protein-protein or protein-peptide complex of interest. The macrocyclic peptidomimetic molecule is then generated via side-chain-to-C-terminus cyclization of a polypeptide sequence derived from such α-helical binding motif. Optimization of the peptidomimetic molecule in terms of binding affinity to the protein partner, inhibitory potency, alpha-helicity, proteolytic stability, and/or cell permeability can be achieved through variation of the amino acid sequence, linker structure, and side-chain-to-C-terminus connectivity. $FG_1$ and $FG_2$ are functional group capable of reacting with each other to form a covalent bond; NuH: nucleophilic group; Act: nucleophilic substitution-activating group.

Figure 2:
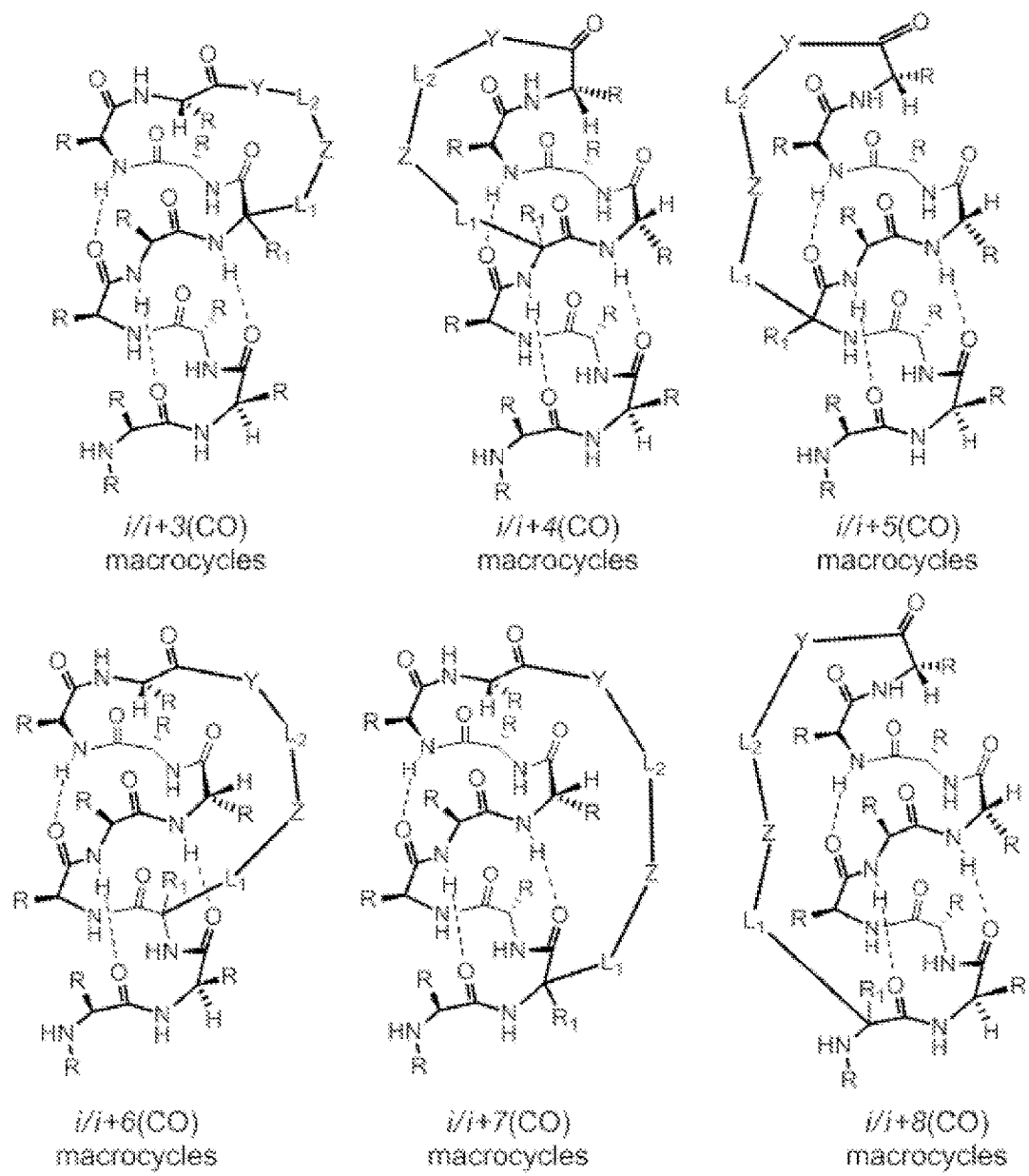

FIG. 2. Representative structures of macrocyclic peptidomimetic molecules disclosed herein. In particular, the figure illustrates representative macrocyclic peptidomimetics that comprise polypeptide sequences composed of L-α-amino acids and side-chain-to-C-terminus connectivities ranging from i/i+3(CO) (i.e., residue 'i' is connected to the carbonyl group of residue 'i+3' via a macrocycle-forming linker) to i/i+8(CO). Multiple variants of these molecules can be envisioned and prepared according to the methods described herein.

Figure 3:
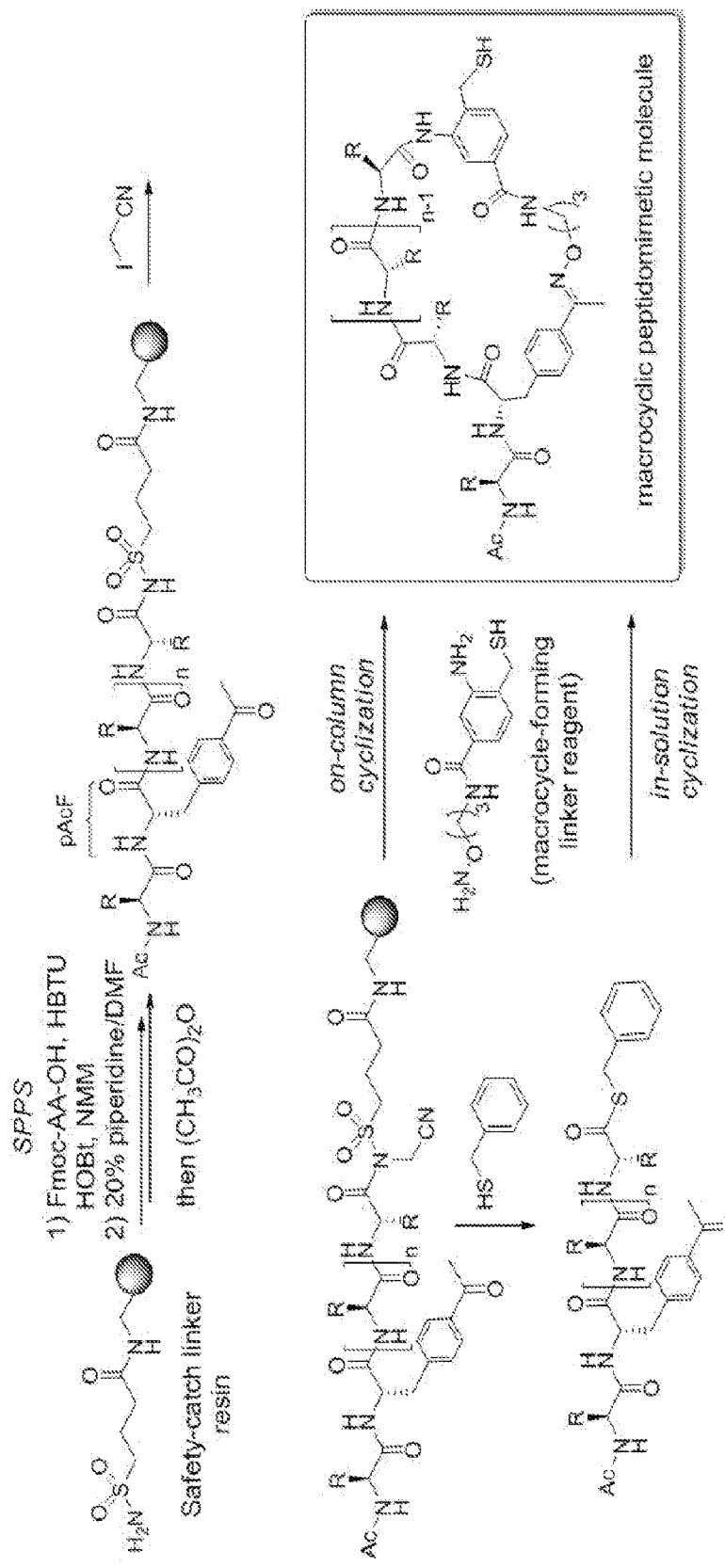

FIG. 3. The scheme describes a representative synthetic method for the preparation of the macrocyclic peptidomimetic molecules disclosed herein. In this example, 3-amino-N-(3-(aminooxy)propyl)-4-(mercaptomethyl)benzamide (SP8) serves as the macrocycle-forming linker reagent and L-para-acetyl-phenylalanine (pAcF) serves as the amino acid analog of general formula (VI). Briefly, the acyclic precursor peptidomimetic molecule is prepared by solid-phase peptide synthesis (SPPS). After alkylation of the safety catch linker, macrocyclization is afforded upon reaction of the macrocycle-forming linker reagent with the resin-tethered precursor molecule ("on-resin cyclization"). Alternatively, the acyclic precursor molecule is first cleaved from the resin as a thioester and then cyclized in solution upon reaction with the macrocycle-forming linker reagent ("in-solution cyclization"). In this specific example, the thiol group comprised within the macrocycle-forming linker serves the dual role of facilitating the C-terminus ligation reaction and providing a convenient handle for immobilization or further functionalization of the macrocycle with a fluorescent dye, affinity tag, or other molecules.

Figure 4:
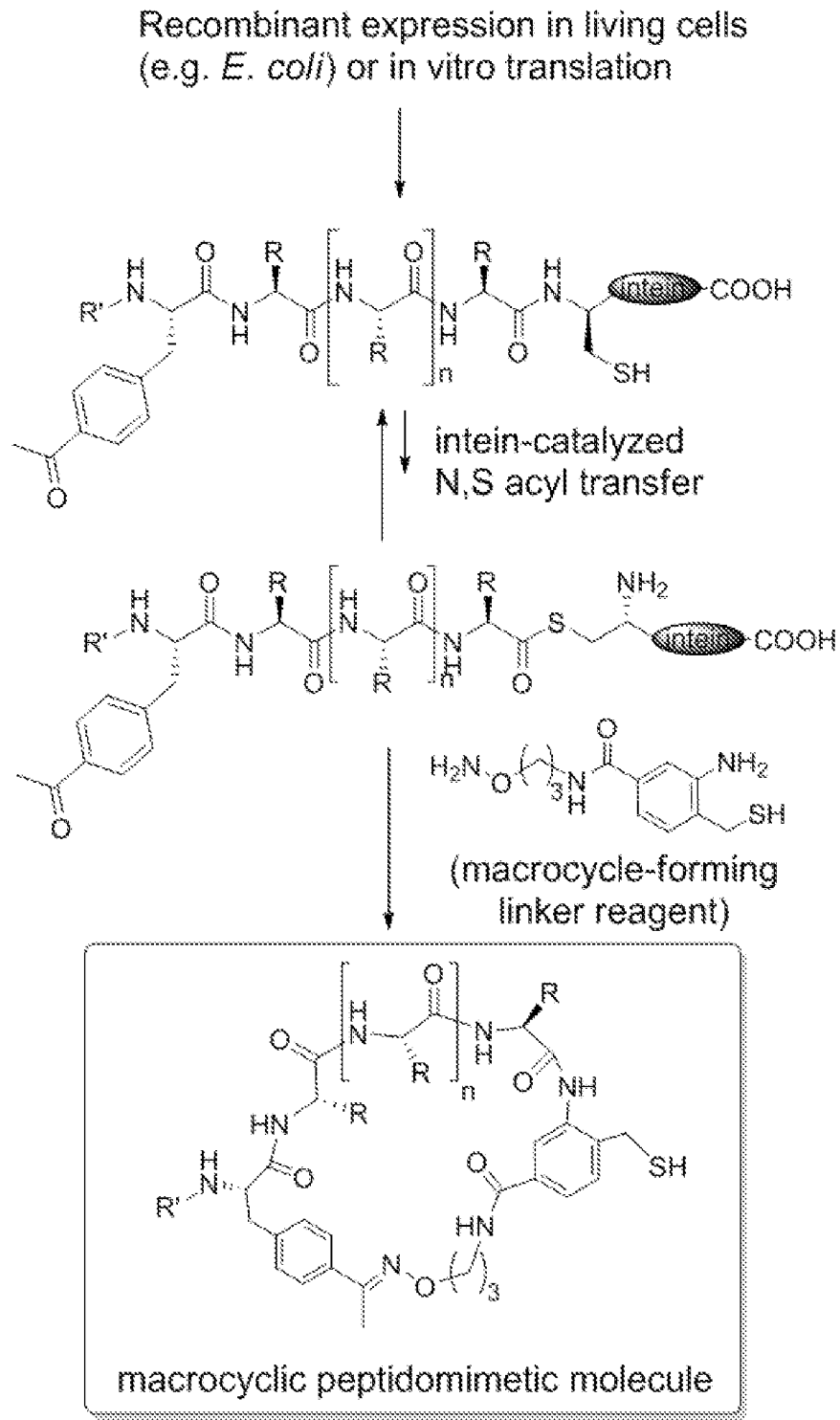

FIG. 4. Alternative chemobiosynthetic method for the preparation of the macrocyclic peptidomimetic molecules disclosed herein. In this case, the acyclic precursor polypeptide molecule is produced by ribosomal expression in a host (e.g., *Escherichia coli*), wherein an amino acid analog of general formula (VI) such as L-para-acetyl-phenylalanine is introduced via amber stop codon suppression and the C-terminus of the polypeptide is activated through fusion with an intein protein. Cyclization is achieved by reaction of the precursor polypeptide with an appropriate macrocycle-forming linker reagent such as, for example, 3-amino-N-(3-(aminooxy)propyl)-4-(mercaptomethyl)benzamide) (SP8), resulting in the desired macrocyclic peptidomimetic molecule.

FIGS. 5A-5D. Synthesis of amino acid analogs. (A) Synthetic route for preparation of enantiopure N-Fmoc protected L- and D-para-acetyl-phenylalanine. (B) Synthetic route for preparation of alkyne-functionalized amino acid, O-propargyl-tyrosine. (C) Synthetic route for preparation of thiol-functionalized amino acid, AmmF (D) Synthetic route for preparation of thiol-functionalized amino acid, MeF.

Figure 6:
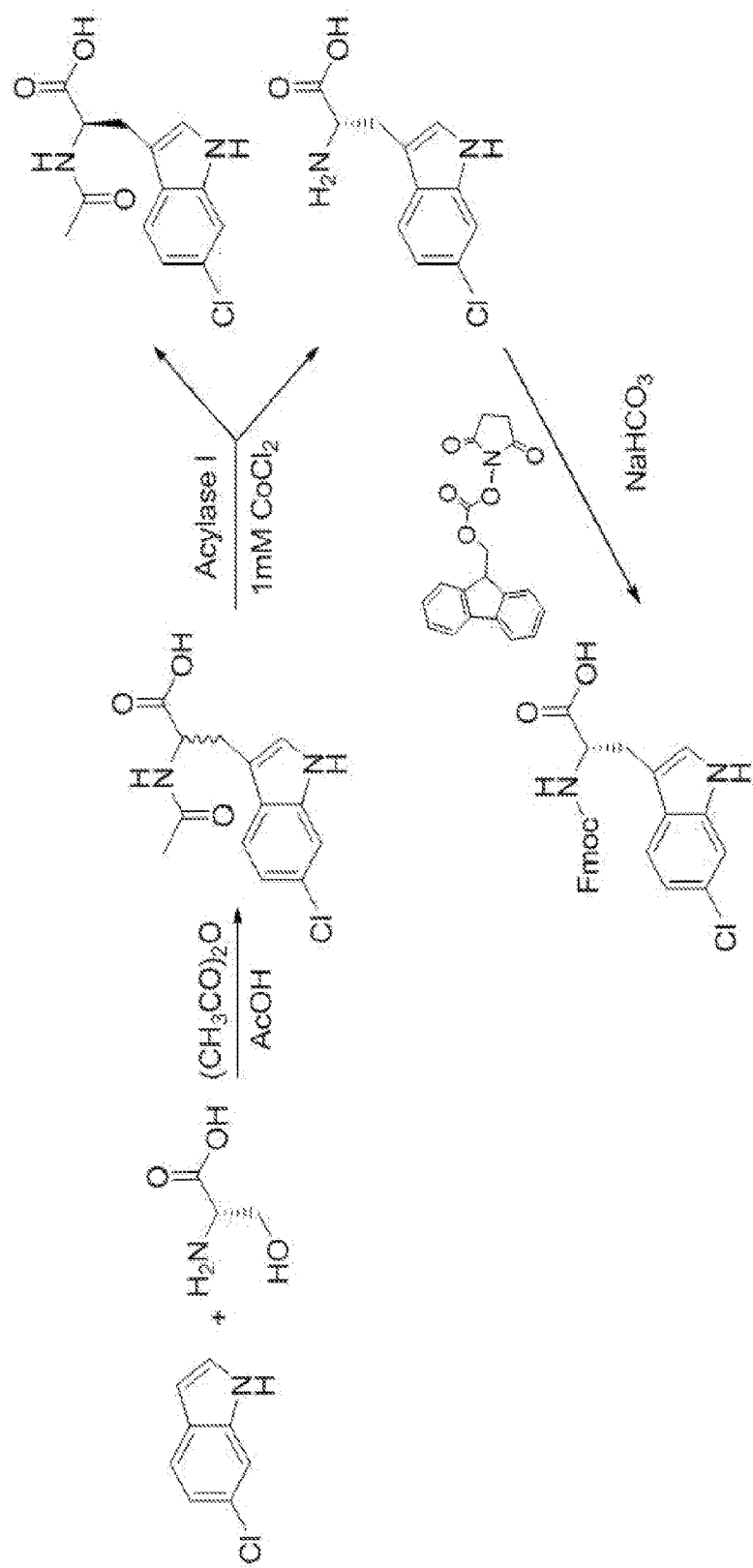

FIG. 6. Synthetic route for preparation of enantiopure N-Fmoc protected 6-chloro-tryptophan (6Cl-Trp).

Figure 7:
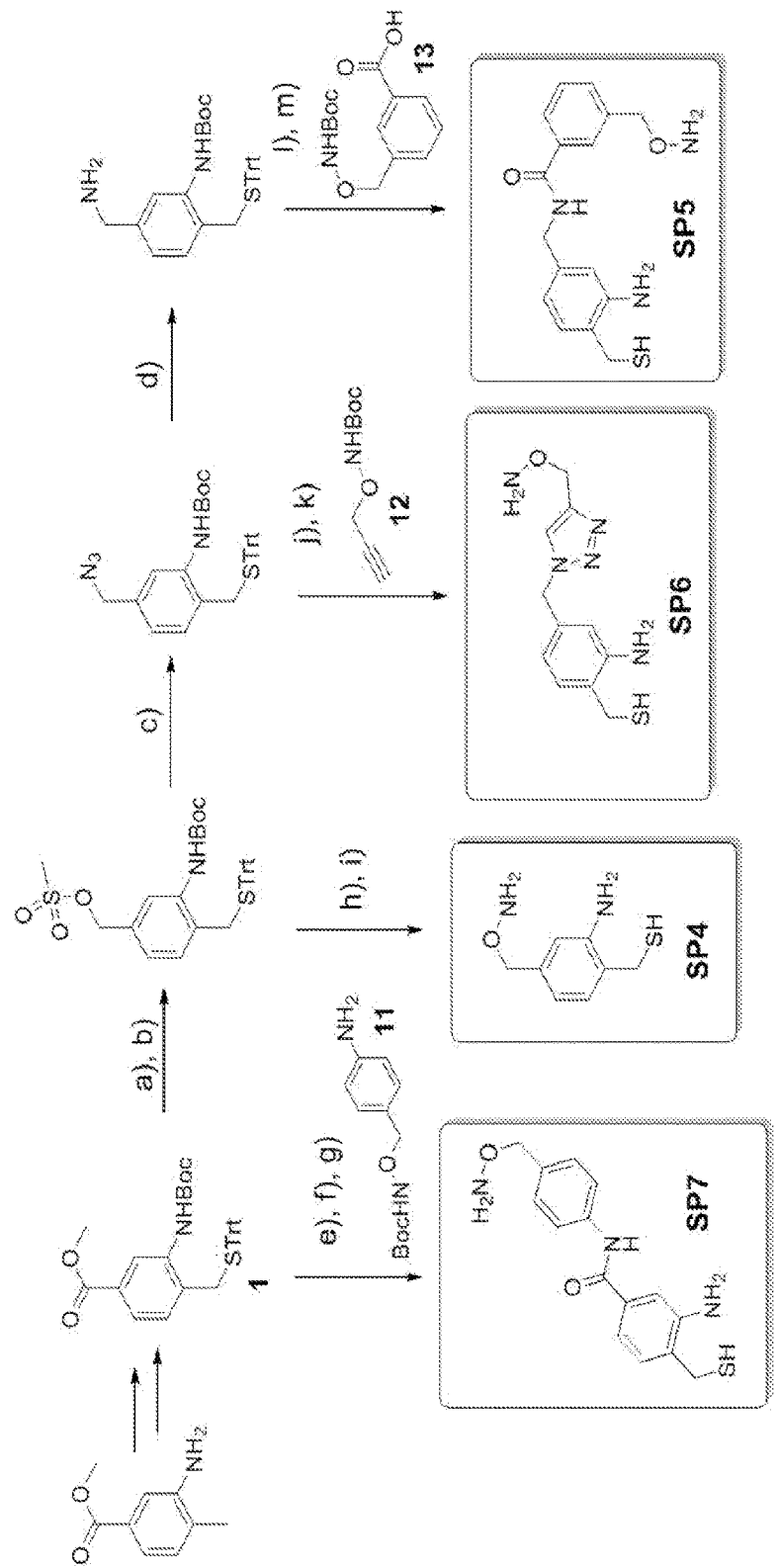

FIG. 7. Synthetic routes for preparation of macrocycle-forming reagents SP4, SP5, SP6, and SP7. Reagents and conditions: a) $LiAlH_4$, THF; 95%; b) Ms-Cl, DIPEA, $CH_2Cl_2$; 88%; c) $NaN_3$, DMF; 100%; d) $LiAlH_4$, THF; 95%; e) LiOH, THF:$H_2O$; 100%; f) 11, DCC, DMAP, $CH_2Cl_2$; 26%; g) TIPS, TFA, $CH_2Cl_2$; 100%; h) HONHBoc, DBU, DMF; 89%; i) TIPS, TFA, $CH_2Cl_2$; 100%; j) 12, $CuSO_4$, NaAsc, $CH_2Cl_2$: $H_2O$; 72%; k) TIPS, TFA, $CH_2Cl_2$; 100%; l) 13, HBTU, DIPEA, $CH_2Cl_2$; 55%; m) TIPS, TFA, $CH_2Cl_2$; 100%.

Figure 8:
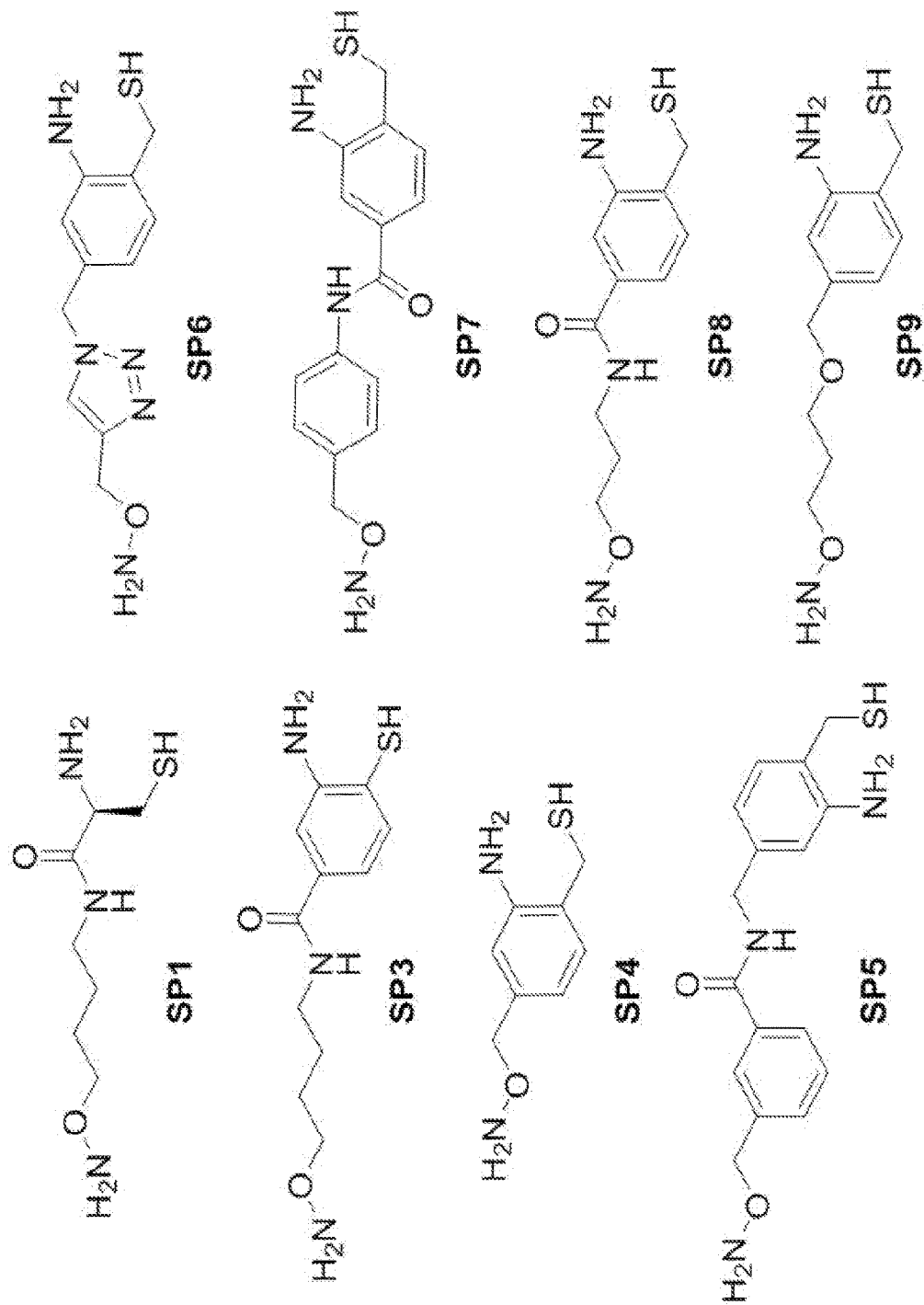

FIG. 8. Representative structures of macrocycle-forming linker reagents for use in the methods described herein.

FIGS. 9A-9B. (A) Crystal structure of HDM2 bound to the p53-related peptide PMI (pdb 3EQS). (B) Model of p53 macrocyclic peptidomimetic P8 (SEQ ID NO. 39) (FIG. 10).

FIG. 10. Amino acid sequence, structure, and inhibitory activity of selected p53 macrocyclic peptidomimetics and reference linear peptides. The inhibitory activities refer to $IC_{50}$ values for disruption of $p53_{(15-29)}$-HDM2 interaction or $p53_{(15-29)}$-HDMX interaction as determined using a Surface Plasmon Resonance-based inhibition assay.

Figure 11A:
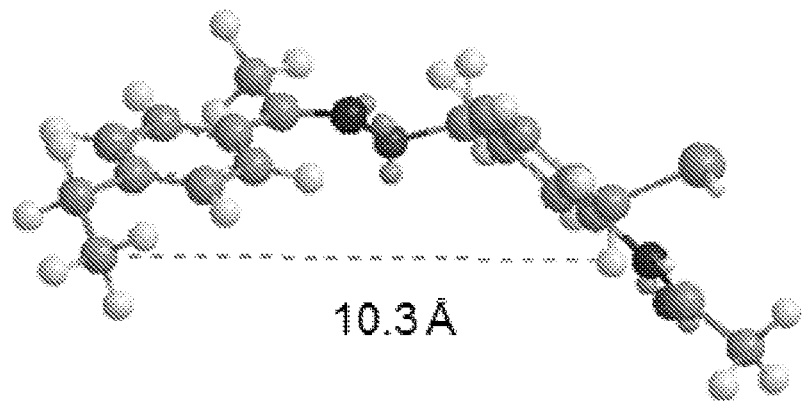
Figure 11B:
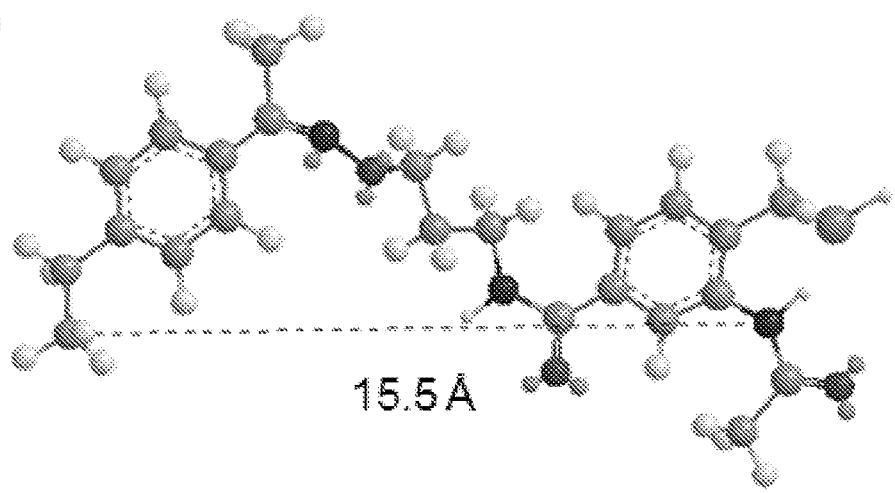
Figure 11C:
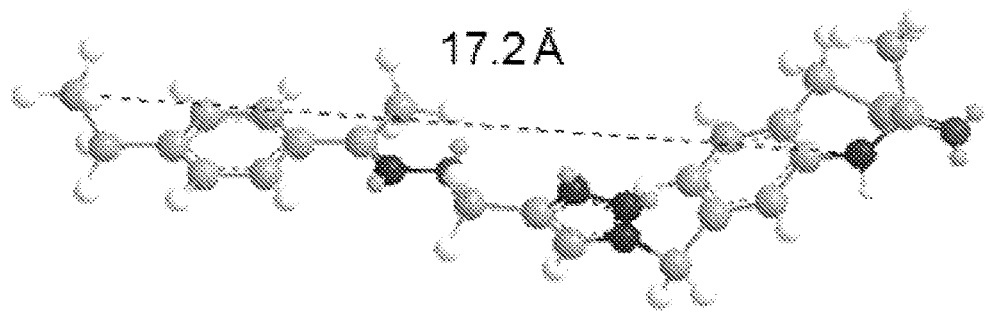

FIGS. 11A-11C. Energy-minimized models of the macrocycle-forming linkers generated from the reaction of para-acetyl-phenylalanine (=mimicked by 4-ethyl-acetophenone moiety) with macrocycle-forming linker reagents SP4 (A), SP8 (B), and SP6 (C). The near-maximal spanning distances between the side-chain and C-terminus ligation points are indicated.

Figure 12A:
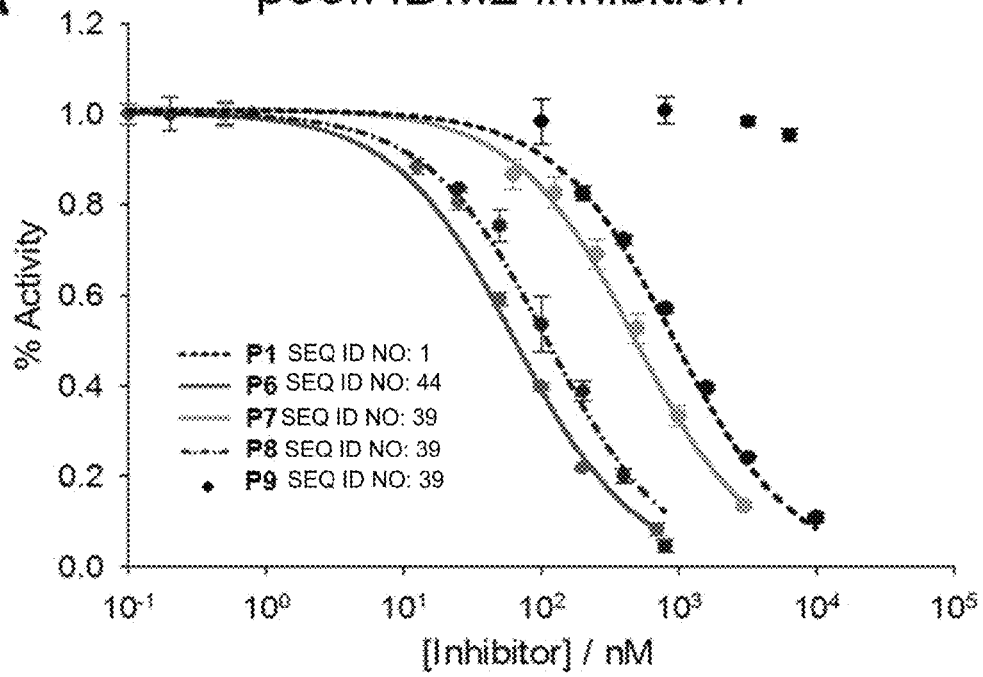
Figure 12B:
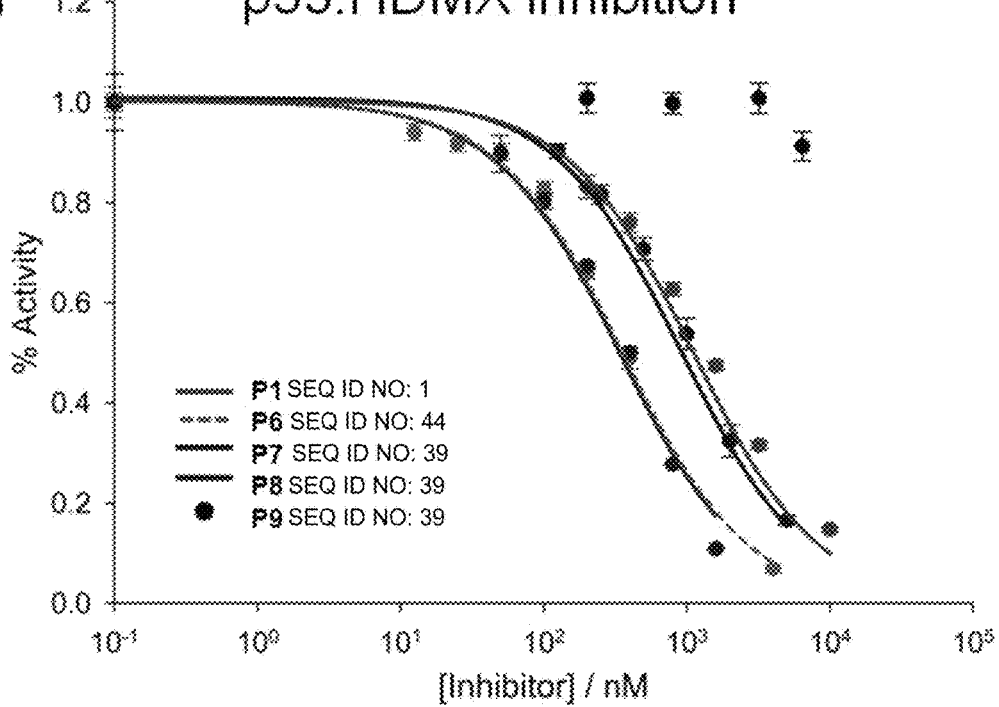

FIGS. 12A-12B. Concentration dependent curves for inhibition of (A) p53-HDM2 interaction and (B) p53-HDMX interaction, by selected p53 macrocylic peptidomimetics and reference linear peptides. Data were obtained using a Surface Plasmon Resonance-based inhibition assay, in which binding of soluble HDM2/X to immobilized biotin-conjugated p53 peptide (biot-$p53_{15-29}$) is inhibited with increasing amounts of the compound.

Figures 13A, 13B:
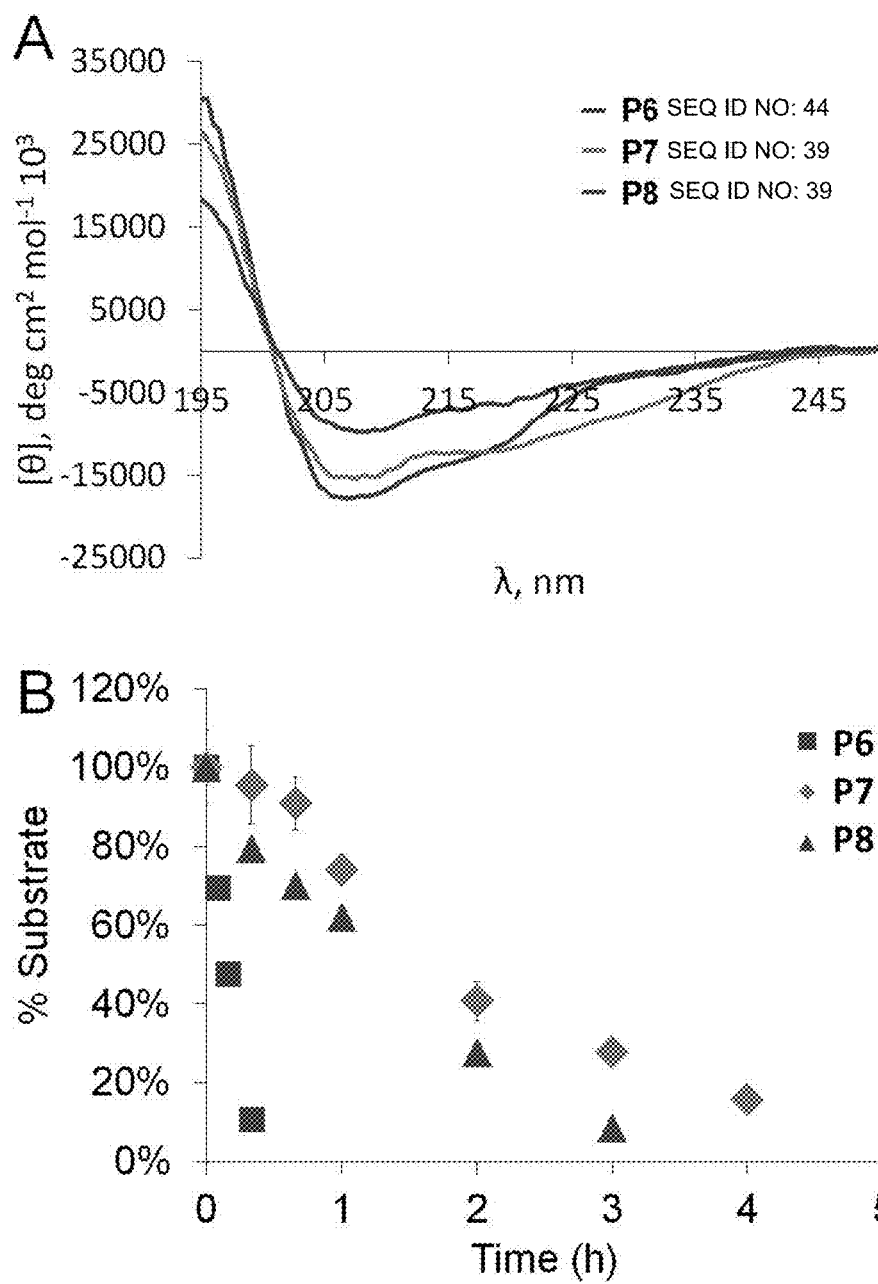

FIGS. 13A-13B. α-Helicity and proteolytic stability. (A) Circular dichroism spectra of representative p53 macrocyclic peptidomimetics (P7 (SEQ ID NO. 39) and P8 (SEQ ID NO. 39)) and reference linear peptide (P6 (SEQ ID NO. 44)) as measured in phosphate buffer (pH 7.0) and 40% TFE. (B) Proteolytic stability tests of the same compounds in the presence of chymotrypsin (1.0 µg/mL) at 37° C. The graph illustrates the residual amount of the compound after incubation with chymotrypsin at varying time points.

FIGS. 14A-14B. Confocal fluorescent microscopy image of HEK293 cells treated with (A) fluorescein-labeled linear p53-derived peptide P1 (SEQ ID NO. 1) and (B) fluorescein-labeled p53 macrocyclic peptidomimetic compound P8

(SEQ ID NO. 39). Blue=DAPI nuclear stain; Green=fluorescein-conjugated compound.

Figure 15:
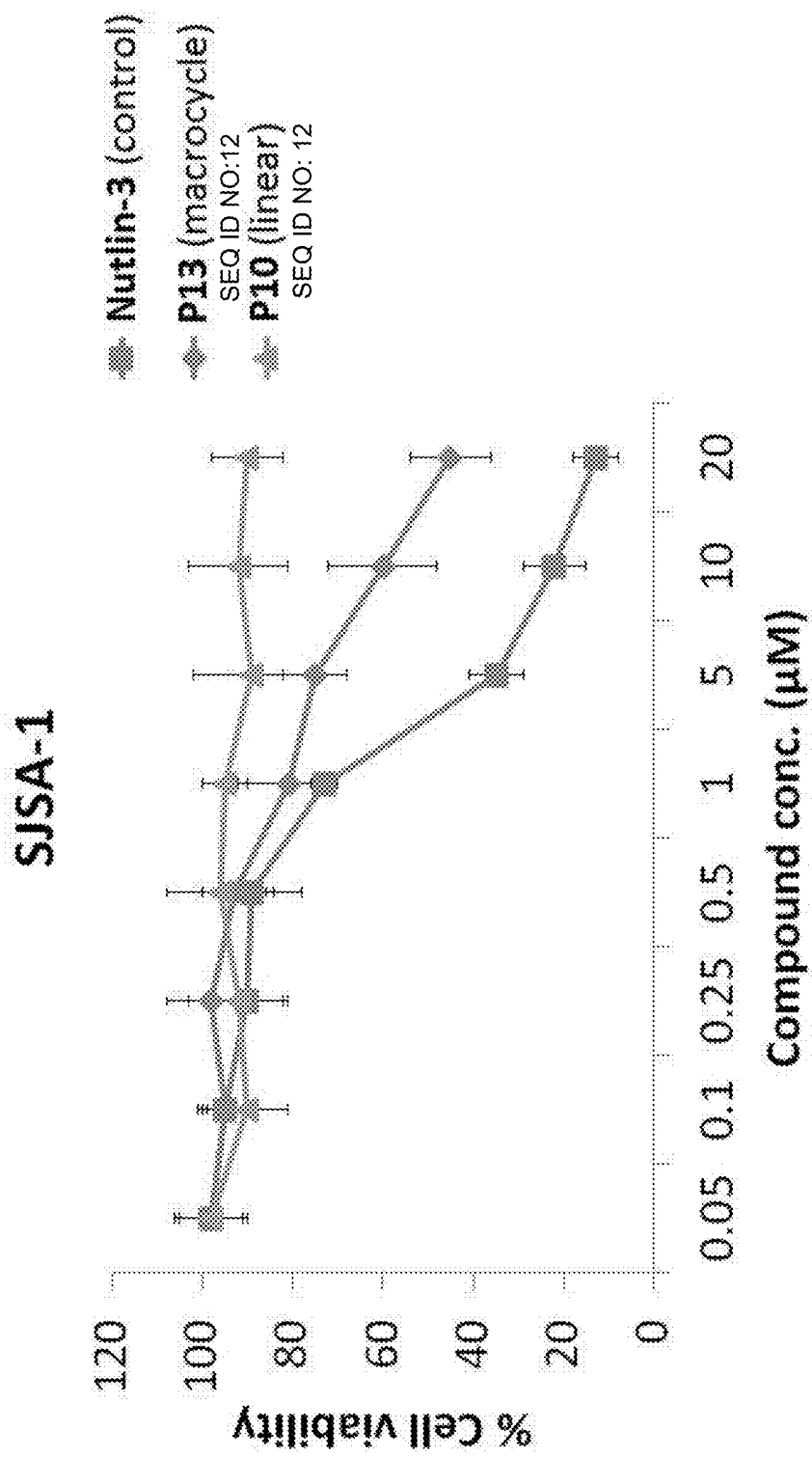

FIG. 15. Cell viability of SJSA-1 cells (HDM2-overexpressing osteosarcoma cells) following treatment with p53 macrocylic peptidomimetic P13 (SEQ ID NO. 12) and the corresponding acylic peptide P10 (SEQ ID NO. 12). The dose-response curve for nutlin-3, a known small-molecule HDM2 inhibitor, is also shown.

Figure 16:
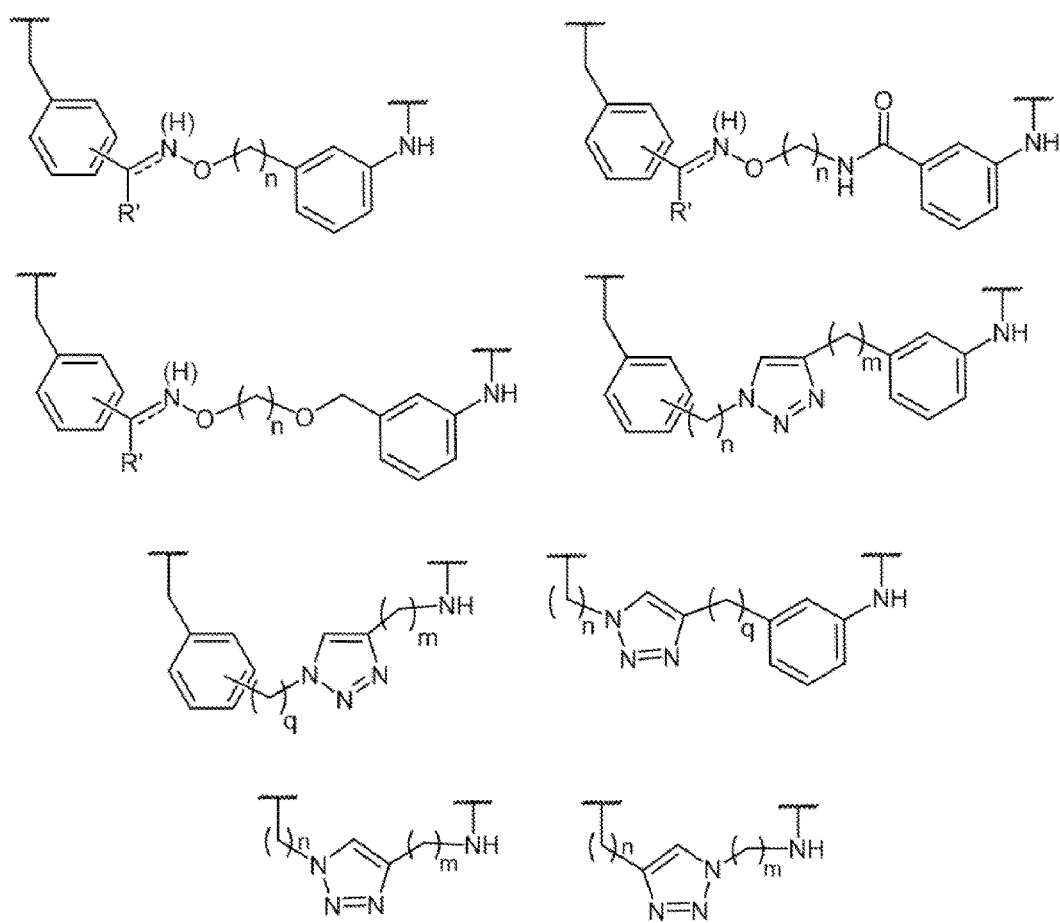

FIG. 16. Structures of macrocycle-forming linkers of formula [-L$_1$-Z-L$_2$-Y-] that can be used in the methods described herein. The symbol "C⋯N" indicates a single or double bond. The symbol

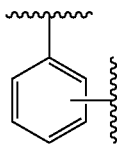

indicates an ortho-, meta- or para-disubstituted phenyl ring. R' is —H or —CH$_3$. The symbols 'm' and 'n' are integer numbers from 1 to 10; 'q' is an integer number from 0 to 5.

Figure 17:
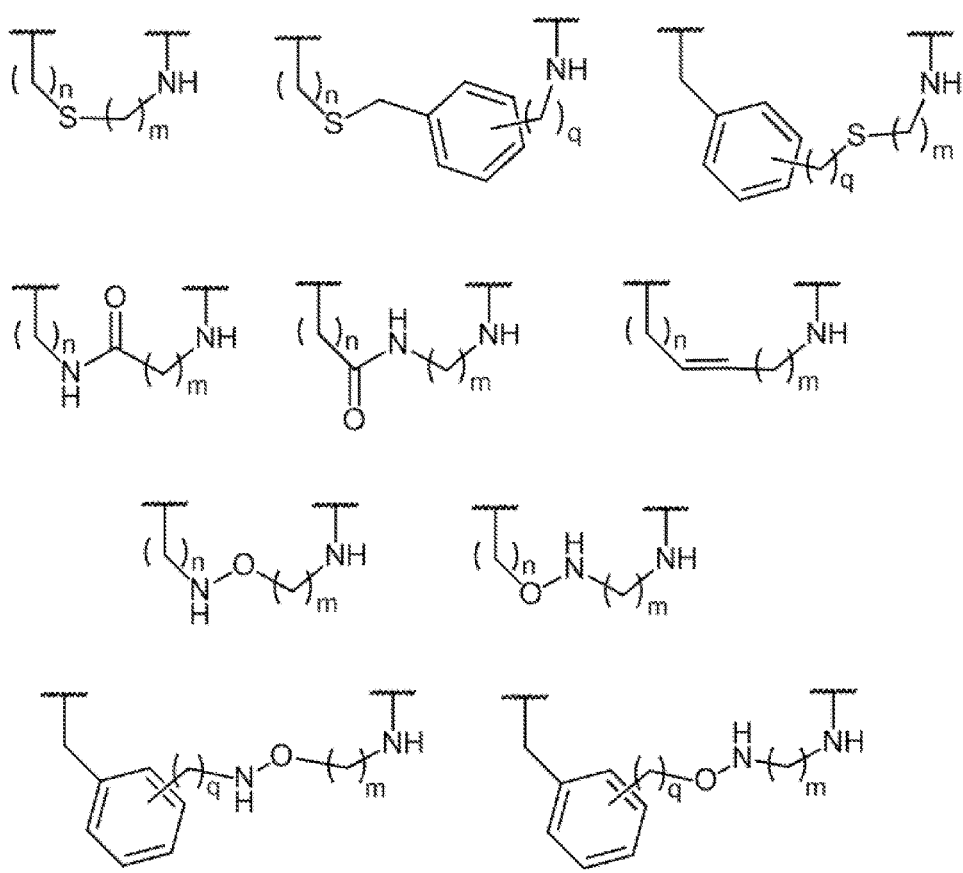

FIG. 17. Structures of additional macrocycle-forming linkers of formula [-L$_1$-Z-L$_2$-Y-] that can be used in the methods described herein. The symbol

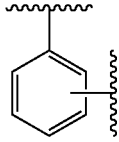

indicates an ortho-, meta- or para-disubstituted phenyl ring. The symbols 'm' and 'n' are integer numbers from 1 to 10; 'q' is an integer number from 0 to 5.

Figure 18:
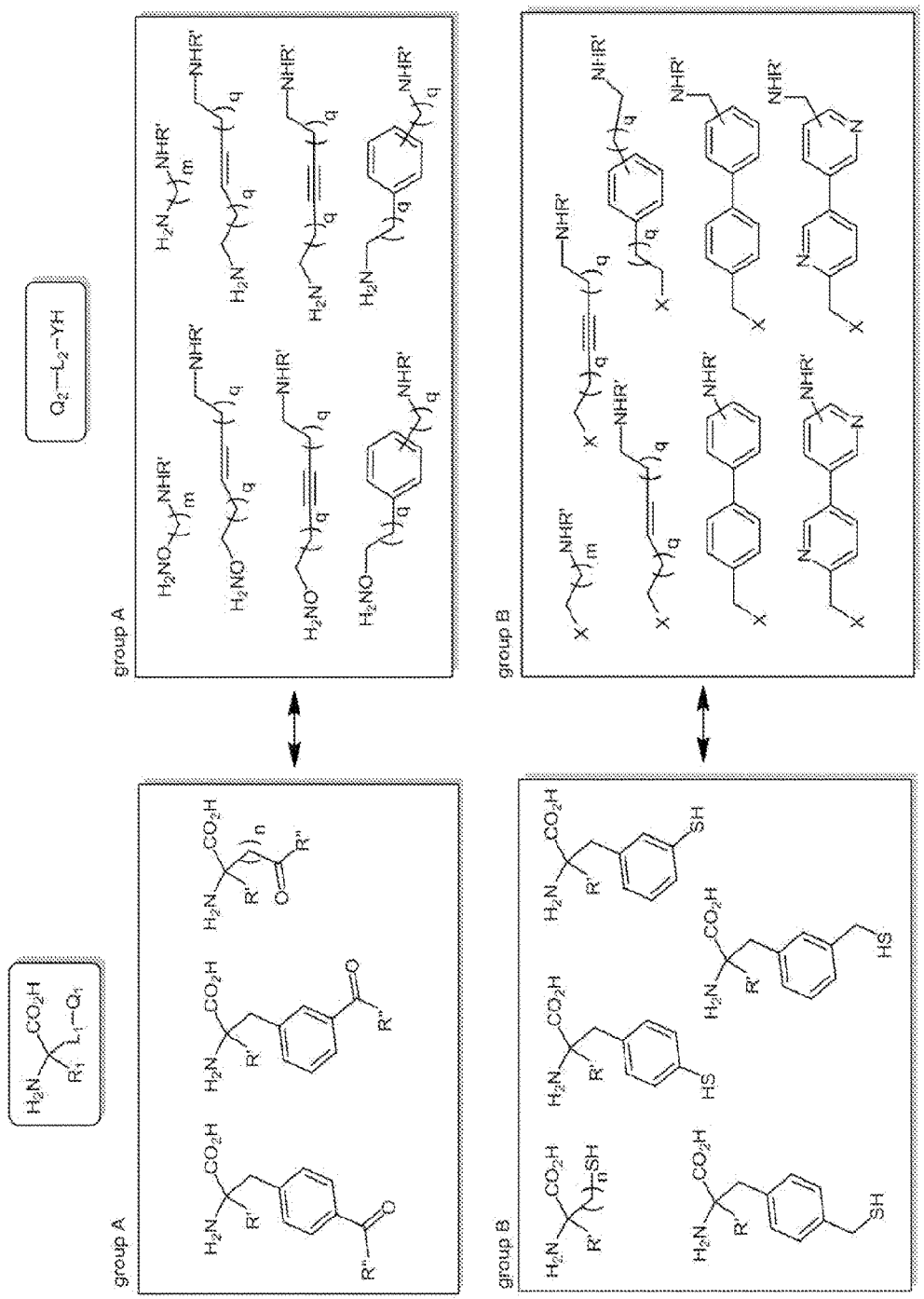

FIG. 18. Structures of amino acid analogs (left panel) and compatible macrocycle-forming linker reagents (right panel linked by arrow) that can be used in the methods described herein. The symbol

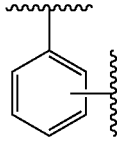

indicates an ortho-, meta- or para-disubstituted phenyl ring. The symbols 'm' and 'n' are integer numbers from 1 to 10; 'q' is an integer number from 0 to 5. R' is —H or —CH$_3$; R" is —H, —CH$_3$ or —OH; X is —Cl, —Br, —I, —OTs, —OMs, or —OTf.

Figure 19:
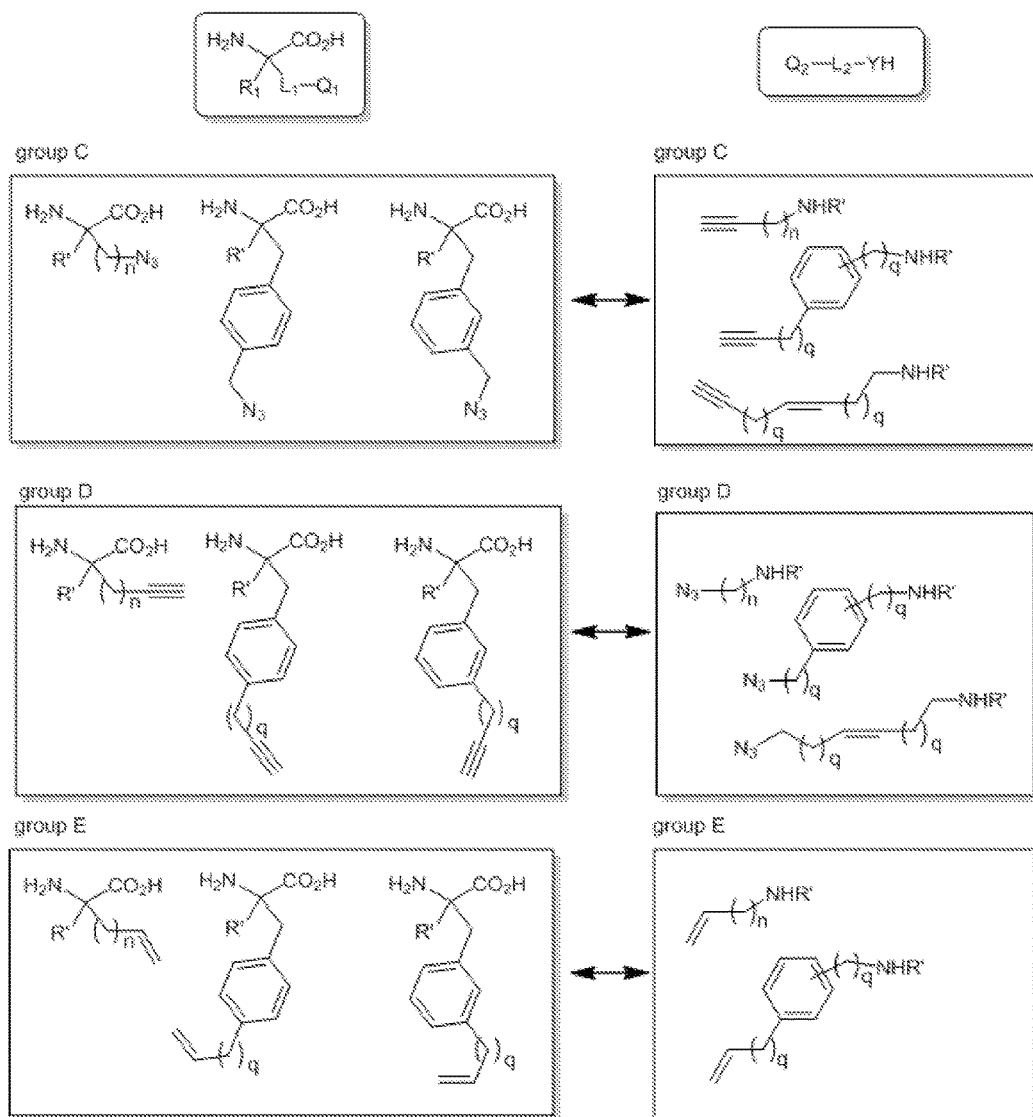

FIG. 19. Structures of additional amino acid analogs (left panel) and compatible macrocycle-forming linker reagents (right panel linked by arrow) that can be used in the methods described herein. The symbol

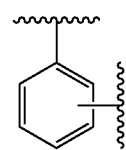

indicates an ortho-, meta- or para-disubstituted phenyl ring. The symbols 'm' and 'n' are integer numbers from 1 to 10; 'q' is an integer number from 0 to 5. R' is —H or —CH$_3$; X is —Cl, —Br, —I, —OTs, —OMs, or —OTf.

5. DETAILED DESCRIPTION

The present disclosure is directed to the production of α-helix peptidomimetics exhibiting increased conformational stability, biological activity, metabolic stability and/or cell permeability.

For clarity of disclosure, and not by way of limitation, the detailed description is divided into the subsections set forth below.

5.1 Definitions

Unless defined otherwise herein, all technical and scientific terms used herein have the same meaning as commonly understood by one of ordinary skill in the art to which the disclosure pertains.

The singular forms "a," "an," and "the" used herein include plural referents unless the content clearly dictates otherwise.

The term "plurality" includes two or more referents unless the content clearly dictates otherwise.

The term "functional group" as used herein refers to a contiguous group of atoms that, together, may undergo a chemical reaction under certain reaction conditions. Examples of functional groups are, among many others, —OH, —NH$_2$, —SH, —(C═O)—, —N$_3$, —C≡CH.

The term "aliphatic" or "aliphatic group" as used herein means a straight or branched C$_{1-15}$ hydrocarbon chain that is completely saturated or that contains one or more units (i.e., at least one unit) of unsaturation, or a monocyclic C$_{3-8}$ hydrocarbon, or bicyclic C$_{8-12}$ hydrocarbon that is completely saturated or that contains one or more units of unsaturation, but which is not aromatic (also referred to herein as "cycloalkyl"). For example, suitable aliphatic groups include, but are not limited to, linear or branched alkyl, alkenyl, alkynyl groups or hybrids thereof such as (cycloalkyl)alkyl, (cycloalkenyl)alkyl, or (cycloalkynyl)alkyl. The alkyl, alkenyl, or alkynyl group may be linear, branched, or cyclic and may contain up to 15, up to 8, or up to 5 carbon atoms. Alkyl groups include, but are not limited to, methyl, ethyl, propyl, cyclopropyl, butyl, cyclobutyl, pentyl, and cyclopentyl groups. Alkenyl groups include, but are not limited to, propenyl, butenyl, and pentenyl groups. Alkynyl groups include, but are not limited to, propynyl, butynyl, and pentynyl groups.

The term "aryl" and "aryl group" as used herein refers to an aromatic substituent containing a single aromatic or multiple aromatic rings that are fused together, directly linked, or indirectly linked (such as linked through a methylene or an ethylene moiety). A aryl group may contain from 5 to 24 carbon atoms, 5 to 18 carbon atoms, or 5 to 14 carbon atoms.

The terms "heteroatom" means nitrogen, oxygen, or sulphur, and includes any oxidized forms of nitrogen and sulfur, and the quaternized form of any basic nitrogen. Heteroatom further include Se, Si, and P.

The term "heteroaryl" as used herein refer to an aryl group in which at least one carbon atom is replaced with a heteroatom. In some embodiment, a heteroaryl group is a 5- to 18-membered, a 5- to 14-membered, or a 5- to 10-membered aromatic ring system containing at least one heteroatom selected from a group including, but not limited to oxygen, sulphur, and nitrogen atoms. Heteroaryl groups include, but are not limited to, pyridyl, pyrrolyl, furyl, thienyl, indolyl, isoindolyl, indolizinyl, imidazolyl, pyridonyl, pyrimidyl, pyrazinyl, oxazolyl, thiazolyl, purinyl, quinolinyl, isoquinolinyl, benzofuranyl, and benzoxazolyl groups.

A heterocyclic group may be any monocyclic or polycyclic ring system which contains at least one heteroatom and may be unsaturated or partially or fully saturated. The term "heterocyclic" thus includes heteroaryl groups as defined above as well as non-aromatic heterocyclic groups. In some embodiments, a heterocyclic group is a 3- to 18-membered, a 3- to 14-membered, or a 3- to 10-membered, ring system containing at least one heteroatom selected from a group including, but not limited to, oxygen, sulphur, and nitrogen atoms. Heterocyclic groups include, but are not limited to, the specific heteroaryl groups listed above as well as pyranyl, piperidinyl, pyrrolidinyl, dioaxanyl, piperazinyl, macrocyleolinyl, thiomacrocyleolinyl, macrocyleolinosulfonyl, tetrahydroisoquinolinyl, and tetrahydrofuranyl groups.

A halogen atom may be a fluorine, chlorine, bromine, or a iodine atom.

By "optionally substituted", it is intended that in the any of the chemical groups listed above (e.g., alkyl, alkenyl, alkynyl, heteroalkyl, heteroalkenyl, heteroalkynyl, aryl, heteroaryl, heterocyclic, triazolyl groups), one or more (i.e., at least one) hydrogen atoms are optionally replaced with an atom or chemical group other than hydrogen. Specific examples of such substituents include, without limitation, halogen atoms, hydroxyl (—OH), sulfhydryl (—SH), substituted sulfhydryl, carbonyl (—CO—), carboxy (—COOH), amino (—NH$_2$), nitro (—NO$_2$), sulfo (—SO$_2$—OH), cyano (—C≡N), thiocyanato (—S—C≡N), phosphono (—P(O)OH$_2$), alkyl, alkenyl, alkynyl, heteroalkyl, heteroalkenyl, heteroalkynyl, aryl, heteroaryl, heterocyclic, alkylthiol, alkyloxy, alkylamino, arylthiol, aryloxy, or arylamino groups. Where "optionally substituted" modifies a series of groups separated by commas (e.g., "optionally substituted AA, BB, or CC"; or "AA, BB, or CC optionally substituted with"), it is intended that each of the groups (e.g., AA, BB, or CC) is optionally substituted.

The term "heteroatom-containing aliphatic" as used herein refer to an aliphatic moiety where at least one carbon atom is replaced with a heteroatom, e.g., oxygen, nitrogen, sulphur, selenium, phosphorus, or silicon, and typically oxygen, nitrogen, or sulphur.

The terms "alkyl" and "alkyl group" as used herein refer to a linear, branched, or cyclic saturated hydrocarbon typically containing 1 to 24 carbon atoms, or 1 to 12 carbon atoms, such as methyl, ethyl, n-propyl, isopropyl, n-butyl, isobutyl, t-butyl, octyl, decyl and the like.

The term "heteroatom-containing alkyl" as used herein refers to an alkyl moiety where at least one carbon atom is replaced with a heteroatom, e.g., oxygen, nitrogen, sulphur, phosphorus, or silicon, and typically oxygen, nitrogen, or sulphur.

The terms "alkenyl" and "alkenyl group" as used herein refer to a linear, branched, or cyclic hydrocarbon group of 2 to 24 carbon atoms, or of 2 to 12 carbon atoms, containing at least one double bond, such as ethenyl, n-propenyl, isopropenyl, n-butenyl, isobutenyl, octenyl, decenyl, and the like.

The term "heteroatom-containing alkenyl" as used herein refer to an alkenyl moiety where at least one carbon atom is replaced with a heteroatom.

The terms "alkynyl" and "alkynyl group" as used herein refer to a linear, branched, or cyclic hydrocarbon group of 2 to 24 carbon atoms, or of 2 to 12 carbon atoms, containing at least one triple bond, such as ethynyl, n-propynyl, and the like.

The term "heteroatom-containing alkynyl" as used herein refer to an alkynyl moiety where at least one carbon atom is replaced with a heteroatom.

The term "heteroatom-containing aryl" as used herein refer to an aryl moiety where at least one carbon atom is replaced with a heteroatom.

The terms "alkoxy" and "alkoxy group" as used herein refer to an aliphatic group or a heteroatom-containing aliphatic group bound through a single, terminal ether linkage. In some embodiments, aryl alkoxy groups comprise 1 to 24 carbon atoms, and in other embodiments, alkoxy groups comprise 1 to 14 carbon atoms.

The terms "aryloxy" and "aryloxy group" as used herein refer to an aryl group or a heteroatom-containing aryl group bound through a single, terminal ether linkage. In some embodiments, aryloxy groups contain 5 to 24 carbon atoms, and in other embodiments, aryloxy groups contain 5 to 14 carbon atoms.

The term "substituents" refers to a contiguous group of atoms. Examples of "substituents" include, without limitation: alkoxy, aryloxy, alkyl, heteroatom-containing alkyl, alkenyl, heteroatom-containing alkenyl, alkynyl, heteroatom-containing alkynyl, aryl, heteroatom-containing aryl, alkoxy, heteroatom-containing alkoxy, aryloxy, heteroatom-containing aryloxy, halo, hydroxyl (—OH), sulfhydryl (—SH), substituted sulfhydryl, carbonyl (—CO—), thiocarbonyl, (—CS—), carboxy (—COOH), amino (—NH$_2$), substituted amino, nitro (—NO$_2$), nitroso (—NO), sulfo (—SO$_2$—OH), cyano cyanato (—O—C≡N), thiocyanato (—S—CN), formyl (—CO—H), thioformyl (—CS—H), phosphono (—P(O)OH$_2$), substituted phosphono, and phospho (—PO$_2$).

As used herein, the term "macrocycle" refers to a molecule having a chemical structure including a ring or cycle formed by at least 9 covalently bonded atoms.

The term "cyclic" and "macrocyclic" as used herein means having constituent atoms forming a ring. Thus, a "macrocyclic peptide-containing molecule" is a peptide-containing molecule that contains one or more rings (i.e., at least one ring) formed by atoms comprised in the molecule. "Cyclization" or "macrocyclization" as used herein refers to a process or reaction whereby a cyclic molecule is formed or is made to be formed. The term "peptidic backbone" as used herein refers to a sequence of atoms corresponding to the main backbone of a natural protein. A "non-peptidic backbone" as used herein refers to a sequence of atoms that does not correspond to a peptidic backbone.

As used herein, the terms "macrocyclic peptidomimetic" and "macrocyclic peptidomimetic molecule" refer to a compound comprising a plurality of amino acid residues joined by a plurality of peptide bonds and at least one macrocycle-forming linker which forms a macrocycle between the a carbon of one naturally-occurring amino acid residue or non-naturally-occurring amino acid residue or amino acid analog residue and the C-terminal carbonyl group (—C(O)—) of another naturally-occurring amino acid residue or non-naturally-occurring amino acid residue or amino acid analog residue. The macrocyclic peptidomimetics optionally include one or more (i.e., at least one) non-peptide bonds between one or more amino acid residues and/or amino acid analog residues, and optionally include one or more non-naturally-occurring amino acid residues or amino acid analog residues in addition to any which form the macrocycle.

The term "α-amino acid" or simply "amino acid" refers to a molecule containing both an amino group and a carboxyl group bound to a carbon which is designated the α-carbon. Suitable amino acids include, without limitation, both the D- and L-isomers of the naturally-occurring amino acids, as well as non-naturally occurring amino acids prepared by organic synthesis or other metabolic routes. Unless the context specifically indicates otherwise, the term amino acid, as used herein, is intended to include amino acid analogs.

The term "naturally occurring amino acid" refers to any one of the twenty amino acids commonly found in peptides synthesized in nature, and known by the one letter abbreviations A, R, N, C, D, Q, E, G, H, I, L, K, M, F, P, S, T, W, Y and V.

The term "amino acid analog" refers to a molecule which is structurally similar to an amino acid and which can be substituted for an amino acid in the formation of a peptide or macrocyclic peptidomimetic molecule. Amino acid analogs include compounds which are structurally identical to an amino acid, as defined herein, except for the inclusion of one or more (i.e., at least one) additional methylene groups between the amino and carboxyl group (e.g., α-amino β-carboxy acids), or for the substitution of the amino or carboxy group by a similarly reactive group (e.g., substitution of the primary amine with a secondary or tertiary amine, or substitution or the carboxy group with an ester).

The term "capping group" refers to the chemical moiety occurring at the amino terminus of the polypeptide chain comprised in the macrocyclic peptidomimetic molecule. The capping group of an amino terminus includes an unmodified amine (i.e., —NH$_2$) or an amine with a substituent. For example, the amino terminus may be substituted with an acyl group to yield a carboxamide at the N-terminus. Various substituents include but are not limited to substituted acyl groups, including $C_1$-$C_6$ carbonyls, $C_7$-$C_{30}$ carbonyls, and pegylated carbamates. Representative capping groups for the N-terminus include but are not limited to acetyl, propionyl, tert-butylcarbonyl, admantylcarbonyl, 1-naphtylmethylcarbonyl, isonicotinylcarbonyl, decanoylcarbonyl, palmitylcarbonyl, or a polyethylenglycole-carbonyl group.

The term "member" as used herein in conjunction with macrocycles or macrocycle-forming linkers refers to the atoms that form or can form the macrocycle, and excludes substituent or side chain atoms. By analogy, cyclodecane, 1,2-difluoro-decane and 1,3-dimethyl cyclodecane are all considered ten-membered macrocycles as the hydrogen or fluoro substituents or methyl side chains do not participate in forming the macrocycle.

The term "amino acid side chain" refers to a moiety attached to the α-carbon in an amino acid. For example, the amino acid side chain for alanine is methyl, the amino acid side chain for phenylalanine is phenylmethyl, the amino acid side chain for cysteine is thiomethyl, the amino acid side chain for aspartate is carboxymethyl, the amino acid side chain for tyrosine is 4-hydroxyphenylmethyl, etc. Other non-naturally occurring amino acid side chains are also included, for example, those that occur in nature (e.g., an amino acid metabolite) or those that are made synthetically (e.g., an α,α di-substituted amino acid).

The terms "peptide" and "polypeptide" as used herein refers to any chain of two or more naturally or non-naturally-occurring amino acids joined by a covalent bond (e.g., an amide bond. Polypeptides as described herein include full length proteins (e.g., fully processed proteins) as well as shorter amino acids sequences (e.g., fragments of naturally occurring proteins or synthetic polypeptide fragments).

As used herein, the term "stability" refers to the maintenance of a defined secondary structure in solution by a peptide or macrocyclic peptidomimetic molecule disclosed herein as measured by circular dichroism, NMR or another biophysical measure, or resistance to proteolytic degradation in vitro or in vivo. Non-limiting examples of secondary structures contemplated in this disclosure are α-helices, α-turns, $3_{10}$-helices, and π-helices.

The term "helical stability" as used herein refers to the maintenance of a helical structure by a peptide or macrocyclic peptidomimetic molecule disclosed herein as measured by circular dichroism, NMR or another biophysical method. For example, in some embodiments, the macrocyclic peptidomimetic molecule disclosed herein exhibit at least a 1.25, 1.5, 1.75 or 2-fold increase in α-helicity compared to a corresponding non-macrocyclic polypeptide as determined by circular dichroism.

The term "proteolytic stability" as used herein refers to the maintenance of an integer structure by a peptide or macrocyclic peptidomimetic molecule disclosed herein in the presence of one or more (i.e., at least one) proteases as measured by HPLC or another analytical method. For example, in some embodiments, the macrocyclic peptidomimetic molecule disclosed herein exhibit at least a 1.25, 1.5, 1.75 or 2-fold increased half-life in the presence of one or more proteases when compared to a corresponding non-macrocyclic polypeptide as determined by HPLC.

The term "contact" as used herein with reference to interactions of chemical units indicates that the chemical units are at a distance that allows short range non-covalent interactions (such as Van der Waals forces, hydrogen bonding, hydrophobic interactions, electrostatic interactions, dipole-dipole interactions) to dominate the interaction of the chemical units. For example, when a protein is 'contacted' with a chemical species, the protein is allowed to interact with the chemical species so that a reaction between the protein and the chemical species can occur.

The terms "affinity label" or "affinity tag", as used herein, refer to a molecule that allows for the isolation of another molecule covalently bound to it (e.g., a target polypeptide) by physical methods. Non-limiting examples of affinity labels are biotin and glutathione. Examples of physical methods useful for isolating an affinity labeled molecule include, but are not limited to, affinity chromatography, reverse-phase chromatography, ion-exchange chromatography, gel-permeation chromatography, and related techniques.

The term "fluorescent molecule", as used herein, refers to a molecule which upon excitation emits photons and is thereby fluorescent. Non-limiting examples of fluorescent molecules are coumarins, naphthalenes, pyrenes, fluoresceins, rhodamines, naphthoxanthenes, phenanthridines, boron difluoride dipyrromethenes (BODIPY), cyanines, phthalocyanines, oxazines and variously functionalized derivatives thereof.

The term "radioisotopic label," as used herein, refers to any molecule containing a group whose nuclei spontaneously release nuclear radiation, such as alpha, or beta particles, or gamma radiation.

The term "targeting agent", as used herein, is a molecular structure capable of directing another molecule covalently or non-covalently associated with the targeting agent to a specific organism, tissue, cell, or intracellular compartment. Non-limiting examples of targeting agents include antibodies, short peptides (e.g., Arg-Gly-Asp), and small molecules such as folic acid.

The term "therapeutic agent", as used herein, refers to any molecule of legally approved use for treatment of a human disease.

5.2 Macrocyclic Peptidomimetics

Provided are macrocyclic peptidomimetics of Formula (I):

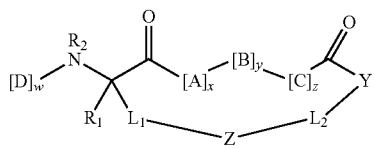

wherein:
each A, C, and D is independently a natural or non-natural amino acid, and the terminal D optionally include a capping group;
B is a natural amino acid, non-natural amino acid, an amino acid comprising at least one additional methylene groups between the amino and carboxyl group, an amino acid comprising an amino group which is a secondary or tertiary amine, an amino acid comprising a carboxy group replaced by an ester, [—NHN($R_3$)C(O)—], [—NH-$L_3$-CO—], [—NH-$L_3$-$SO_2$—], or [—NH-$L_3$-];
Y is —NH—, —N($R_4$)—, —NHN($R_4$)—, —NH—O—, —O—, or —S—;
Z is —SCH$R_6$—, —CH$R_6$S—, —C=C—, —N($R_5$)CO—, —CON($R_6$)—, —C($R_5$)=N($R_6$)—, —CH($R_5$)—NH($R_6$)—, —C($R_5$)=N—O—, —CH($R_5$)—NH—O—, —C($R_5$)=N—NH($R_6$)—, —CH($R_5$)—NH—NH($R_6$)—, or a triazole group;
$L_1$, $L_2$, and $L_3$ are independently aliphatic, aryl, substituted aliphatic, substituted aryl, heteroatom-containing aliphatic, heteroatom-containing aryl, substituted heteroatom-containing aliphatic, substituted heteroatom-containing aryl groups, each being unsubstituted or substituted with $R_7$;
$R_1$, $R_2$, $R_3$, $R_4$, $R_5$, and $R_6$ are independently —H, aliphatic, substituted aliphatic, aryl, or substituted aryl group;
each $R_7$ is independently —H, an aliphatic, substituted aliphatic, an aryl, a substituted aryl group;
x is an integer from 0-10;
y is an integer from 0-10;
z is an integer from 0-10;
w is an integer from 1-1000;
In some embodiments, x+y+z is at least 3. In other embodiments, x+y+z is 3, 4, 5, 6, 7, 8, 9 or 10. Each occurrence of A, B, C, or D in a macrocycle or macrocycle precursor is independently selected. For example, a sequence represented by the formula [A]$_x$, when x is 3, encompasses embodiments where the amino acids are not identical, e.g. Ala-Gly-Asp, as well as embodiments where the amino acids are identical, e.g. Ala-Ala-Ala. This applies for any value of x, y, z, or w in the indicated ranges.

In some embodiments, the macrocyclic peptidomimetic molecule comprises an α-helix as a secondary structural motif. In general, α-helices include between 3 and 4 amino acid residues per turn. In some embodiments, the α-helix comprised in the macrocyclic peptidomimetic molecule includes one (1) to 5 turns and, therefore, 3 to 20 amino acid residues. In specific embodiments, the α-helix comprised in the macrocyclic peptidomimetic molecule includes 1 turn, 2 turns, 3 turns, 4 turns, or 5 turns.

In some embodiments, the length of the macrocycle-forming linker, [-$L_1$-Z-$L_2$-Y—], as measured from the amino acid alpha carbon connected to $L_1$ to the Y group, is selected to increase the stability of an α-helix formed by the amino acid residues encompassed by the polypeptide or peptidomimetic sequence [A]$_x$-[B]$_y$-[C]$_z$. In some embodiments, the macrocycle-forming linker defined as [-$L_1$-Z-$L_2$-Y—], spans from 1 turn to 5 turns of the α-helix. In some embodiments, the macrocycle-forming linker spans approximately 1 turn, 2 turns, 3 turns, 4 turns, or 5 turns of the α-helix.

In some embodiments, the length of the macrocycle-forming linker, [-$L_1$-Z-$L_2$-Y—], has between 4 Å and 12 Å per turn of the α-helix. In other embodiments, the length of the macrocycle-forming linker has between 5 Å and 9 Å per turn of the α-helix.

In some embodiments, the macrocycle-forming linker spans approximately 1 turn of an α-helix, its length is equal to approximately 5 carbon-carbon bonds to 11 carbon-carbon bonds, and the linker contains at least 4 atoms to 10 atoms. In these cases, the resulting macrocycle forms a ring containing 15 members to 21 members.

In other embodiments, the macrocycle-forming linker spans approximately 2 turns of an α-helix, its length is equal to approximately 7 carbon-carbon bonds to 17 carbon-carbon bonds, and the linker contains at least 6 atoms to 16 atoms. In these cases, the resulting macrocycle forms a ring containing 28 members to 38 members.

In other embodiments, the macrocycle-forming linker spans approximately 3 turns of an α-helix, its length is equal to approximately 12 carbon-carbon bonds to 22 carbon-carbon bonds, and the linker contains at least 11 atoms to 21 atoms. In these cases, the resulting macrocycle forms a ring containing 43 members to 53 members.

In other embodiments, the macrocycle-forming linker spans approximately 4 turns of an α-helix, its length is equal to approximately 17 carbon-carbon bonds to 28 carbon-carbon bonds, and the linker contains at least 16 atoms to 27 atoms. In these cases, the resulting macrocycle forms a ring containing 59 members to 70 members.

In other embodiments, the macrocycle-forming linker spans approximately 5 turns of an α-helix, its length is equal to approximately 22 carbon-carbon bonds to 35 carbon-carbon bonds, and the linker contains at least 21 atoms to 34 atoms. In these cases, the resulting macrocycle forms a ring containing 75 members to 88 members.

In some embodiments, the macrocyclic peptidomimetic molecule of Formula (I) exhibits improved biological properties such as increased structural stability, increased affinity for a target, increased resistance to proteolytic degradation and/or increased cell permeability when compared to a non-macrocyclic polypeptide or peptidomimetic molecule counterpart. A reference non-macrocyclic counterpart for a compound of general Formula (I) is a compound of general of Formula (II)

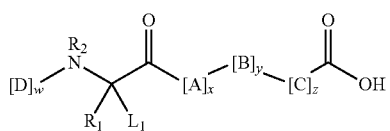

(II)

wherein A, B, C, D, R$_1$, R$_2$, L$_1$, x, y, z, and w are all as defined for Formula (I) above. Alternatively, a reference non-macrocyclic counterpart for a compound of general Formula (I) is a compound of general of Formula (III)

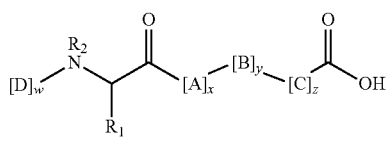

(III)

wherein A, B, C, D, R$_1$, R$_2$, x, y, z, and w are all as defined for Formula (I) above.

In some embodiment, the macrocyclic peptidomimetic molecule comprises an α-helix in aqueous solutions and exhibits an increased degree of α-helicity when compared to a non-macrocyclic counterpart as defined above. In some embodiments, the macrocyclic peptidomimetic molecule has at least a 1.1-fold, at least 1.5 fold, at least 2.0-fold, at least 2.5-fold, at least 3-fold, or at least 4-fold increase in alpha helicity as determined by circular dichroism compared to the reference non-macrocyclic counterpart of formula (II) or (III).

In some embodiments, the macrocyclic peptidomimetic molecule corresponds to a macrocyclic peptidomimetic molecule of general formula (I), wherein the macrocycle-forming linker [-L$_1$-Z-L$_2$-Y-] connecting the backbone and the carboxy terminus of the peptidomimetic molecule includes, but is not limited to,

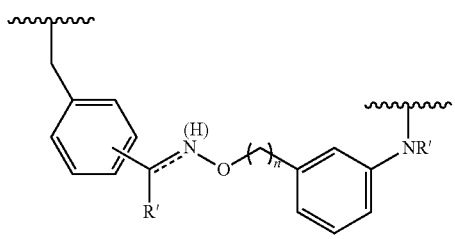

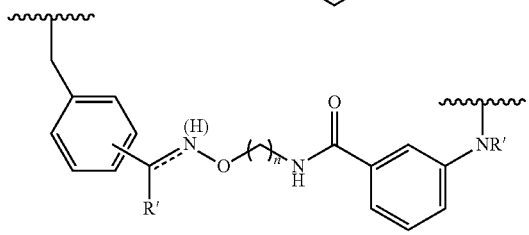

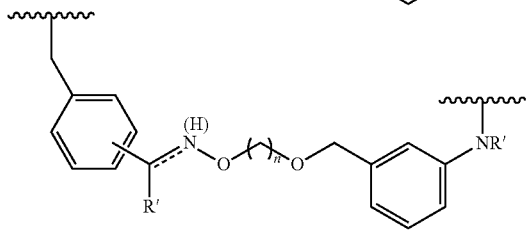

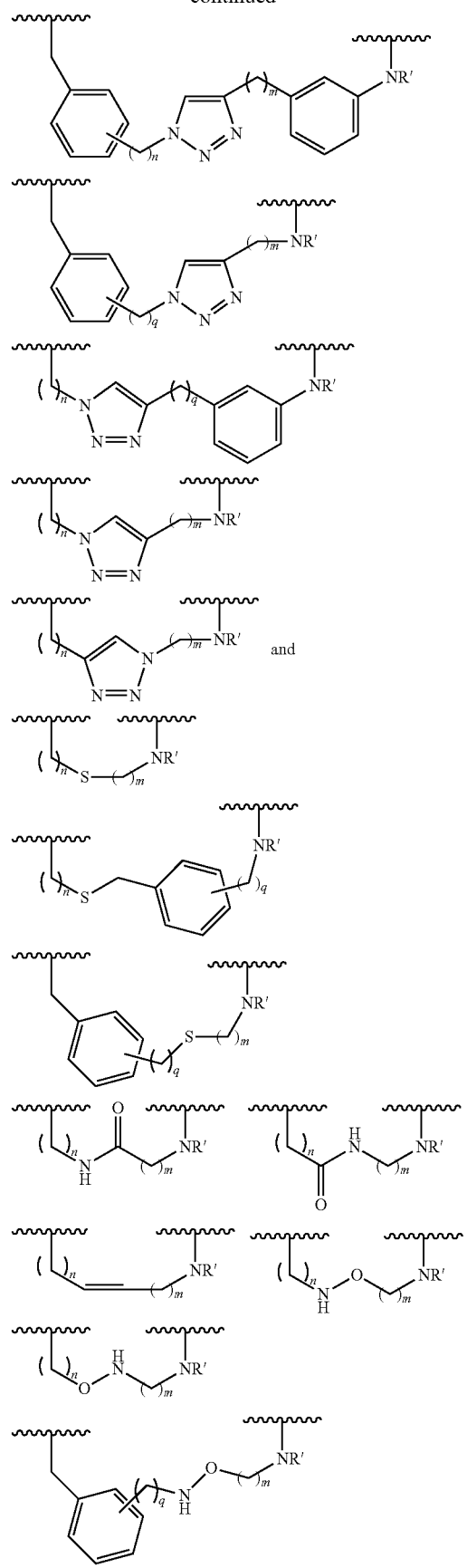

-continued

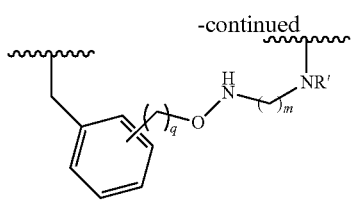

wherein
the symbol

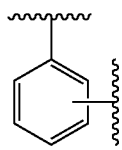

indicates an ortho-, meta- or para-disubstituted phenyl ring;

'm' and 'n' are each independently an integer number ranging from 1 to 10;

'q' is an integer number from 0 to 5; and each R' is independently —H or —CH$_3$.

In some embodiments, the macrocyclic peptidomimetic molecule of Formula (I) comprises a fluorescent label, an affinity label, a radioisotopic label, a targeting agent, or a therapeutic agent.

Any protein or polypeptide with a known primary amino acid sequence which contains an α-helix believed to mediate the interaction with another biomolecule (i.e., protein, DNA, RNA, oligosaccharide, lipid), thereby mediating a certain biological activity, is the subject of the present disclosure. For example, as schematically illustrated in FIG. 1, upon analysis of the polypeptide sequence encompassing the target α-helical motif, an appropriate macrocyclic peptidomimetic molecule for mimicking such motif can be generated by (a) replacing an appropriate amino acid residue within the target polypeptide sequence with an amino acid analog bearing a side-chain group, L$_1$, and then (b) tethering the side-chain group, L$_1$, to the carboxy terminus of the polypeptide sequence via a Z-L$_2$-Y linker moiety. Most conveniently, the linkage between the L$_1$ group and the Z-L$_2$-Y linker moiety is achieved by means of two functional groups (e.g., -Q$_1$ and -Q$_2$) that react with each other selectively and efficiently under appropriate reaction conditions. Most conveniently, the linkage between the Z-L$_2$-Y linker moiety and the carboxy terminus of the polypeptide is achieved by means of a nucleophilic group —YH and an activated form the C-terminal carboxy group.

Using this strategy, different types of side-chain-to-C-terminus macrocyclic α-helix peptidomimetics can be obtained, as exemplified by the structures provided in FIG. 2. Optimal positions for the side-chain-to-C-terminus tethering are determined by ascertaining which molecular surface of the α-helix is required for biological activity and, therefore, across which other surface the macrocycle-forming-linker can be introduced in order to generate a macrocyclic molecule without sterically blocking the surface required for biological activity. As illustrated in FIGS. 9A-9B, such determinations can be made using methods such as X-ray crystallography of complexes between the protein containing the target α-helical motif, or the isolated α-helix, and the natural binding partner to visualize residues and surfaces of the α-helix that are involved in activity. Alternatively, site-directed mutagenesis can be used to identify the residues in the α-helical motif that relate to biological activity. Based on this information, the appropriate side-chain and C-terminal attachment sites for constraining the target α-helical motif by means of the amino acids analogs and macrocycle-forming linkers can be chosen. For example, for an α-helical secondary structure, one surface of the helix (e.g., a molecular surface extending longitudinally along the axis of the helix and radially 45-135° about the axis of the helix) may be required to make contact with another biomolecule in vivo or in vitro for biological activity. In such a case, a macrocycle-forming linker is designed to link the α-carbon and carboxy end of the helix while extending longitudinally along the surface of the helix in the portion of that surface not directly required for activity.

5.3 Synthesis of Macrocyclic Peptidomimetics

In general, the synthesis of the macrocyclic peptidomimetic molecules disclosed herein involves (a) synthesizing a precursor polypeptide containing an appropriately functionalized side-chain group, L$_1$, and an activated C-terminal carboxy group, and then (b) contacting the precursor polypeptide with an appropriately functionalized linker reagent to yield a macrocyclic peptidomimetic in which the side-chain group, L$_1$, is covalently linked to the C-terminal carboxy group of the polypeptide. This general method permits the side-chain-to-C-end cyclization of a precursor polypeptide to yield novel compounds that exhibit improved biological properties such as structural stability, affinity for a target, resistance to proteolytic degradation and/or cell permeability. In addition, this general method permits the rapid and selective incorporation of a broad diversity of linker moieties into the macrocyclic peptidomimetic molecules to permit the generation of a library of related macrocycles. This general method also permits the facile incorporation of labels (e.g., radioisotopes, chemiluminescent or fluorescent labels) or therapeutic agents into these macrocyclic compounds.

Accordingly, a method is provided for synthesizing a macrocyclic peptidomimetic molecule, the method comprising contacting a precursor peptidomimetic molecule of Formula (IV):

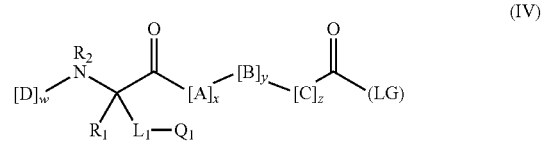

(IV)

with a linker reagent of Formula (V):

(V)

wherein

A, B, C, D, R$_1$, R$_2$, L$_1$, L$_2$, Y, x, y, z, and w are all as defined above for the compound of Formula (I);

x+y+z is at least 3;

Q$_1$ and Q$_2$ are two reactive functional groups capable of reacting with each other to form a group Z as defined above for the compound of Formula (I);

(LG) is a group that activates the terminal carboxylic acid carbonyl group toward nucleophilic substitution by means of the nucleophilic group —YH in the linker reagent of Formula (V), thereby forming a covalent —C(O)—Y— bond;

the contacting results in a covalent linkage between the side-chain group, $L_1$, and the C-terminal carboxyl group via a linker moiety, —Z-$L_2$-Y—, to give a compound of Formula (I).

In some embodiments, the functional group $Q_1$ includes, but is not limited to, sulphydryl (—SH), amino (—NHR$_5$), alkenyl (—C=CH$_2$), alkynyl (—C≡CH), azido (—N$_3$), keto (—C(O)R$_5$—), and carboxy (—C(O)OH) group, wherein R$_5$ is —H, aliphatic, substituted aliphatic, aryl, or substituted aryl group.

In each instance, the functional group $Q_2$ is selected so that a covalent bond-forming reaction can occur between $Q_1$ and $Q_2$. A person skilled in the art will be able to readily identify, given a certain $Q_1$ group, a suitable $Q_2$ for this purpose. In some embodiments, the functional group $Q_2$ includes, but is not limited to, —CH(R$_6$)X, where X is F, Cl, Br, or I, amino (—NHR$_6$), oxyamino (—ONH$_2$), hydrazino (—NR$_6$NH$_2$), alkenyl (—C=CH$_2$), alkynyl (—C≡CH), azido (—N$_3$), keto (—C(O)R$_6$—), or carboxy (—COOH) group, wherein R$_6$ is —H, aliphatic, substituted aliphatic, aryl, or substituted aryl group.

The activation of C-terminal carboxylic acid group toward nucleophilic substitution can be carried out by methods well known in the art. For example the C-terminal carboxylic acid group may be activated by conversion to an acyl chloride using PCl$_5$ or SOCl$_2$, conversion to an acyl azide by hydrazinolysis of a protected amino acid or peptide ester followed by treatment with NaNO$_2$ in aqueous acid, conversion to an O-acylisourea by reaction with dicyclohexylcarbodiimide, conversion to an acyloxyphosphonium or uronium species by reacting a carboxylate anion with a phosphonium or uronium cation (e.g. BOP, PyBOP or HBTU), or conversion to a thioester (e.g. phenyl thioester) or activated ester (e.g., pentafluorophenol ester) by reacting any of the aforementioned activated acid derivatives with a thiol or alcohol, respectively. In some embodiments, the (LG) group activating the C-terminal carboxylic acid group toward nucleophilic substitution is an acid chloride, an acid anhydride, an acyl azide, an O-acylisourea, a phosphonium compound, an activated ester or a thioester. In specific embodiments, the activated C-terminal carboxylic acid is in the form of a thioester, wherein the (LG) group is an aryl mercaptan (e.g. thiophenol, benzylmercaptan, and the like), an alkyl mercaptan (e.g. β-mercaptoethanol, MESNA, and the like), or an intein protein.

The precursor peptidomimetic molecules and macrocyclic peptidomimetic molecules can be synthesized by solution phase methods or solid-phase methods. Furthermore, the precursor peptidomimetic molecules and macrocyclic peptidomimetic molecules can contain naturally-occurring, non-naturally-occurring amino acids, and/or amino acid analogs. Alternative but equivalent protecting groups, leaving groups or reagents can be substituted, and certain of the synthetic steps can be performed in alternative sequences or orders to produce the desired compounds. Synthetic chemistry transformations and protecting group methodologies (protection and deprotection) useful in synthesizing the compounds described herein include, for example, those such as described in Larock, *Comprehensive Organic Transformations*, VCH Publishers (1989); Greene and Wuts, *Protective Groups in Organic Synthesis,* 2d. Ed., John Wiley and Sons (1991); Fieser and Fieser, *Fieser and Fieser's Reagents for Organic Synthesis*, John Wiley and Sons (1994); and Paquette, ed., *Encyclopedia of Reagents for Organic Synthesis*, John Wiley and Sons (1995), and subsequent editions thereof.

The macrocyclic peptidomimetic molecules can be made, for example, by chemical synthesis methods, such as described in Fields et al., Chapter 3 in *Synthetic Peptides: A User's Guide*, ed. Grant, W. H. Freeman & Co., New York, N.Y., 1992, p. 77. Hence, for example, peptides are synthesized using the automated Merrifield techniques of solid phase synthesis with the amine protected by either tBoc or Fmoc chemistry using side chain protected amino acids on, for example, an automated peptide synthesizer (e.g., Applied Biosystems (Foster City, Calif.), Model 430A, 431, or 433).

One manner of producing the precursor peptides and peptidomimetics described herein uses solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Side chain functional groups are protected as necessary with base stable, acid labile groups. Longer precursor peptides are produced, for example, by conjoining individual synthetic peptides using native chemical ligation.

The precursor peptides and peptidomimetics are made, for example, in a high-throughput, combinatorial fashion using, for example, a high-throughput polychannel combinatorial synthesizer (e.g., Model Apex 396 multichannel peptide synthesizer from AAPPTEC, Inc., Louisville, Ky.).

The section below provides examples of the diverse methods available for use in the preparation of the compounds disclosed herein. However, the disclosure is not intended to limit the scope of reactions or reaction sequences that are useful in preparing the compounds disclosed herein.

The synthetic schemes of FIGS. 3 and 4 are provided to illustrate some embodiments and are not intended to limit the scope of the compounds and methods described herein. For simplicity, in these illustrative schemes (a) the amino acid para-acetyl-phenylalanine (pAcF) is depicted as an example of an amino acid analog bearing a functionalized side-chain group, -$L_1$-$Q_1$, wherein the linker group, $L_1$, is —CH$_2$—C$_6$H$_4$—, and the reactive functional group, $Q_1$, is —C(O)—CH$_3$; and (b) the compound 3-amino-N-(3-(aminooxy)propyl)-4-(mercaptomethyl)benzamide) (SP8) is depicted as an example of a functionalized linker reagent of general formula (V), $Q_2$-Z-$L_2$-YH, wherein the $Q_2$ group is —ONH$_2$, the —YH group is —NH$_2$, and the $L_2$ group is —(CH$_2$)$_3$—NHCO-(4-(CH$_2$SH))C$_6$H$_3$—. The symbol "[—NHCH(R)CO-]$_n$" represents a sequence of amide bond-linked moieties such as a polypeptide sequence composed of natural or unnatural amino acids. As described previously, a formula such as "[—NHCH(R)CO—]$_n$" encompasses, for example, sequences of non-identical amino acids as well as sequences of identical amino acids.

In the first general method exemplified in FIG. 3, the precursor peptidomimetic molecule is synthesized by solid-phase peptide synthesis (SPPS) ("*Bioorganic Chemistry: Peptides and Proteins*", Oxford University Press, New York: 1998)) using commercially available N-α-Fmoc amino acids and a safety-catch linker resin. In this example, the amino acid analog carrying the appropriately functionalized side-chain group -$L_1$-$Q_1$ for mediating macrocyclization (e.g. pAcF) is para-acetyl-phenylalanine (pAcF). pAcF can be synthesized in racemic form using known methods (Frost, Vitali et al. 2013), followed by enzymatic resolution and conversion to the appropriately protected N-α-Fmoc-pAcF as illustrated in FIGS. 5A-5D. After assembly of the acyclic precursor peptidomimetic molecule by SPPS, the sidechain-protected precursor peptidomimetic molecule is cleaved from the resin via alkylation of the sulfonamide anchoring group with iodoacetonitrile followed by treatment with a thiol. This step also activates the C-terminal carboxy group of the precursor peptidomimetic molecule in the form of a thioester. The precursor peptidomimetic molecule is then reacted, as a crude mixture or after purification, with an appropriate macrocycle-forming linker reagent (i.e., oxyamino/amino-thiol reagent SP8 in this example) to yield the macrocyclic peptidomimetic molecule in partially or fully protected form (in solution cyclization, FIG. 3). This product is then deprotected by standard conditions (e.g., strong acid such as 95% TFA) to yield the desired macrocyclic peptidomimetic molecule. In some embodiments, the cyclization reaction is performed in an aqueous solution at pH 8. In other embodiments, the solvent used for the alkylation reaction is DMF or methanol. In other embodiments, after alkylation of the sulfonamide anchoring group with iodoacetonitrile the resin-bound precursor peptidomimetic molecule is made react directly with the macrocycle-forming linker reagent so that formation of the macrocyclic product in partially or fully protected form is accompanied by its release from the resin (on-column cyclization, FIG. 3). Deprotection of the released product then yields the desired final macrocyclic product.

In other embodiments, the acyclic precursor peptidomimetic is first assembled by SPPS, then cleaved from the resin in side-chain protected form and with a free C-terminal carboxylic group (—COOH), then converted to a C-terminal thioester (e.g., via activation of the C-terminal carboxylic group, followed by reaction with a thiol). The C-terminal thioester precursor peptidomimetic is then cyclized by means of an appropriate macrocycle-forming linker reagent.

In the second general method exemplified in FIG. 4, the precursor polypeptide is produced by recombinant expression in living cells or by known in vitro, cell-free, expression methods. In this case, the amino acid analog carrying the appropriately functionalized side-chain group $-L_1-Q_1$ for mediating macrocyclization (e.g. pAcF) is introduced into the recombinant polypeptide by means of art-known methods such as, for example, amber stop codon suppression in the presence of engineered aminoacyl-tRNA synthetase/tRNA for ribosomal incorporation of the desired non-natural amino acid (Frost, Vitali et al. 2013). Furthermore, the recombinant polypeptide can be genetically fused to an intein protein in order to generate a reactive thioester group at the C-terminal end of the peptide, thereby enabling C-end ligation of the polypeptide to the macrocycle-forming linker. The macrocyclic peptidomimetic is then produced by reaction of the recombinantly produced intein-fused precursor polypeptide with the macrocycle-forming linker reagent (e.g., SP8 in this example) aqueous solutions. In some embodiments, the macrocyclization reaction is facilitated by the addition of a thiol catalyst (e.g. thiophenol or MESNA).

5.4 Amino Acid Analogs

The present disclosure contemplates the use of both naturally-occurring and non-naturally-occurring amino acids and amino acid analogs in the synthesis of the macrocyclic peptidomimetic molecules described above. Any amino acid or amino acid analog amenable for the synthesis of stable side-chain-C-end linked macrocyclic peptides and peptidomimetic molecules can be used. Particularly useful amino acids for use are amino acids which contain a reactive side-chain functional group, such as a sulphydryl (—SH), amino (—NH$_2$), alkenyl (—C=CH$_2$), alkynyl (—C≡CH), azido (—N$_3$), keto (—C(O)—), or carboxy (—COOH) group, so that a covalent bond between the side-chain and the C-terminus of the polypeptide or peptidomimetic can be formed upon reaction with an appropriate linker reagent under suitable reaction conditions. For example, sulphydryl group-containing amino acids such as cysteine, homocysteine, o-, m-, and p-mercapto-phenylalanine, o-, m-, and p-mercaptomethyl-phenylalanine are contemplated as useful amino acids in the present disclosure. Similarly, amino group-containing amino acid such as 2,3-diaminopropanoic acid, 2,4-diaminobutanoic acid, ornithine, lysine, o-, m-, and p-amino-phenylalanine, o-, m-, and p-aminomethyl-phenylalanine; keto-containing amino acids such as o-, m-, and p-acetyl-phenylalanine, 2-amino-5-oxohexanoic acid, 2-amino-6-oxoheptanoic acid, 2-amino-7-oxooctanoic acid, 2-amino-2-oxopropanoic acid, 2-amino-8-oxononanoic acid; alkenyl group-containing amino acids such as 2-(2'-propenyl)glycine, 2-(3'-butenyl)glycine, 2-(4'-pentenyl)glycine, 2-(5'-hexenyl)glycine, 2-(6'-heptenyl)glycine, 2-(7'-octenyl)glycine; azido group-containing amino acids such as o-, m-, and p-azido-phenylalanine, 2-amino-3-azidopropanoic acid, 2-amino-4-azidobutanoic acid, 2-amino-5-azidopentanoic acid, 2-amino-6-azidohexanoic acid; and alkynyl group-containing amino acids such as 2-aminopent-4-ynoic acid, 2-aminohex-5-ynoic acid, 2-aminohept-6-ynoic acid, 2-aminooct-7-ynoic acid, 2-aminonon-8-ynoic acid, o-, m-, and p-propargyl-phenylalanine, o-, m-, and p-ethynyl-phenylalanine, are contemplated as useful amino acids in the present disclosure.

In some embodiments, the configuration of the alpha carbon in the amino acids and amino acid analogs is S. In other embodiments, the configuration of the alpha carbon in the amino acids and amino acid analogs is R. In some embodiments, some of the amino acids and amino acid analogs contained in the peptidomimetic have an alpha carbon atom in S configuration, whereas some of the amino acids and amino acid analogs have an alpha carbon atom in R configuration. In some embodiments the amino acid analogs are α,α-disubstituted, such as α-methyl-(S)-cysteine and α-methyl-(R)-cysteine. In some embodiments the amino acid analogs are N-alkylated, e.g., N-methyl-(S)-cysteine and N-methyl-(R)-cysteine.

Other amino acid analogs useful for forming macrocyclic peptidomimetic molecules disclosed herein are compounds of Formula (VI):

(VI)

wherein

L$_1$ is a linker group that includes, but is not limited to, aliphatic, aryl, substituted aliphatic, substituted aryl, heteroatom-containing aliphatic, heteroatom-containing aryl, substituted heteroatom-containing aliphatic, substituted heteroatom-containing aryl, alkoxy, and aryloxy groups, each being unsubstituted or substituted with R$_7$;

R$_1$ and R$_2$ are independently —H, aliphatic, substituted aliphatic, aryl, or substituted aryl group;

each R$_7$ is independently —H, an aliphatic, substituted aliphatic, an aryl, a substituted aryl group;

Q$_1$ is a reactive functional group includes, but is not limited to, sulphydryl (—SH), amino (—NHR$_5$), alkenyl (—C=CH$_2$), alkynyl (—C≡CH), azido (—N$_3$), keto (—C(O)R$_5$—), and carboxy (—COOH) group, wherein R$_5$ is -H, aliphatic, substituted aliphatic, aryl, or substituted aryl group.

In some embodiments, L$_1$ in the amino acid analog of formula (VI) includes, but is not limited to, C$_1$-C$_{24}$ alkyl, C$_1$-C$_{24}$ substituted alkyl, C$_1$-C$_{24}$ substituted heteroatom-containing alkyl, C$_1$-C$_{24}$ substituted heteroatom-containing alkyl, C$_2$-C$_{24}$ alkenyl, C$_2$-C$_{24}$ substituted alkenyl, C$_2$-C$_{24}$ substituted heteroatom-containing alkenyl, C$_2$-C$_{24}$ substituted heteroatom-containing alkenyl, C$_5$-C$_{24}$ aryl, C$_5$-C$_{24}$ substituted aryl, C$_5$-C$_{24}$ substituted heteroatom-containing aryl, C$_5$-C$_{24}$ substituted heteroatom-containing aryl, C$_1$-C$_{24}$ alkoxy, and C$_5$-C$_{24}$ aryloxy groups.

In some embodiments, the amino acid analog of formula (VI) comprises a fluorescent label, an affinity label, a radioisotopic label, a targeting agent, or a therapeutic agent.

5.5 Macrocycle-Forming Linker Reagents

Macrocycle-forming linker reagents are provided that are used to link the side-chain and the C-terminus of the precursor peptidomimetic molecules to form the macrocyclic peptidomimetic molecules disclosed herein. As described above, the macrocycle-forming linkers impart conformational rigidity, increased metabolic stability and/or increased cell penetrability. Furthermore, in some embodiments, the macrocycle-forming linkages stabilize the α-helical secondary structure of the macrocyclic peptidomimetic molecules.

In some embodiments, the macrocycle-forming linker reagent is a compound of Formula (V),

Q$_2$-L$_2$-Y—H    (V)

wherein,

Y is —NH—, —N(R$_4$)—, —NHN(R$_4$)—, —O—NH—, —O—, or —S—, wherein R$_4$ is —H, aliphatic, substituted aliphatic, aryl, or substituted aryl group;

L$_2$ is aliphatic, aryl, substituted aliphatic, substituted aryl, heteroatom-containing aliphatic, heteroatom-containing aryl, substituted heteroatom-containing aliphatic, substituted heteroatom-containing aryl groups, each being unsubstituted or substituted with R$_7$, wherein R$_7$ is independently —H, an aliphatic, substituted aliphatic, an aryl, a substituted aryl group;

Q$_2$ includes, but is not limited to, —CH(R$_6$)X, where X is F, Cl, Br, or I, amino (—NHR$_6$), oxyamino (—ONH$_2$), hydrazino (—NR$_6$NH$_2$), alkenyl (—C=CH$_2$), alkynyl (—C≡CH), azido (—N$_3$), keto (—C(O)R$_6$—), and carboxy (—COOH) group, wherein R$_6$ is —H, aliphatic, substituted aliphatic, aryl, or substituted aryl group.

In some embodiments, L$_2$ comprises a fluorescent label, an affinity label, a radioisotopic label, a targeting agent, or a therapeutic agent.

As described above, the choice of Q$_2$ in the macrocycle-forming linker reagent is dependent upon the choice of the group Q$_1$ occurring in the precursor peptidomimetic molecule, so that a bond-forming reaction can take place between these two functional under suitable reaction conditions according to procedured well known in the art. For example, when Q$_1$ is an alkynyl group (—C≡CH), Q$_2$ can be an azido group (—N$_3$) and a bond-forming reaction between these groups can be carried out in the presence of Cu(I) as catalyst via an azido-alkyne 1,3-dipolar cycloaddition to yield a side-chain linkage between L$_1$ and L$_2$ in the form of a triazole group (Z=triazole). As another example, when Q$_1$ is an alkenyl group (—C=CH$_2$), Q$_2$ can be an alkenyl group (—C=CH$_2$) and a bond-forming reaction between these groups can be carried out in the presence of a Ru-catalyst (e.g. Grubbs' catalyst) via an olefin metathesis reaction to yield a side-chain linkage between L$_1$ and L$_2$ in the form of an olefinic group (Z=—CH=CH—). As another example, when Q$_1$ is an ketone (—C(O)CH$_3$), Q$_2$ can be an oxyamino group (—ONH$_2$) and a bond-forming reaction between these groups can carried out under acidic conditions (e.g. in aqueous solvent at pH 5.0) via oxime ligation to yield a side-chain linkage between L$_1$ and L$_2$ in the form of an oxime group (Z=—C(CH$_3$)=N—O—). As another example, when Q$_1$ is a sulphydryl group (—SH), Q$_2$ can be an alkyl bromide (—CH$_2$Br) and a bond-forming reaction between these groups can carried out under alkaline conditions (e.g. in aqueous solvent at pH 8.0) via nucleophilic substitution to form a side-chain linkage between L$_1$ and L$_2$ in the form of a thioether group (Z=—CH$_2$S—). As another example, when Q$_1$ is a carboxylic group (—COOH), Q$_2$ can be an amino group (—NH$_2$) and a bond-forming reaction between these groups can carried out under standard amide coupling conditions (e.g. with a carbodiimide coupling reagent in DMF) to form a side-chain linkage between L$_1$ and L$_2$ in the form of a amide group (Z=—C(O)NH—). A person skilled in the art will be able to readily identify suitable combination of Q$_1$ and Q$_2$ as well as suitable reaction conditions under which Q$_1$ and Q$_2$ react together to form a covalent side-chain linkage to form the macrocyclic peptidomimetics.

The —YH is a nucleophilic group that can react with the activated C-terminal carboxylic group of the precursor peptidomimetic molecule so that a covalent bond is formed between the Y group and such C-terminal carboxylic group. Depending on the nature of the —YH group, the covalent linkage between the C-terminus of the peptidomimetic molecule and the macrocycle-forming linker comprise a primary amide (—C(=O)NH—), a secondary amide (—C(=O)N(R)—), a hydrazide (—C(=O)NHN(R)—), a oxyamide (—C(=O)NH—O—), an ester (—C(=O)O—) or a thioester (—C(=O)S—) group.

As described above, the activated C-terminal carboxylic acid group can be in the form of an acid chloride, an acid anhydride, an acyl azide, an O-acylisourea, a phosphonium compound, an activated ester or a thioester.

In some embodiments, the "C-terminal coupling reaction", that is the bond-forming reaction between the —YH group and the activated C-terminal carboxylic group in the precursor polypeptide or peptidomimetic molecule, is performed prior to the "side-chain coupling reaction", that is the bond-forming reaction between the Q$_1$ in the precursor molecule and the Q$_2$ group in the macrocycle-forming linker reagent. In other embodiments, the side-chain coupling reaction is performed prior to the C-terminal coupling reaction. In other embodiments, the side-chain coupling reaction and the C-terminal coupling reaction are performed concurrently, that is in a single reaction. Depending on the nature of the activated C-terminal carboxylic group, —YH, Q$_1$, and Q$_2$ groups, a person skilled in the art will be able to identify the most suitable reaction sequence for generating the macrocyclic molecules disclosed herein.

In some embodiments, the —YH group in the macrocycle-forming linker reagent is a primary or secondary amino group (—NH$_2$ or —NHR) and the L$_2$ component contains a sulphydryl group (—SH) which is separated from the —YH group by three or four bonds. These 1,2- or 1,3-aminothiol moieties are particularly useful for C-terminal coupling reactions in which the activated C-terminal carboxylic group is in the form of an alkyl-, aryl-, or intein-thioester. In particular, the thiol group in the macrocycle-forming linker reagent can facilitate the C-terminal coupling reaction by reacting with the C-terminal alkyl-, aryl-, or intein-thioester in a native chemical ligation-like transthioesterification reaction followed by S-to-N acyl transfer to give a stable amide bond between the C-terminus of the peptidomimetic molecule and the moiety derived from macrocycle-forming linker reagent.

In some embodiments, $L_2$ in the macrocycle-forming linker reagent of formula (V) includes, but is not limited to, $C_1$-$C_{24}$ alkyl, $C_1$-$C_{24}$ substituted alkyl, $C_1$-$C_{24}$ substituted heteroatom-containing alkyl, $C_1$-$C_{24}$ substituted heteroatom-containing alkyl, $C_2$-$C_{24}$ alkenyl, $C_2$-$C_{24}$ substituted alkenyl, $C_2$-$C_{24}$ substituted heteroatom-containing alkenyl, $C_2$-$C_{24}$ substituted heteroatom-containing alkenyl, $C_5$-$C_{24}$ aryl, $C_5$-$C_{24}$ substituted aryl, $C_5$-$C_{24}$ substituted heteroatom-containing aryl, $C_5$-$C_{24}$ substituted heteroatom-containing aryl, $C_1$-$C_{24}$ alkoxy, and $C_5$-$C_{24}$ aryloxy groups.

The $L_2$ component of the macrocycle-forming linker reagent, $Q_2$-$L_2$-YH, may be varied in length depending on, among other things, the distance between the alpha carbon of the amino acid analog used for the side-chain linkage and the C-terminal carboxy group to be linked in the desired macrocyclic peptidomimetic molecule. Furthermore, as the length of $L_2$ component of the the macrocycle-forming linker reagent is varied, the length of $L_1$ can also be varied in order to create a linker of appropriate overall length as described above. For example, if the amino acid analog used is varied by adding an additional methylene unit to its $L_1$ component, the length of $L_2$ is decreased in length by one methylene unit to compensate for the increased lengths of $L_1$.

In some embodiments, $L_2$ in the macrocycle-forming linker reagent is an alkyl group of the formula —$(CH_2)_n$—, where n is an integer between 1 and 20. For example, n is 1, 2, 3, 4, 5, 6, 7, 8, 9, 10, 15 or 20. In other embodiments, $L_2$ is an alkenyl group, an aryl group, or a 1,2,3-triazolyl group.

In some embodiments, the amino acid analog of formula (VI) is a compound selected from a group of amino acid analogs including, but not limited to:

Group A amino acid analogs:

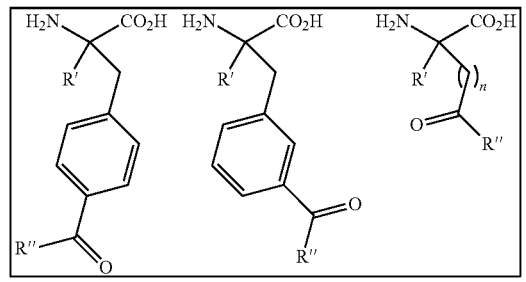

Group B amino acid analogs:

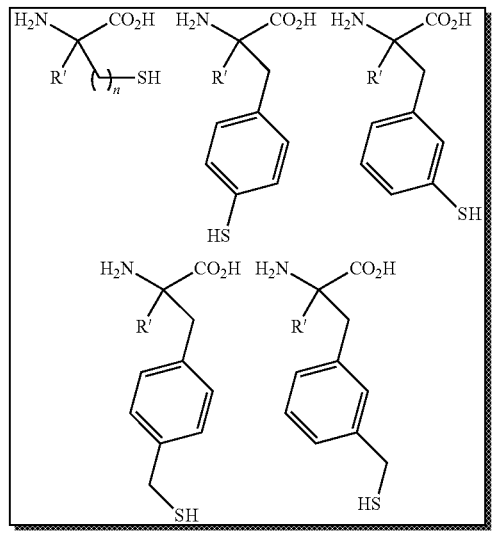

Group C amino acid analogs:

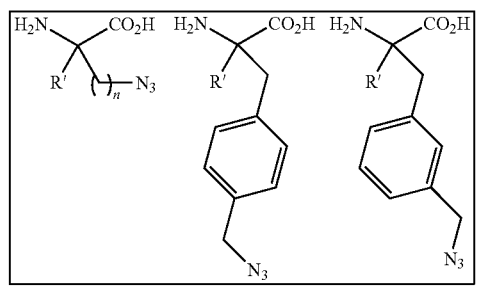

Group D amino acid analogs:

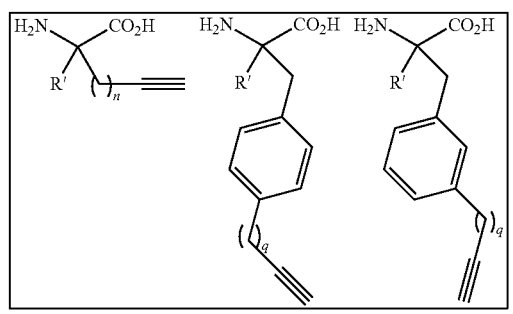

Group E amino acid analogs:

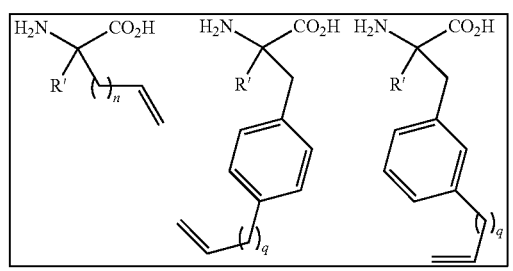

wherein 'n' is an integer number ranging from 1 to 10; 'q' is an integer number from 0 to 5; R' is —H or —$CH_3$; and R" is —H, —$CH_3$ or —OH;

and the macrocycle-forming linker reagent of formula (V) is a group of compatible macrocycle-forming linker reagents including, but not limited to:

Group A macrocycle-forming linker reagents:

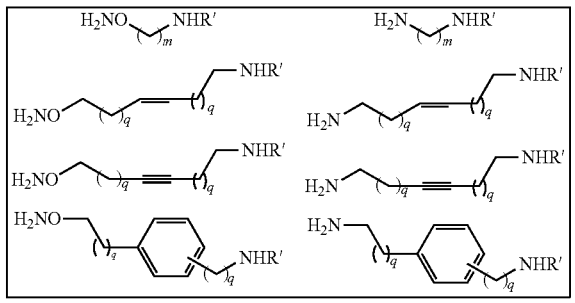

Group B macrocycle-forming linker reagents:

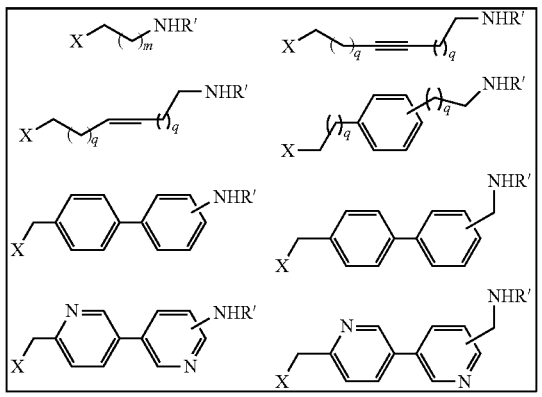

Group C macrocycle-forming reagents:

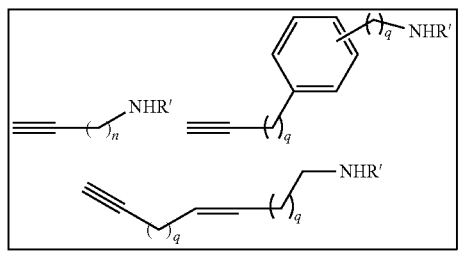

Group D macrocycle-forming reagents:

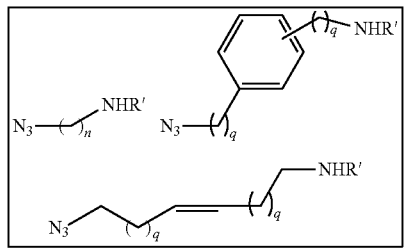

Group E macrocycle-forming reagents:

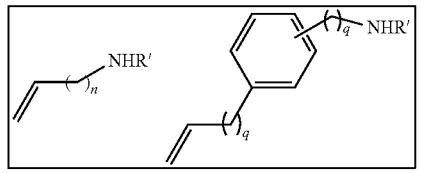

wherein the symbol

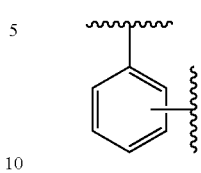

indicates an ortho-, meta- or para-disubstituted phenyl ring;
'm' and 'n' are each independently an integer number ranging from 1 to 10;
'q' is an integer number from 0 to 5;
R' is —H or —CH$_3$;
R" is —H, —CH$_3$ or —OH; and
X is —Cl, —Br, —I, —OTs, —OMs, or —OTf.

FIG. 16 shows structures of macrocycle-forming linkers of formula [-L$_1$-Z-L$_2$-Y-] that can be used in the methods described herein. The symbol "C⋯N" indicates a single or double bond. The symbol

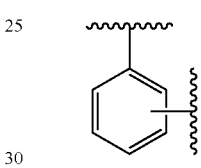

indicates an ortho-, meta- or para-disubstituted phenyl ring. R' is —H or —CH$_3$. The symbols 'm' and 'n' are integer numbers from 1 to 10; 'q' is an integer number from 0 to 5.

FIG. 17 shows structures of additional macrocycle-forming linkers of formula [-L$_1$-Z-L$_2$-Y-] that can be used in the methods described herein. The symbol

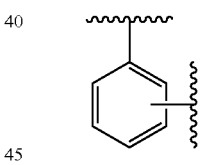

indicates an ortho-, meta- or para-disubstituted phenyl ring. The symbols 'm' and 'n' are integer numbers from 1 to 10; 'q' is an integer number from 0 to 5.

FIG. 18 shows structures of amino acid analogs (left panel) and compatible macrocycle-forming linker reagents (right panel linked by arrow) that can be used in the methods described herein. The symbol

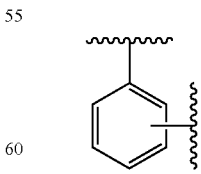

indicates an ortho-, meta- or para-disubstituted phenyl ring. The symbols 'm' and 'n' are integer numbers from 1 to 10; 'q' is an integer number from 0 to 5. R' is —H or —CH$_3$; R" is —H, —CH$_3$ or —OH; X is —Cl, —Br, —I, —OTs, —OMs, or —OTf.

FIG. 19 shows structures of additional amino acid analogs (left panel) and compatible macrocycle-forming linker reagents (right panel linked by arrow) that can be used in the methods described herein. The symbol

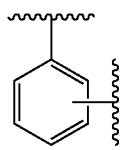

indicates an ortho-, meta- or para-disubstituted phenyl ring. The symbols 'm' and 'n' are integer numbers from 1 to 10; 'q' is an integer number from 0 to 5. R' is —H or —CH$_3$; X is —Cl, —Br, —I, —OTs, —OMs, or —OTf.

5.6 Assays

The properties of the macrocyclic peptidomimetics disclosed herein are assayed, for example, by using the methods described below. In some embodiments, a macrocycle has enhanced properties relative to a corresponding non-macrocyclic polypeptide. A corresponding non-macrocyclic polypeptide is, for example, an acyclic precursor of the macrocyclic peptidomimetic molecule, such as a compound of Formulas (II) or (III). Alternatively, a corresponding non-macrocyclic polypeptide is a polypeptide sequence, such as a natural polypeptide sequence which has substantial sequence overlap with the amino acid sequence comprised in the macrocyclic peptidomimetic molecule. Examples of non-macrocyclic polypeptides with substantial overlap with the amino acid sequence comprised in the macrocyclic peptidomimetic molecules disclosed herein are P1 (SEQ ID NO. 1), P2 (SEQ ID NO. 43), and P10 (SEQ ID NO. 12) in FIG. 10.

In general, a corresponding non-macrocyclic polypeptide can also be a labeled natural polypeptide or peptidomimetic precursor. Such labeling, for example by fluorescent or radioactive labeling, is used if necessary in some of the assays described below. In such assays, both the macrocycle and the corresponding non-macrocyclic polypeptide are typically labeled by similar or functionally equivalent methods.

Analysis of α-Helicity.

The alpha helical content of the macrocyclic peptidomimetic molecules and reference non-macrocyclic compounds disclosed herein can be determined by Circular Dichroism (CD) spectroscopy. CD spectra are recorded on a spectropolarimeter (e.g. JASCO J-710) at 20° C. using the following standard measurement parameters: wavelength, 195-250 nm; step resolution, 0.5 nm; speed, 10 nm/sec; accumulations, 3; response, 1 sec; bandwidth, 2 nm; path length, 0.1 cm. For these analyses, the macrocyclic molecules and reference non-macrocyclic compounds are typically dissolved in 5 mM potassium phosphate buffer (pH 7.0) to a final concentration of 20-50 µM. The mean residue ellipticity can be plotted vs. wavelength and the helical content of each peptide can be derived based on the following formula: $[\theta]_{222}/[40000 \times (n-4)/n]$ where n=number of peptide bonds (Johnson, W. C. and Tinoco, I., J Am Chem Soc, 1972, 94, 4389).

Analysis of Proteolytic Stability.

Linear peptides are susceptible to hydrolysis by proteases, which render them vulnerable to rapid degradation in vivo. Macrocyclization of peptide-based molecule according to the methods disclosed herein is expected to confer improved properties such as enhanced resistance against proteolysis. This property can be assessed by incubating the macrocyclic peptidomimetic molecules and the corresponding reference non-macrocyclic polypeptides in the presence of purified proteases or, alternatively, human blood serum. The in vitro proteolytic degradation of the compounds can be then monitored over time by HPLC equipped with a UV detector. From the resulting time-dependent curves, the half-life of the compounds can be measured. As an example, the in vitro proteolytic stability of macrocycles was measured by incubating the compound (10 µM) in 50 mM potassium phosphate buffer (pH 7.5) in the presence of chymotrypsin (1.0 µg/mL) at room temperature. At different time points (e.g. 0, 30, 60, 120, 180, 240 min), an aliquot of the reaction mixture (50 µL) was removed, quenched addition of TFA (5 µL) followed by HPLC analysis. Peptide cleavage was monitored based on the decrease of the peak area corresponding to the integer peptide.

In Vitro Protein Binding Assays.

The ability of the macrocyclic peptidomimetic molecules disclosed herein to bind a protein of interest can be assessed, for example, via an in vitro fluorescence polarization (FP) assay. For example, the ability of these compounds to bind to the oncoprotein HDM2 and/or HDMX can be established by incubating a fluorescently labelled (e.g., fluorescein-conjugated) derivative of the macrocyclic peptidomimetic molecule with increasing amounts of the protein and by measuring the increase in fluorescence polarization at increasing protein concentration. The principles of fluorescence polarization are well established and this assay relies on the enhancement of fluorescence polarization as a result of complex formation between the fluorescently labelled peptide and the protein. The variation in FP of the molecule as dependent upon the protein concentration can be then analyzed to measure the binding affinity of the compound to the protein in terms of equilibrium dissociation constant ($K_D$).

In Vitro Inhibition Assays.

The ability of the macrocyclic peptidomimetic molecules to bind a protein of interest and disrupt a target protein-protein interaction can be assessed, for example, via in vitro surface plasmon resonance (SPR)-based inhibition assays. For example, the ability of these compounds to inhibit the interaction of p53 with oncoprotein HDM2 and HDMX can be measured via an in-solution inhibition assay, in which a biotinylated p53-derived peptide (e.g., biotin-SGSG-p53$_{15-29}$) is first immobilized on a streptavidin-coated biosensor chip. Soluble HDM2 (or HDMX) is then incubated with varying concentrations of the macrocycle and the mixture is then injected over the functionalized surface. With increasing concentrations of the inhibitor, binding of HDM2 (or HDMX) to the surface is inhibited, leading to a decrease in biosensor response. The response-concentration curves can be then analyzed to measure the inhibitory activity of the compounds in terms of half-maximal inhibitory concentration (IC$_{50}$).

Analysis of Cell Permeability.

In some embodiments, the macrocyclic peptidomimetics described herein are more cell permeable than a corresponding non-macrocyclic counterpart. Macrocyclic peptidomimetic molecules with optimized side-chain-to-C-end tethers possess, for example, cell permeability that is at least 1.1-, 1.5-, 2-, or 3-fold greater or more than a corresponding non-macrocyclic counterpart. To measure the cell permeability of these compounds, intact cells are incubated with fluorescently labeled (e.g. fluorescein-conjugated) macrocyclic peptidomimetic molecule or corresponding non-macrocyclic counterpart (10 µM) for 4 hrs in serum free media at 37° C. Cells are then washed twice with media, incubated with trypsin (e.g. 0.25% trypsin, 10 min, 37° C.), then washed again and resuspended in PBS. Cellular fluorescence is analyzed, for example, by using a FACSCalibur flow cytometer. Alternatively, the ability of the fluorescently labelled compound to penetrate cells can be assessed by confocal fluorescence microscopy.

Analysis of Cellular Efficacy.

The cytotoxic activity of the macrocyclic peptidomimetic molecules is determined, for example, in cell-based assays using tumorigenic and non-tumorigenic cell lines and primary cells derived from human or mouse cell populations. Cell viability is monitored, for example, over 24-96 hrs of incubation with the macrocyclic peptidomimetic molecules (e.g. 0.1 to 100 µM) to identify those that reduce cell viability with a $EC_{50}$ lower than 100 µM. Several standard assays that measure cell viability are commercially available such as, for example the MTT (3-(4,5-dimethylthiazol-2-yl)-2,5-diphenyltetrazolium bromide) assay. Such assays can be used to assess the efficacy of the macrocyclic peptidomimetic molecules to reduce the viability of tumorigenic and non-tumorigenic cells. In addition, assays that measure Annexin V and caspase activation can be optionally used to assess whether the cytotoxicity of the macrocyclic peptidomimetic molecules is dependent upon activation of the apoptotic machinery, which is expected to result from reactivation of p53 activity.

5.7 Methods of Use

In some embodiments, the peptide sequence comprised in the macrocyclic peptidomimetic molecule of formula (I) is derived from HDM2 binding domain of the tumor suppressor p53 protein. The human transcription factor p53 induces cell cycle arrest and apoptosis in response to DNA damage and cellular stress, and thereby plays a role in protecting cells from malignant transformation. The E3 ubiquitin ligase HDM2 negatively regulates p53 function through a direct binding interaction that neutralizes p53-dependent transactivation activity, mediates p53 export from the nucleus, and targets p53 for degradation via the ubiquitin-proteasome pathway. HDMX (also called HDM4) is a structural homolog of HMD2, which also acts as a negative regulator of p53 primarily through binding to p53 transactivator domain. Overexpression of either HMD2 or HMDX has been linked to several malignancies (Marine, Dyer et al. 2007; Wahl and Wade 2009).

The region of p53 responsible for binding to HDM2 and HDMX has been mapped to the N-terminal transactivation domain of human p53 protein ($p53_{15-29}$). This domain encompasses a 15-residue sequence (SQETFSDLWKLL-PEN (SEQ ID NO:1) which forms an amphipatic α-helix of approximately 2.5 turns upon binding to HDM2 (or HDMX) (Kussie, Gorina et al. 1996; Popowicz, Czarna et al. 2008). Three residues within this HDM2/X-binding domain of p53, namely F19, W23, and L26, are involved in the interaction with HDM2 and HDMX as established based on mutagenesis studies (Kussie, Gorina et al. 1996; Popowicz, Czarna et al. 2008). A number of other linear p53-related peptides that carry the triad of cofacial i/i+4/i+7 amino acid residues known to be involved in p53 interaction with HDM2/X have been identified by phage display, which include the linear peptide PMI ($T^1$SFAEYWNLLSP$^{12}$, SEQ ID NO:2) and the linear peptide PDI ($L^1$TFEHYWAQLTS$^{12}$, SEQ ID NO:3) reported by Pazgier et al. (Pazgier, Liu et al. 2009).

A reduction or loss of p53 activity as a result of a deletion or mutation of the p53 gene or of overexpression of HDM2 or HMDX, has been identified as factor underlying the development and progression of several human malignancies (Marine, Dyer et al. 2007; Wahl and Wade 2009). Tumors that express wild-type p53 remain sensitive to pharmacologic agents that stabilize or increase the concentration of active p53. Accordingly, reactivation of p53 activity through chemical inhibition of the p53-HDM2 interaction has been recognized as a valid approach to promote apoptosis in cancer cells both in vitro and in vivo (Marine, Dyer et al. 2007; Wahl and Wade 2009). Furthermore, since HDM2 and HMDX are both involved in the negative regulation of p53 activity, dual inhibition of HDM2/X has emerged as a particularly attractive strategy for anticancer therapy (Hu, Gilkes et al. 2006; Wade, Wong et al. 2006). Furthermore, since most of small-molecule inhibitors of HDM2 fail to potently interfere with p53:HDMX interaction due to subtle differences in the p53 binding clefts of these protein homologs (Popowicz, Czarna et al. 2007), compounds that are capable of dual HDM2/X inhibition are of high interest as potential anticancer agents (Bernal, Wade et al. 2010; Brown, Quah et al. 2013).

In some embodiments, novel macrocyclic α-helical peptidomimetics are prepared according to the methods disclosed herein in order to generate compounds that can effectively interfere with the p53-HDM2 and p53-HDMX protein-protein interaction, these compounds being referred to herein as "p53 macrocyclic peptidomimetics". These novel HDM2/X inhibitors are useful for many applications, including, but not limited to, the therapeutic treatment of malignancies caused by overexpression of HDM2 or HDMX or by a reduced activity of p53.

In an embodiment, p53 macrocyclic peptidomimetics are provided that are able to disrupt the protein-protein interactions between p53 and HMD2, p53 and HDMX, or p53 and both HDM2 and HDMX proteins. These p53 macrocyclic peptidomimetics can be used for therapeutic applications, for example to treat cancers and other disorders in humans and non-human mammals, wherein the cancers or other disorders are characterized by an undesirably low level or a low activity of p53, and/or to treat cancers and other disorders characterized by an undesirably high level of activity of HDM2 or HDMX. These p53 macrocyclic peptidomimetics may also be useful for treatment of any disorder in humans or non-human mammals associated with disrupted regulation of the p53 transcriptional pathway, leading to conditions of excess cell survival and proliferation such as cancer and autoimmunity, in addition to conditions of inappropriate cell cycle arrest and apoptosis such as neurodegeneration and immunedeficiencies. In some embodiments, these p53 macrocyclic peptidomimetics bind to HDM2 (e.g., GenBank Accession No.: 228952; GL228952) and/or HDMX (also referred to as HDM4; GenBank Accession No.: 88702791; GL88702791).

As used herein, the term "p53/HDM2/HDMX-related disease" refers to any human disease or disorder which is caused, at least in part, by an abnormal (i.e. abnormally high or abnormally low) activity or expression level of the human protein p53, HDM2 or HMDX.

As used herein, the term "treatment" is defined as the application or administration of a therapeutic agent to a patient (including, but not limited to, a human or a non-human mammal), or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease.

Accordingly, p53 macrocyclic peptidomimetics of Formula (VII) are provided for use in the treatment of a p53/HDM2/HDMX-related disease in a human (or a non-human mammal) subject:

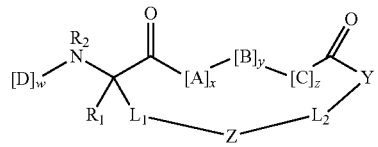
(VII)

wherein:
each A, C, and D is independently a natural or non-natural amino acid, and the terminal D optionally comprises a capping group;
B is a natural amino acid, non-natural amino acid, an amino acid comprising at least one additional methylene groups between the amino and carboxyl group, an amino acid comprising an amino group which is a secondary or tertiary amine, an amino acid comprising a carboxy group replaced by an ester, [—NHN($R_3$)C(O)—], [—NH-$L_3$-$SO_2$—], or [—NH-$L_3$-];
Y is —NH—, —N($R_4$)—, —NHN($R_4$)—, —NH—O—, —O—, or —S—;
—Z is —SCH$R_6$—, —CH$R_6$S—, —C=C—, —N($R_5$)CO—, —CON($R_6$)—, —C($R_5$)=N($R_6$)—, —CH($R_5$)—NH($R_6$)—, —C($R_5$)=N—O—, —CH($R_5$)—NH—O—, —C($R_5$)=N—NH($R_6$)—, —CH($R_5$)—NH—NH($R_6$)—, or a triazole group;
$L_1$, $L_2$, and $L_3$ are independently aliphatic, aryl, substituted aliphatic, substituted aryl, heteroatom-containing aliphatic, heteroatom-containing aryl, substituted heteroatom-containing aliphatic, substituted heteroatom-containing aryl groups, each being unsubstituted or substituted with $R_7$;
$R_1$, $R_2$, $R_3$, $R_4$, $R_5$, and $R_6$ are independently —H, aliphatic, substituted aliphatic, aryl, or substituted aryl group;
each $R_7$ is independently —H, an aliphatic, substituted aliphatic, an aryl, a substituted aryl group;
x is an integer from 0-10;
y is an integer from 0-10;
z is an integer from 0-10;
w is an integer from 1-1000;

In some embodiments, the peptide sequence comprised in the p53 macrocyclic peptidomimetic molecule is derived from the transactivation domain of the p53 protein (SEQ ID NO:1). In other embodiments, the peptide sequence comprised in the p53 macrocyclic peptidomimetic molecule is derived from the p53-related polypeptides of SEQ ID NO:2 and SEQ ID NO:3.

In some embodiments, the p53 macrocyclic peptidomimetic molecule comprises an amino acid sequence which is at least about 50%, 60%, 80%, 90%, or 95% identical to the polypeptide sequences corresponding to SEQ ID NOS: 1, 2, and 3.

In some embodiments, the p53 macrocyclic peptidomimetic molecule comprises an amino acid sequence set forth in TABLES 1, 2, 3 and/or 4.

TABLE 1

| | | | | | | | | | AMINO ACID SEQUENCE | | | | | | | | SEQ ID NO. |
|---|---|---|---|---|---|---|---|---|---|---|---|---|---|---|---|---|---|
| | | Ser | Gln | Glu | Thr | Phe | Ser | Asp | Leu | Trp | Lys | Leu | Leu | Pro | Glu | Pro | 1 |
| | | | | Thr | Ser | Phe | Ala | Glu | Tyr | Trp | Asn | Leu | Leu | Ser | Pro | | 2 |
| | | | | Leu | Thr | Phe | Glu | His | Tyr | Trp | Ala | Gln | Leu | Thr | Ser | | 3 |
| Ac- | X | Ser | Gln | Thr | Phe | Ser | Asn | Leu/Tyr | Trp/6Cl-Trp | Arg | Leu | Leu | Pro/Ala | | | | 4 |
| Ac- | Gln | X | Gln | Thr | Phe | Ser | Asn | Leu/Tyr | Trp/6Cl-Trp | Arg | Leu | Leu | Pro/Ala | | | | 5 |
| Ac- | Gln | Ser | X | Thr | Phe | Ser | Asn | Leu/Tyr | Trp/6Cl-Trp | Arg | Leu | Leu | Pro/Ala | | | | 6 |
| Ac- | Gln | Ser | Gln | X | Phe | Ser | Asn | Leu/Tyr | Trp/6Cl-Trp | Arg | Leu | Leu | Pro/Ala | | | | 7 |
| Ac- | Gln | Ser | Gln | Thr | X | Ser | Asn | Leu/Tyr | Trp/6Cl-Trp | Arg | Leu | Leu | Pro/Ala | | | | 8 |
| Ac- | Gln | Ser | Gln | Thr | Phe | X | Asn | Leu/Tyr | Trp/6Cl-Trp | Arg | Leu | Leu | Pro/Ala | | | | 9 |
| Ac- | Gln | Ser | Gln | Thr | Phe | Ser | X | Leu/Tyr | Trp/6Cl-Trp | Arg | Leu | Leu | Pro/Ala | | | | 10 |
| Ac- | Gln | Ser | Gln | Thr | Phe | Ser | Asn | X | Trp/6Cl-Trp | Arg | Leu | Leu | Pro/Ala | | | | 11 |
| Ac- | Gln | Ser | Gln | Thr | Phe | Ser | Asn | Leu/Tyr | Trp/6Cl-Trp | X | Leu | Leu | Pro/Ala | | | | 11 |

Aib = 2-aminoisobutyric acid;
Ac3c = 1-aminocyclopropanecarboxylic acid;
Cba = 2-amino-3-cyclobutylpropanoic acid.
X = amino acid linked to carboxy terminus via macrocycle-forming linker

TABLE 2

| | | | | | AMINO ACID SEQUENCE | | | | | | | | SEQ ID NO. |
|---|---|---|---|---|---|---|---|---|---|---|---|---|---|
| Ac- | X | Ser | Phe | Ala/Glu/Met | Glu/Gln/Ala/His | Tyr | Trp/6Cl-Trp | Asn/Ala | Leu/Ac3c/Gln | Leu/Cba | Ala/Gly | | 12 |
| Ac- | Thr/Leu | X | Phe | Ala/Glu/Met | Glu/Gln/Ala/His | Tyr | Trp/6Cl-Trp | Asn/Ala | Leu/Ac3c/Gln | Leu/Cba | Ala/Gly | | 13 |
| Ac- | Thr/Leu | Ser | Phe | X | Glu/Gln/Ala/His | Tyr | Trp/6Cl-Trp | Asn/Ala | Leu/Ac3c/Gln | Leu/Cba | Ala/Gly | | 14 |
| Ac- | Thr/Leu | Ser | Phe | Ala/Glu/Met | X | Tyr | Trp/6Cl-Trp | Asn/Ala | Leu/Ac3c/Gln | Leu/Cba | Ala/Gly | | 15 |
| Ac- | Thr/Leu | Ser | Phe | Ala/Glu/Met | Glu/Gln/Ala/His | X | Trp/6Cl-Trp | Asn/Ala | Leu/Ac3c/Gln | Leu/Cba | Ala/Gly | | 16 |
| Ac- | Thr/Leu | Ser | Phe | Ala/Glu/Met | Glu/Gln/Ala/His | Tyr | Trp/6Cl-Trp | X | Leu/Ac3c/Gln | Leu/Cba | Ala/Gly | | 17 |

Aib = 2-aminoisobutyric acid;
Ac3c = 1-aminocyclopropanecarboxylic acid;
Cba = 2-amino-3-cyclobutylpropanoic acid.
X = amino acid linked to carboxy terminus via macrocycle-forming linker

TABLE 3

| | | | | | AMINO ACID SEQUENCE | | | | | | | SEQ ID NO. |
|---|---|---|---|---|---|---|---|---|---|---|---|---|
| Ac- | X | Thr | Phe | Glu/Met | Ala/His/Asn/Glu | Tyr | Trp/6Cl-Trp | Asn/Ala | Ac3c/Gln/Leu | Leu/Cba | Thr/Ala | 18 |
| Ac- | Leu/Gln | X | Phe | Glu/Met | Ala/His/Asn/Glu | Tyr | Trp/6Cl-Trp | Asn/Ala | Ac3c/Gln/Leu | Leu/Cba | Thr/Ala | 19 |
| Ac- | Leu/Gln | Thr | Phe | X | Ala/His/Asn/Glu | Tyr | Trp/6Cl-Trp | Asn/Ala | Ac3c/Gln/Leu | Leu/Cba | Thr/Ala | 20 |
| Ac- | Leu/Gln | Thr | Phe | Glu/Met | X | Tyr | Trp/6Cl-Trp | Asn/Ala | Ac3c/Gln/Leu | Leu/Cba | Thr/Ala | 21 |
| Ac- | Leu/Gln | Thr | Phe | Glu/Met | Ala/His/Asn/Glu | X | Trp/6Cl-Trp | Asn/Ala | Ac3c/Gln/Leu | Leu/Cba | Thr/Ala | 22 |
| Ac- | Leu/Gln | Thr | Phe | Glu/Met | Ala/His/Asn/Glu | Tyr | Trp/6Cl-Trp | X | Ac3c/Gln/Leu | Leu/Cba | Thr/Ala | 23 |
| Ac- | X | Thr | Phe | Glu/Met | Ala/His/Asn/Glu | Tyr | Trp/6Cl-Trp | Glu/Ala | Ac3c/Gln/Leu | Leu/Cba | | 24 |
| Ac- | Leu/Gln | X | Phe | Glu/Met | Ala/His/Asn/Glu | Tyr | Trp/6Cl-Trp | Glu/Ala | Ac3c/Gln/Leu | Leu/Cba | | 25 |
| Ac- | Leu/Gln | Thr | Phe | X | Ala/His/Asn/Glu | Tyr | Trp/6Cl-Trp | Glu/Ala | Ac3c/Gln/Leu | Leu/Cba | | 26 |
| Ac- | Leu/Gln | Thr | Phe | Glu/Met | X | Tyr | Trp/6Cl-Trp | Glu/Ala | Ac3c/Gln/Leu | Leu/Cba | | 27 |
| Ac- | Leu/Gln | Thr | Phe | Glu/Met | Ala/His/Asn/Glu | X | Trp/6Cl-Trp | Glu/Ala | Ac3c/Gln/Leu | Leu/Cba | | 28 |

Aib = 2-aminoisobutyric acid;
Ac3c = 1-aminocyclopropanecarboxylic acid;
Cba = 2-amino-3-cyclobutylpropanoic acid.
X = amino acid linked to carboxy terminus via macrocycle-forming linker

TABLE 4

| | | | | | AMINO ACID SEQUENCE | | | | | | SEQ ID NO. |
|---|---|---|---|---|---|---|---|---|---|---|---|
| Ac- | X | Phe | Met | Aib/His/Asn | Tyr | Trp/6Cl-Trp | Glu/Ala | Ac3c/Gln/Leu | Leu/Cba | Thr/Ala | 29 |
| | | Phe | X | Aib/His/Asn | Tyr | Trp/6Cl-Trp | Glu/Ala | Ac3c/Gln/Leu | Leu/Cba | Thr/Ala | 30 |
| | | Phe | Met | X | Tyr | Trp/6Cl-Trp | Glu/Ala | Ac3c/Gln/Leu | Leu/Cba | Thr/Ala | 31 |
| | | Phe | Met | Aib/His/Asn | X | Trp/6Cl-Trp | Glu/Ala | Ac3c/Gln/Leu | Leu/Cba | Thr/Ala | 32 |
| | | Phe | Met | Aib/His/Asn | Tyr | Trp/6Cl-Trp | X | Ac3c/Gln/Leu | Leu/Cba | Thr/Ala | 33 |
| Ac- | X | Phe | Met | Aib/His/Asn | Tyr | Trp/6Cl-Trp | Glu/Ala | Ac3c/Gln/Leu | Leu/Cba | | 34 |
| | | Phe | X | Aib/His/Asn | Tyr | Trp/6Cl-Trp | Glu/Ala | Ac3c/Gln/Leu | Leu/Cba | | 35 |
| | | Phe | Met | X | Tyr | Trp/6Cl-Trp | Glu/Ala | Ac3c/Gln/Leu | Leu/Cba | | 36 |
| | | Phe | Met | Aib/His/Asn | X | Trp/6Cl-Trp | Glu/Ala | Ac3c/Gln/Leu | Leu/Cba | | 37 |

Aib = 2-aminoisobutyric acid;
Ac3c = 1-aminocyclopropanecarboxylic acid;
Cba = 2-amino-3-cyclobutylpropanoic acid.
X = amino acid linked to carboxy terminus via macrocycle-forming linker In some embodiments, the p53 macrocyclic peptidomimetic molecule comprises an amino acid sequence which is at least about 50%, 60%, 80%, 90%, or 95% identical to any of the polypeptide sequences of SEQ ID NOS: 4 through 37.

In some embodiments, the p53 macrocyclic peptidomimetic molecule corresponds to a macrocyclic peptidomimetic molecule of general formula (VII), wherein the amino acid sequence is an amino acid sequence set forth in TABLES 1, 2, 3 and/or 4, and wherein the macrocycle-forming linker [-L$_1$-Z-L$_2$-Y-] connecting the residue X and the carboxy terminus of these amino acid sequences is from a group of macrocycle-forming linkers including, but not limited to,

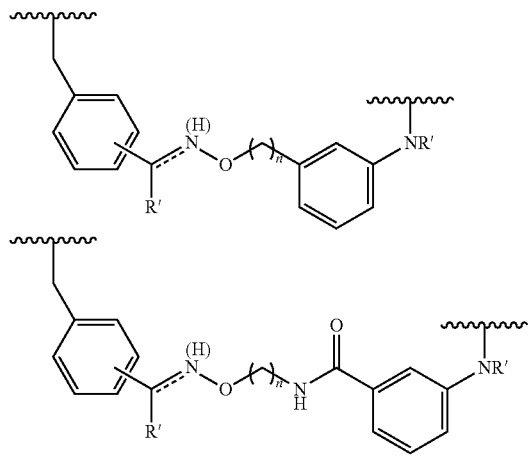

-continued

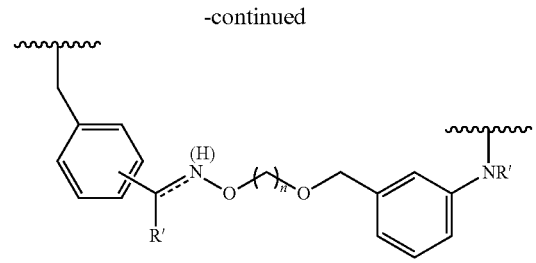

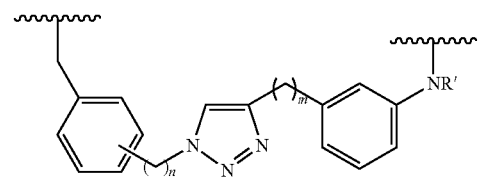

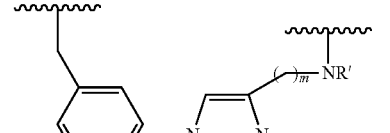

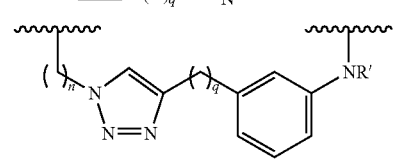

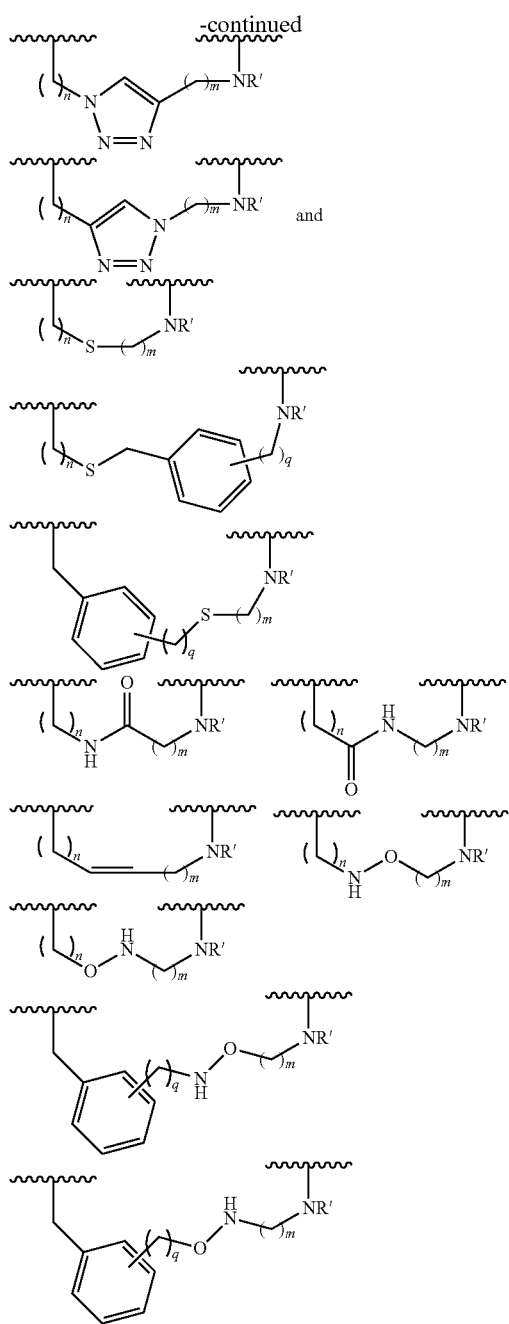

wherein
the symbol

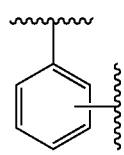

indicates an ortho-, meta- or para-disubstituted phenyl ring;
'm' and 'n' are each independently an integer number ranging from 1 to 10;
'q' is an integer number from 0 to 5; and
each R' is independently —H or —CH$_3$.

In some embodiments, the p53 macrocyclic peptidomimetic molecule corresponds to a compound of general formula (VII), wherein i) the amino acid sequence comprised in the p53 macrocyclic peptidomimetic molecule is at least at least about 50%, 60%, 80%, 90%, or 95% identical to the polypeptide sequences corresponding to SEQ ID NOS: 1 through 37.

ii) and the side-chain-to-C-terminus macrocyclization is mediated by an amino acid analog selected from a group of amino acid analogs including, but not limited to:

Group A amino acid analogs:

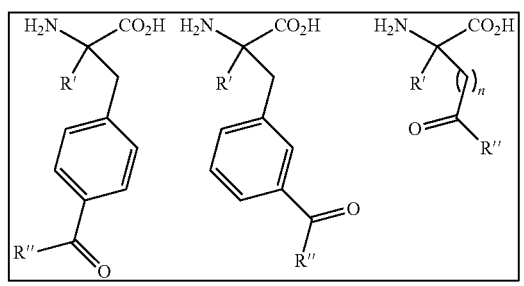

Group B amino acid analogs:

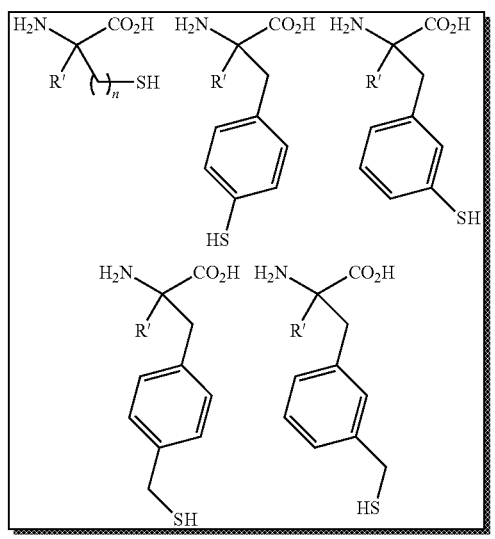

Group C amino acid analogs:

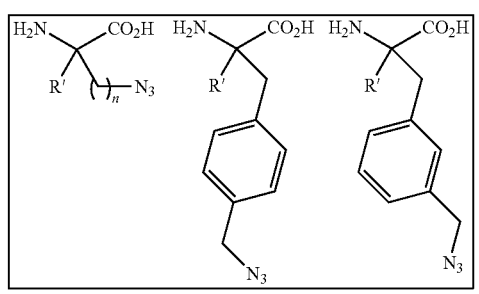

-continued

Group D amino acid analogs:

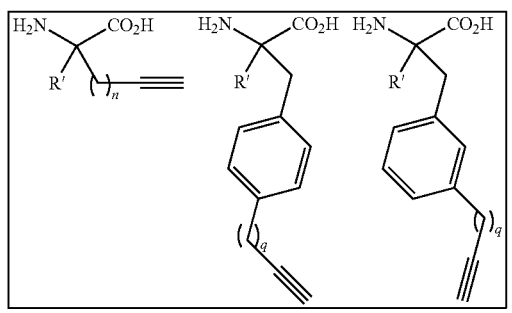

Group E amino acid analogs:

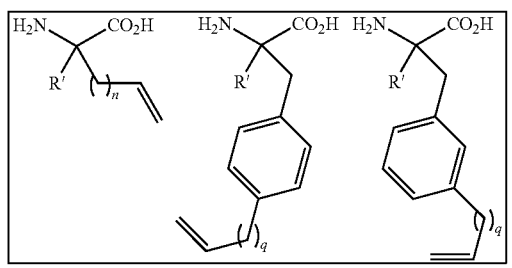

and by a compatible macrocycle-forming linker reagent selected from a group of macrocycle-forming linker reagents including, but not limited to:

Group A macrocycle-forming linker reagents:

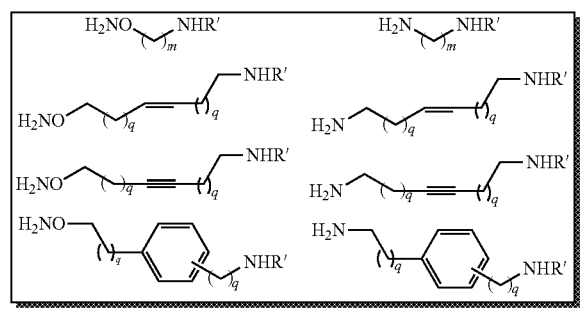

Group B macrocycle-forming linker reagents:

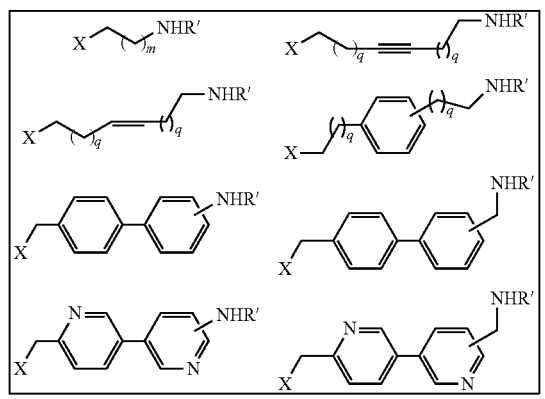

-continued

Group C macrocycle-forming reagents:

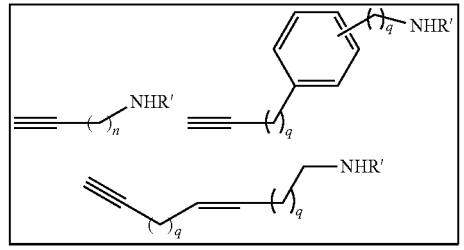

Group D macrocycle-forming reagents:

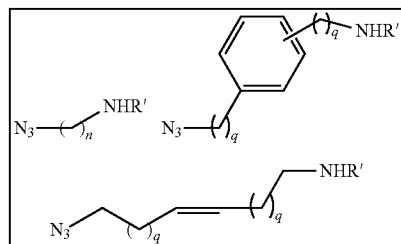

Group E macrocycle-forming reagents:

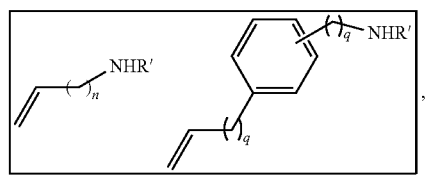

where in the selected amino acid analog and macrocycle-forming linker reagent,
the symbol

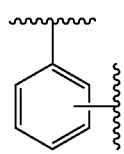

indicates an ortho-, meta- or para-disubstituted phenyl ring;
'm' and 'n' are independently an integer number ranging from 1 to 10;
'q' is an integer number from 0 to 5;
each R' is independently —H or —CH$_3$;
R" is —H, —CH$_3$ or —OH; and
X is —Cl, —Br, —I, —OTs, —OMs, or —OTf.

In some embodiments, the p53 macrocyclic peptidomimetic molecule of Formula (VII) comprises a fluorescent label, an affinity label, a radioisotopic label, a targeting agent, or a therapeutic agent.

In some embodiments, p53 macrocyclic peptidomimetics are provided that can be used for both the prophylactic or the therapeutic treatment of a subject that is susceptible to or has a disorder associated with aberrant expression or activity of the protein p53, HMD2, or HDMX. In some embodiments, this disorder is caused, at least in part, by an abnormal level of p53 or HMD2 or HDMX (e.g., overexpression or underexpression), or by the presence of p53 or HMD2 or HDMX having abnormal activity. As such, the reduction in the level and/or activity of p53 or HDM2 or HDMX, or the enhancement of the level and/or activity of p53 or HDM2 or HDMX, caused by the p53 macrocyclic peptidomimetic molecule can be useful to ameliorate or reduce the adverse symptoms of the disorder.

In some embodiments, the p53 macrocyclic peptidomimetic molecule is used to treat, prevent, and/or diagnose cancers and neoplastic conditions. As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. A metastatic tumor can arise from a multitude of primary tumor types, including but not limited to those of breast, lung, liver, colon and ovarian origin. "Pathologic hyperproliferative" cells occur in disease states characterized by malignant tumor growth. Examples of non-pathologic hyperproliferative cells include, but are not limited to, proliferation of cells associated with wound repair. Examples of cellular proliferative and/or differentiative disorders include, but are not limited to, cancer, e.g., carcinoma, sarcoma, or metastatic disorders. In some embodiments, the macrocyclic peptidomimetic molecules are novel therapeutic agents for controlling breast cancer, ovarian cancer, colon cancer, lung cancer, metastasis of such cancers and the like.

Examples of cancers or neoplastic conditions include, but are not limited to, a fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma.

Examples of proliferative disorders include, but are not limited to, hematopoietic neoplastic disorders. As used herein, the term "hematopoietic neoplastic disorders" includes, but is not limited to, diseases involving hyperplastic/neoplastic cells of hematopoietic origin, e.g., arising from myeloid, lymphoid or erythroid lineages, or precursor cells thereof. Diseases arising from poorly differentiated acute leukemias include, but are not limited to erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML); lymphoid malignancies include, but are not limited to acute lymphoblastic leukemia (ALL) which includes, but is not limited to, B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Examples of cellular proliferative and/or differentiative disorders of the breast include, but are not limited to, proliferative breast disease, e.g., epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast such as in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Examples of cellular proliferative and/or differentiative disorders of the lung include, but are not limited to, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Examples of cellular proliferative and/or differentiative disorders of the colon include, but are not limited to, non-neoplastic polyps, adenomas, familial syndromes, colorectal carcinogenesis, colorectal carcinoma, and carcinoid tumors.

Examples of cellular proliferative and/or differentiative disorders of the liver include, but are not limited to, nodular hyperplasias, adenomas, and malignant tumors, including primary carcinoma of the liver and metastatic tumors.

Examples of cellular proliferative and/or differentiative disorders of the ovary include, but are not limited to, ovarian tumors such as, tumors of coelomic epithelium, serous tumors, mucinous tumors, endometrioid tumors, clear cell adenocarcinoma, cystadenofibroma, Brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecomafibromas, androblastomas, hill cell tumors, and gonadoblastoma; and metastatic tumors such as Krukenberg tumors.

In other embodiments, the macrocyclic peptidomimetics described herein are used to treat, prevent or diagnose conditions characterized by overactive cell death or cellular death due to physiologic insult, etc. Some examples of conditions characterized by premature or unwanted cell death are or alternatively unwanted or excessive cellular proliferation include, but are not limited to hypocellular/hypoplastic, acellular/aplastic, or hypercellular/hyperplastic conditions. Some examples include hematologic disorders including but not limited to fanconi anemia, aplastic anemia, thalaessemia, congenital neutropenia, and myelodysplasia.

In other embodiments, the macrocyclic peptidomimetics disclosed herein that act to decrease apoptosis are used to treat disorders associated with an undesirable level of cell death. Thus, in some embodiments, the anti-apoptotic macrocyclic peptidomimetics are used to treat disorders such as those that lead to cell death associated with viral infection, e.g., infection associated with infection with human immunodeficiency virus (HIV), and neurological diseases associated with cell apoptosis. Such neurological disorders include Alzheimer's disease, Parkinson's disease, amyotrophic lateral sclerosis (ALS) retinitis pigmentosa, spinal muscular atrophy, and various forms of cerebellar degeneration. Gradual loss of neurons in these diseases does not induce an inflammatory response, and appears to be linked to abnormally increased levels of apoptosis.

In another embodiments, the p53 macrocyclic peptidomimetics described herein are used to treat, prevent or diagnose inflammatory disorders, which include, but are not limited to, autoimmune diseases. Examples of autoimmune diseases that are treated with the p53 peptidomimetics macrocycles described herein include, but are not limited to, acute disseminated encephalomyelitis (ADEM), Addison's disease, ankylosing spondylitis, antiphospholipid antibody syndrome (APS), autoimmune hemolytic anemia, autoimmune hepatitis, autoimmune inner ear disease, Bechet's disease, bullous pemphigoid, coeliac disease, Chagas disease, Churg-Strauss syndrome, chronic obstructive pulmonary disease (COPD), Crohn's disease, dermatomyositis, diabetes mellitus type 1, endometriosis, Goodpasture's syndrome, Graves' disease, Guillain-Barre syndrome (GBS), Hashimoto's disease, Hidradenitis suppurativa, idiopathic thrombocytopenic purpura, inflammatory bowel disease (IBD), interstitial cystitis, lupus erythematosus, morphea, multiple sclerosis, myasthenia gravis, narcolepsy, neuromyotonia, pemphigus vulgaris, pernicious anaemia, Polymyositis, polymyalgia rheumatica, primary biliary cirrhosis, psoriasis, rheumatoid arthritis, schizophrenia, scleroderma, Sjogren's syndrome, temporal arteritis (also known as "giant cell arteritis"), Takayasu's arteritis, Vasculitis, Vitiligo, and Wegener's granulomatosis.

Examples of other types of inflammatory disorders that can be treated with the p53 macrocyclic peptidomimetics described herein include, but are not limited to, allergy including allergic rhinitis/sinusitis, skin allergies (urticaria/hives, angioedema, atopic dermatitis), food allergies, drug allergies, insect allergies, and rare allergic disorders such as mastocytosis, asthma, arthritis including osteoarthritis, rheumatoid arthritis, and spondyloarthropathies, primary angitis of the CNS, sarcoidosis, organ transplant rejection, fibromyalgia, fibrosis, pancreatitis, and pelvic inflammatory disease.

Examples of cardiovascular disorders (e.g., inflammatory disorders) that can be treated or prevented with the p53 macrocyclic peptidomimetics described herein include, but are not limited to, aortic valve stenosis, atherosclerosis, myocardial infarction, stroke, thrombosis, aneurism, heart failure, ischemic heart disease, angina pectoris, sudden cardiac death, hypertensive heart disease; non-coronary vessel disease, such as arteriolosclerosis, small vessel disease, nephropathy, hypertriglyceridemia, hypercholesterolemia, hyperlipidemia, xanthomatosis, asthma, hypertension, emphysema and chronic pulmonary disease; or a cardiovascular condition associated with interventional procedures ("procedural vascular trauma"), such as restenosis following angioplasty, placement of a shunt, stent, synthetic or natural excision grafts, indwelling catheter, valve or other implantable devices.

Additionally, a method is provided of treating a p53/HDM2/HDMX-related disease in a subject comprising administering to the subject a p53 macrocyclic peptidomimetic molecule described herein. Additionally, a method is provided of treating a cancer in a subject comprising administering to the subject a p53 macrocyclic peptidomimetic molecule described herein.

The compounds provided herein may contain one or more (i.e., at least one) chiral centers. Accordingly, the compounds can be racemic mixtures, diastereomers, enantiomers, or mixtures enriched in one or more stereoisomer. When a group of substituents is disclosed herein, all the individual members of that group and all subgroups, including any isomers, enantiomers, and diastereomers are intended to be included in the disclosure. Additionally, all isotopic forms of the compounds disclosed herein are intended to be included in the disclosure. For example, it is understood that any one or more hydrogens in a molecule disclosed herein can be replaced with deuterium or tritium.

5.8 Pharmaceutical Compositions and Routes of Administration

The p53 macrocyclic peptidomimetics disclosed herein also include pharmaceutically acceptable derivatives or pro-drugs thereof. A "pharmaceutically acceptable derivative" means any pharmaceutically acceptable salt, ester, salt of an ester, pro-drug or other derivative of a compound disclosed herein which, upon administration to a recipient, is capable of providing (directly or indirectly) a compound disclosed herein. Particularly favored pharmaceutically acceptable derivatives are those that increase the bioavailability of the compounds disclosed herein when administered to a mammal (e.g., by increasing absorption into the blood of an orally administered compound) or which increases delivery of the active compound to a biological compartment (e.g., the brain or lymphatic system) relative to the parent species. Some pharmaceutically acceptable derivatives include a chemical group which increases aqueous solubility or active transport across the gastrointestinal mucosa.

In some embodiments, the p53 macrocyclic peptidomimetics disclosed herein are modified by covalently or non-covalently joining appropriate functional groups to enhance selective biological properties. Such modifications include those which increase biological penetration into a given biological compartment (e.g., blood, lymphatic system, central nervous system), increase oral availability, increase solubility to allow administration by injection, alter metabolism, and alter rate of excretion.

Pharmaceutically acceptable salts of the compounds include, but are not limited to, those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, phosphate, picrate, pivalate, propionate, salicylate, succinate, sulfate, tartrate, tosylate and undecanoate. Salts derived from appropriate bases include alkali metal (e.g., sodium), alkaline earth metal (e.g., magnesium), ammonium and N-(alkyl)$_4$+ salts.

For preparing pharmaceutical compositions from the compounds of the present disclosure, pharmaceutically acceptable carriers include either solid or liquid carriers. Solid form preparations include powders, tablets, pills, capsules, cachets, suppositories, and dispersible granules. A solid carrier can be one or more substances, which also acts as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa.

In powders, the carrier is a finely divided solid, which is in a mixture with the finely divided active component. In tablets, the active component is mixed with the carrier having the necessary binding properties in suitable proportions and compacted in the shape and size desired.

Suitable solid excipients are carbohydrate or protein fillers include, but are not limited to sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; as well as proteins such as gelatin and collagen. If desired, disintegrating or solubilizing agents are added, such as the cross-linked polyvinyl pyrrolidone, agar, alginic acid, or a salt thereof, such as sodium alginate.

Liquid form preparations include solutions, suspensions, and emulsions, for example, water or water/propylene glycol solutions. For parenteral injection, liquid preparations can be formulated in solution in aqueous polyethylene glycol solution. The term "parenteral" as used herein refers modes of administration including intravenous, intraarterial, intramuscular, intraperitoneal, intrasternal, and subcutaneous.

When the compositions disclosed herein comprise a combination of a macrocyclic peptidomimetic molecule and one or more additional therapeutic or prophylactic agents, both the macrocyclic peptidomimetic molecule and the additional agent should be present at dosage levels of between about 1 to 100%, and in some embodiments between about 5 to 95% or between 10% and 90% of the dosage normally administered in a monotherapy regimen. In some embodiments, the additional agents are administered separately, as part of a multiple dose regimen, from the compounds of the present disclosure. Alternatively, those agents are part of a single dosage form, mixed together with the compounds disclosed herein in a single composition.

Methods of administration of the p53 macrocyclic peptidomimetics disclosed herein include but are not limited to intradermal, intramuscular, intraperitoneal, intravenous, subcutaneous, intranasal, epidural, oral, sublingual, intracerebral, intravaginal, transdermal, rectal, by inhalation, or topical by application to ears, nose, eyes, or skin.

The terms and expression that are employed herein are used as terms of description and not of limitation, and there is no intention that in the use of such terms and expressions of excluding any equivalents of the features shown and described and portions thereof, but it is recognized that various modifications are possible within the scope of the subject matter disclosed and/or claimed herein. Thus, it should be understood that although embodiments and optional features are disclosed, modification and variation of the concepts disclosed may be resorted to those skilled in the art, and that such modifications and variations are considered to be within the scope of the subject matter disclosed and/or claimed herein.

Unless otherwise indicated, the disclosure is not limited to specific molecular structures, substituents, synthetic methods, reaction conditions, or the like, as such may vary. It is to be understood that the embodiments are not limited to particular compositions or biological systems, which can, of course, vary.

A skilled artisan will appreciate that starting materials, biological materials, reagents, synthetic methods, purification methods, analytical methods, assay methods, and biological methods other than those specifically exemplified can be employed in the practice of the compounds and methods disclosed herein. All art-known functional equivalents of any such materials and methods are intended to be included.

6. EXAMPLES

6.1 Example 1. Design of p53 macrocyclic peptidomimetics

A linear 12-mer peptide, called PMI (T$^1$SFAEYWNLLSP$^{12}$; SEQ ID NO: 2), was recently isolated via phage display by Pazgier et al. (Pazgier, Liu et al. 2009)). PMI carries the triad of cofacial i/i+4/i+7 amino acid residues known to be involved in p53 interaction with HDM2/X (Kussie, Gorina et al. 1996; Popowicz, Czarna et al. 2008) (i.e. Phe$^3$, Trp$^7$, and Leu$^{10}$ corresponding to Phe$^{19}$, Trp$^{23}$, and Leu$^{26}$ in p53, respectively), but binds both HDM2 and HDMX with greater affinity than the p53-derived peptide p53$_{(15-29)}$ (IC$_{50}$~30-40 nM vs. 200-300 nM, respectively) (Pazgier, Liu et al. 2009). Upon inspection of the available crystal structure of PMI/HDM2 complex (Pazgier, Liu et al. 2009) (FIG. 9A), two solvent-exposed residues, namely Thr$^1$ and Glu$^5$, were identified as two viable side-chain attachment points for generating p53 macrocyclic peptimimetics (FIG. 9B) according to the general method disclosed here (FIG. 1). In term of macrocyclization strategy, the side-chain-to-C-terminus macrocyclization procedure which is mediated by the amino acid analog para-acetyl-phenylalanine (pAcF) and by oxyamino/amino-thiol macrocycle-forming linker reagents such as those presented in FIG. 8 was chosen. Since Pro$^{12}$ in the PMI peptide did not appear to establish significant contacts with the HDM2 surface (Pazgier, Liu et al. 2009), the C-terminal attachment site for construction of the p53 macrocyclic peptidomimetics was chosen to lie after Ser$^{11}$, which was changed to Ala in order to further promote α-helix formation by the peptidomimetic molecule.

Analysis of models of the corresponding Thr1pAcF- and Glu5pAcF-containing precursor peptidomimetic molecules revealed that the distances between pAcF β-carbon atom and the carbonyl atom of the i+6 or i/i+10 Ala$^{11}$ residue, respectively, were about 13 and 17 Å. These distances are matched by the spanning distance (~14-17 Å, FIGS. 11B-11C) provided by macrocycle-forming linkers generated upon reaction of pAcF with macrocycle-forming linker reagents SP6 and SP8 (FIG. 8). Accordingly, a series of i/i+6(CO)- and i/i+10(CO)-linked p53 macrocyclic peptidomimetics were designed, which incorporate either SP6 (compounds P3 (SEQ ID NO. 38) and P7 (SEQ ID NO. 39), FIG. 10) or SP8 (compounds P4 (SEQ ID NO. 38) and P8 (SEQ ID NO. 39), FIG. 10) as part of the linker moiety connecting side-chain of pAcF to the C-terminus of the peptide sequence. As negative controls, macrocycles comprising the same amino sequence but incorporating the 'distance-mismatched' SP4-based linker (10 Å (FIG. 11A) vs. target distance of 13-17 Å, FIG. 9A) were also prepared. The resulting peptidomimetics correspond to compounds P5 (SEQ ID NO. 38) and P9 (SEQ ID NO. 39) in FIG. 10.

Upon identification of the i/i+10(CO)-linked p53 macrocyclic peptidomimetic P8 (SEQ ID NO. 39) as the most promising inhibitor of the p53-HMD2 and p53/HDMX interactions (see EXAMPLE 6), further optimization of this compound was then pursued by acetylation of the N-terminus (P8 (SEQ ID NO. 39)→P12 (SEQ ID NO. 39), FIG. 10), shortening of the peptide sequence (P12 (SEQ ID NO. 39)→P13 (SEQ ID NO. 12), FIG. 10), replacement of pAcF with meta-acetyl-phenylalanine (P13 (SEQ ID NO. 12)→P14 (SEQ ID NO. 12), FIG. 10), and variation of the amino acid sequence (P13 (SEQ ID NO. 12)→P15 (SEQ ID NO. 12), FIG. 10) and of the macrocycle-forming linker (P13 (SEQ ID NO. 12)→P17 (SEQ ID NO. 12), FIG. 10). As a result of these optimization efforts, a p53 macrocyclic peptidomimetic molecule with nanomolar inhibitory activity against HMD2 and HDMX (P15 (SEQ ID NO. 12), FIG. 10) was obtained, which also showed anticancer activity in cell-based studies.

This Example also demonstrates how the methods of the present disclosure can be applied to enable the design, development, and optimization of macrocyclic peptidomimetic molecules of a target α-helical protein binding motif of interest (e.g. p53 transactivation domain).

6.2 Example 2. Synthesis of Amino Acid Analogs

This Example demonstrates the synthesis of amino acid analogs of general formula (VI) for use in the preparation of macrocyclic peptidomimetic molecules. Specifically, this example demonstrates the synthesis of racemic and/or enantiopure amino acid analogs such as para-acetyl-phenylalanine (pAcF) and meta-acetyl-phenylalanine (mAcF), which are useful for preparation of macrocyclic peptidomimetic molecules such as those exemplified in FIGS. 3 and 4. In addition, this example demonstrates the synthesis of other types of amino acid analogs, such as amino acid analogs containing a side-chain alkynyl group (—C≡CH, e.g. OpgY) or a side-chain sulphydryl group (—SH, e.g. AmmF and MeaF), which can be useful for the preparation of macrocyclic peptidomimetic molecules constrained by alternative type of linkers as encompassed by the various embodiments of the present disclosure. Furthermore, this example demonstrates the synthesis of amino acids analogs (e.g. 6-chloro-trypthophan) which can be incorporated within the peptidic backbone of the macrocyclic peptidomimetic molecule, in order to modulate the properties of these compounds (e.g. compounds P15-P19 (SEQ ID NO. 12) in FIG. 10).

Synthesis of Racemic pAcF and mAcF

The synthesis of pAcF form was carried out according to a published procedure (Frost, Vitali et al. 2013). Racemic mAcF was prepared using an identical protocol but starting from 3-acetyl-toluene.

Synthesis of Enatiopure N-Fmoc pAcF (and mAcF)

Figures 5A, 5B:
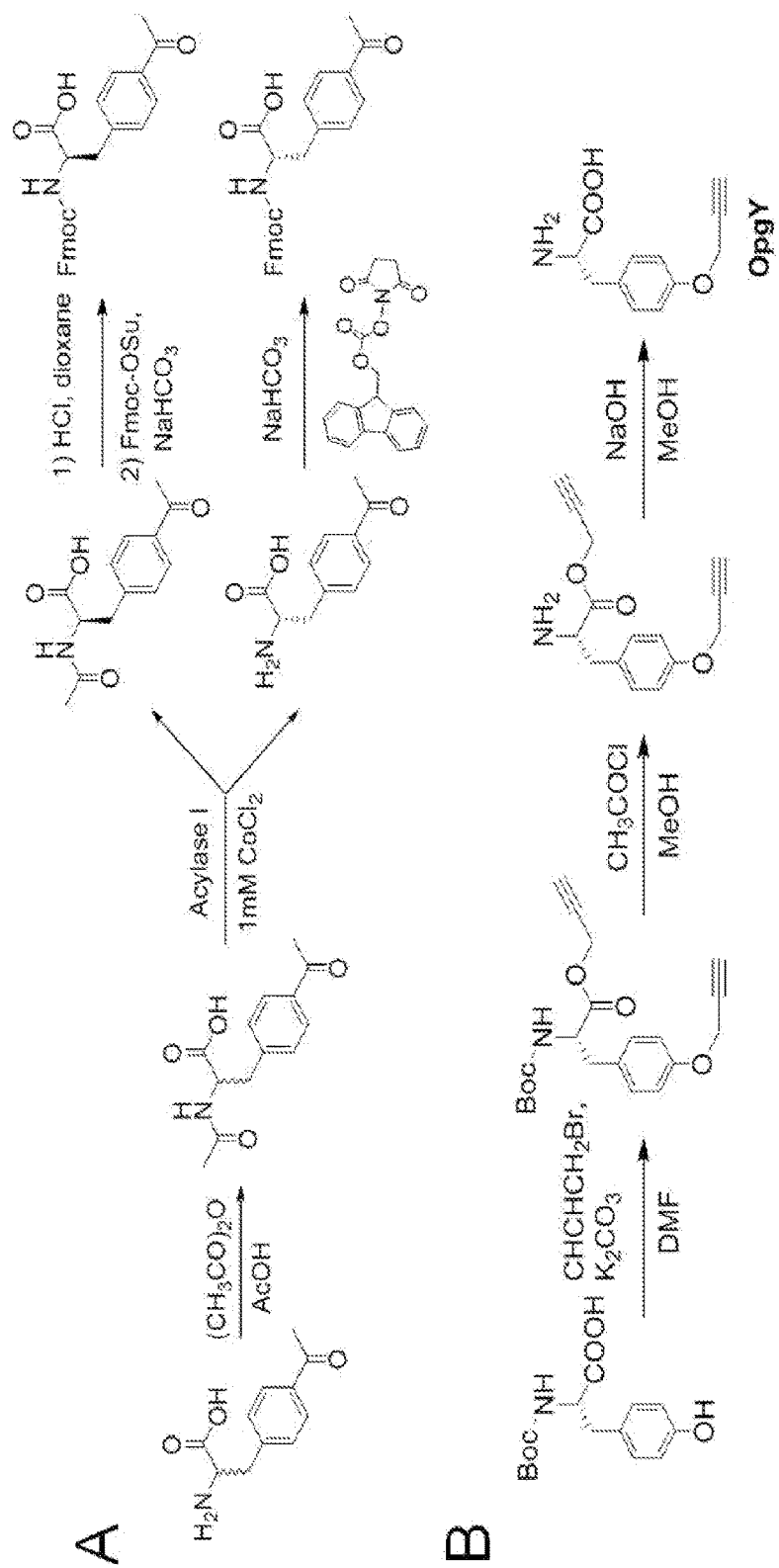

This compound was synthesized according to the procedure described in FIG. 5A. Racemic p-acetylphenylalanine (1 g, 4.83 mmol, 1 eq) was dissolved in acetic acid (20 mL) to which acetic anhydride was added (4.52 mL, mmol, 10 eq). The reaction was stirred at room temperature for 2 h, followed by removal of the solvent by evaporation. The crude product was redissolved in phosphate buffer (50 mL) containing 1 mM $CoCl_2 \cdot 6H_2O$ at pH 8.0, followed by addition of acylase I (500 mg). The reaction was stirred at 37° C. for 24 h with occasional adjustment of the pH to 8.0 with LiOH. The reaction mixture was heated to 60° C. for 5 min, cooled to room temperature and filtered through celite. The filtrate was acidified to pH ~3 using HCl and then extracted with EtOAc. The aqueous layer was lyophilized and used as crude product (410 mg L-enantiomer, yield ~82%) for the next reaction. L-p-acetyl-phenylalanine (410 mg, 1.98 mmol, 1 eq) was dissolved in a water/acetone mixture (1:1, v/v) to which $NaHCO_3$ (332.6 mg, 3.96 mmol, 2 eq) was added. Fmoc-OSu (735.4 mg, 2.18 mmol, 1.1 eq) was dissolved in acetone and added to the reaction mixture portion wise over the course of 3 h. Upon completion of the reaction, acetone was remove by evaporation and the aqueous layer acidified with acetic acid to pH ~3 followed by EtOAc extraction. The organic layers were combined, dried over sodium sulfate and evaporated. The crude product was purified with flash column chromatography and solvent system hexanes:EtOAc:AcOH (10:9:1) to yield pure Fmoc-p-acetyl-L-phenylalanine (832.7 mg, 98%). $^1$H NMR (500 MHz, $CD_3OD$), δ2.57 (s, 3H), 3.22-3.41 (m, 2H), 4.45 (t, 1H), 7.3-7.55 (m, 8H), 7.88 (d, 2H), 7.98 (d, 2H). MS (ESI) calculated for $C_{26}H_{23}NO_5$ $[M+H]^+$: m/z 429.16, found 429.4. An identical procedure was applied to obtain Fmoc-m-acetyl-L-phenylalanine.

Synthesis of O-Propargyl-Tyrosine (OpgY)

This compound was synthesized according to the procedure described in FIG. 5B. L-N-Boc-tyrosine (6.0 g, 21.0 mmol) and potassium carbonate (9.0 g, 63.0 mmol) were added to a reaction flask containing anhydrous DMF (30 mL). Propargyl bromide (6.3 ml, 63.0 mmol) was added and the reaction mixture stirred at room temperature for 20 hours. The resulting doubly alkylated product was extracted with diethyl ether (yellow oil, 6.8 g, 91%) and directly used for the next step. This intermediate (6.8 g, 19.04 mmol) was added to a mixture of acetyl chloride (21 mL) in methanol (180 mL) at 0° C. for 4 hours. The resulting intermediate (4.9 g, 19.04 mmol) was then added to a mixture of 2 N NaOH (42 mL) and methanol (30 mL) and the mixture stirred at room temperature. Upon complete hydrolysis as determined by TLC (2 hours), the pH was adjusted to 7.0 with concentrated HCl and the mixture was stirred overnight at 4° C. The precipitate was filtered, washed with cold water, and dried under reduced pressure overnight, yielding OpgY in 98% purity as a white powder (3.3 g, 80%). 1H NMR (400 MHz, D2O) δ 2.78 (s, 2H), 2.94 (dd, J=6.8, 22.4 Hz, 1H), 3.08 (dd, J=9.6, 20 Hz, 1H), 3.81 (dd, J=2.0, 12.8 Hz, 1H), 6.92 (d, J=8.8 Hz, 2H), 7.13 (d, J=8.4 Hz, 2H); 13C NMR (100 MHz, D2O) δ 35.4, 56.0, 76.6, 78.7, 115.6, 128.5, 130.6, 156.1, 173.9. MS (ESI) calcd for C12H13NO3 [M+H]+: m/z 220.1; found: 220.3.

Synthesis of 2-amino-3-(3-amino-4-(mercaptomethyl)phenyl)propanoic acid (AmmF)

Figure 5C:
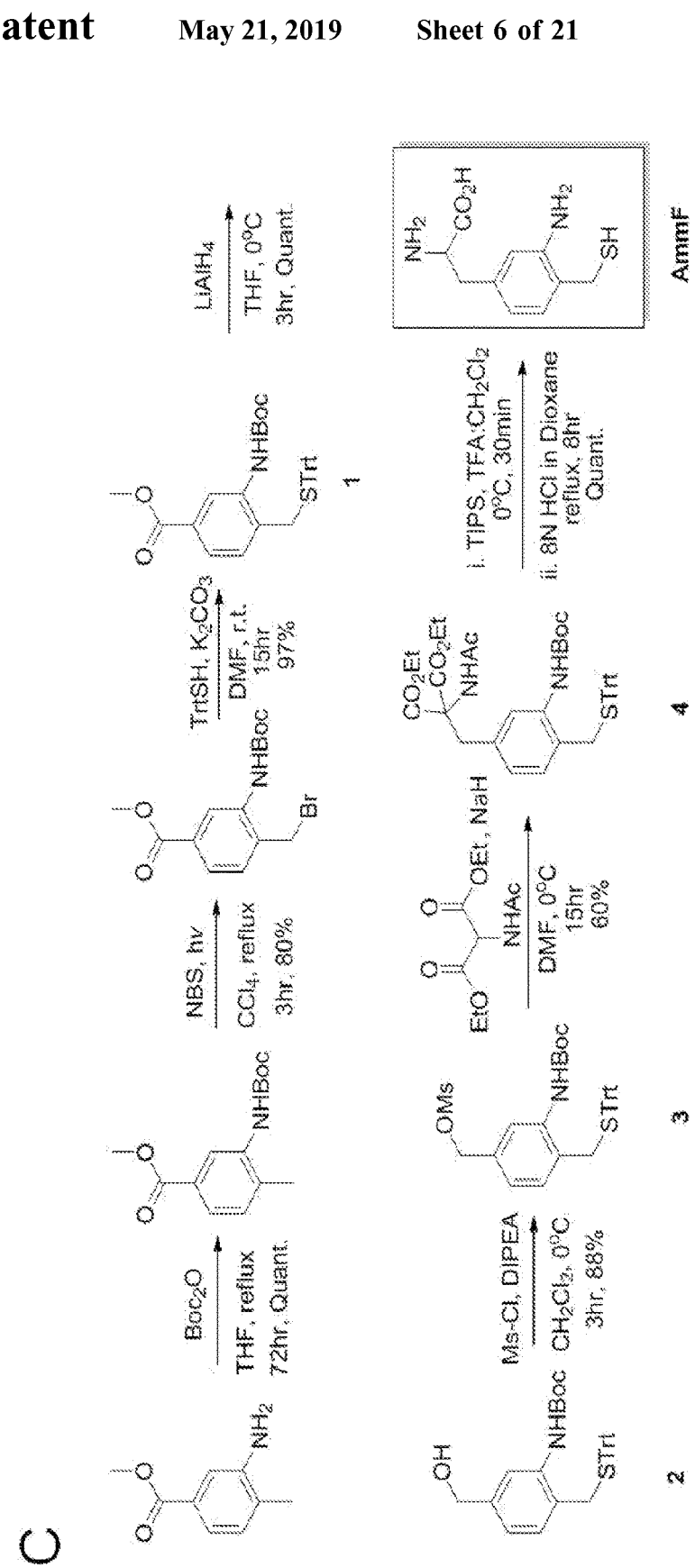

This compound was synthesized according to the synthetic scheme described in FIG. 5C. Starting from compound 1 (Frost, Vitali et al. 2013), this compound (20.32 g 1, 48 mmol) was dissolved in anhydrous THF (400 mL), then the solution was cooled to 0° C. A solution of $LiAlH_4$ in THF (1 M, 52.8 mL, 52.8 mmol, 1.1 equiv) was added slowly. The reaction mixture was stirred under argon at 0° C. for 3 h, the reaction was quenched by slow addition of cold $H_2O$ (3 mL) and 4N NaOH (aq) (1 mL) at 0° C., then the mixture was stirred for 10 min at room temperature. The mixture was concentrated under reduced pressure, suspended in EtOAc/sat. $NaHCO_3$ (10:1, 330 mL), then filtered through celite. The filtrate was washed once with saturated $NaHCO_3$, then with brine. The organic layer was dried with anhydrous $MgSO_4$, and volatiles were removed to afford a yellow solid, which was purified by flash column chromatography (silica gel, hexanes/EtOAc 7:3) to afford N-Boc-S-trityl-3-amino-4-(mercaptomethyl)benzyl alcohol (2) as a yellow oil (18 g, 95% yield). $^1$H NMR (CDCl$_3$, 500 MHz): δ 7.78 (s, 1H), 7.49 (d, J=7.3 Hz, 5H), 7.34 (t, J=7.7 Hz, 5H), 7.26 (t, J=3.0 Hz, 5H), 7.13 (d, J=7.8 Hz, 1H), 7.01 (d, J=7.8 Hz, 1H), 6.73 (s, 1H), 4.63 (s, 2H), 3.17 (s, 2H), 1.54 ppm (s, 9H); MS (ESI): calcd for $C_{32}H_{33}NO_3S$: 534.68 [M+Na]$^+$; found: 535.64. 2 (9.3 g, 18.19 mmol) was dissolved in anhydrous CH$_2$Cl$_2$ (100 mL), and the solution was cooled to 0° C. Methanesulfonylchloride (1.8 mL, 23.66 mmol, 1.3 equiv) and N,N-diisopropylethylamine (DIPEA; 4.2 mL, 23.66 mmol, 1.3 equiv) were added, and the reaction mixture was stirred under argon at 0° C. for 2 h. The mixture was then dissolved in CH$_2$Cl$_2$, washed twice with saturated NaHCO$_3$ (aq), and then once with brine. The organic layer was dried over anhydrous MgSO$_4$, and volatiles were removed to afford compound 3 as a yellow solid (9.42 g, 88% yield). The material was carried forward without further purification. $^1$H NMR (CDCl$_3$, 500 MHz): δ 7.88 (s, 1H), 7.49 (d, J=7.3 Hz, 5H), 7.34 (t, J=7.7 Hz, 5H), 7.26 (d, J=14.6 Hz, 5H), 7.16 (d, J=7.8 Hz, 1H), 7.04 (d, J=9.5 Hz, 1H), 6.75 (s, 1H), 5.18 (s, 2H), 3.17 (s, 2H), 2.90 (s, 3H), 1.54 ppm (s, 9H); MS (ESI): calcd for $C_{33}H_{35}NO_5S_2$: 612.76 [M+Na]$^+$; found: 612.04. To a dry, argon-filled round-bottom flask was added compound 3 (9.42 g) and diethylacetamidomalonate (4.52 g, 20.8 mmol, 1.3 eq). This mixture was dissolved in 100 mL anhydrous DMF and then cooled to 0° C. NaH (60% in mineral oil dispersion) (0.84 g, 20.8 mmol, 1.3 eq) was then added and the reaction mixture stirred under argon for 15 hours at 0° C. Upon completion, the reaction was concentrated to 10 mL and extracted with 350 mL CH$_2$Cl$_2$, yielding compound 5 as a white solid after flash chromatography (5.4 g, 60% yield). $^1$H NMR (500 MHz, CDCl$_3$) δ=7.52 (s, 1H), 7.48 (d, J=8 Hz, 6H), 7.32 (t, J=7.5 Hz, 6H), 7.23 (t, J=7.5 Hz, 3H), 7.01 (d, J=8 Hz, 1H), 6.68 (s, 1H), 6.63 (d, J=7.5 Hz, 1H), 6.57 (s, 1H), 4.26 (q, J=7.5 Hz, 4H), 3.58 (s, 2H), 3.12 (s, 2H), 2.06 (s, 3H), 1.52 (s, 9H), 1.27 ppm (t, J=7 Hz, 6H); MS (ESI): calcd for $C_{41}H_{46}N_2O_7S$: 733.89 [M+Na]$^+$; found: 733.22. Compound 4 (5.4 g, 7.6 mmol, 1 eq) was added to a dry, argon-filled 250 mL round-bottom flask and dissolved in 70 mL anhydrous dichloromethane. To the solution tri-isopropylsilane (3.88 mL, 19 mmol, 2.5 eq) was added and the reaction mixture was cooled in a ice bath. TFA (18 mL) was slowly added via a syringe and the reaction was left stirring under argon at 0° C. for 30 minutes. Upon completion, AmmF was isolated from the reaction mixture by flash chromatography (2.27 g, 100%). $^1$H NMR (500 MHz, D$_2$O) δ 7.54 (d, J=10 Hz, 1H), 7.41-7.30 (m, 2H), 4.31 (t, J=5 Hz, 1H), 3.88 (s, 2H), 3.36-3.27 ppm (m, 2H); $^{13}$C NMR (126 MHz, D$_2$O) δ=171.57, 135.46, 134.41, 131.42, 130.60, 128.73, 124.78, 54.29, 35.01, 23.12 ppm; MS (ESI): calcd for $C_{10}H_{14}N_2O_2S$: 227.08 [M+H]$^+$; found: 226.98.

Synthesis of 2-amino-3-(3-((2-mercaptoethyl)amino)phenyl)propanoic acid (MeaF)

Figure 5D:
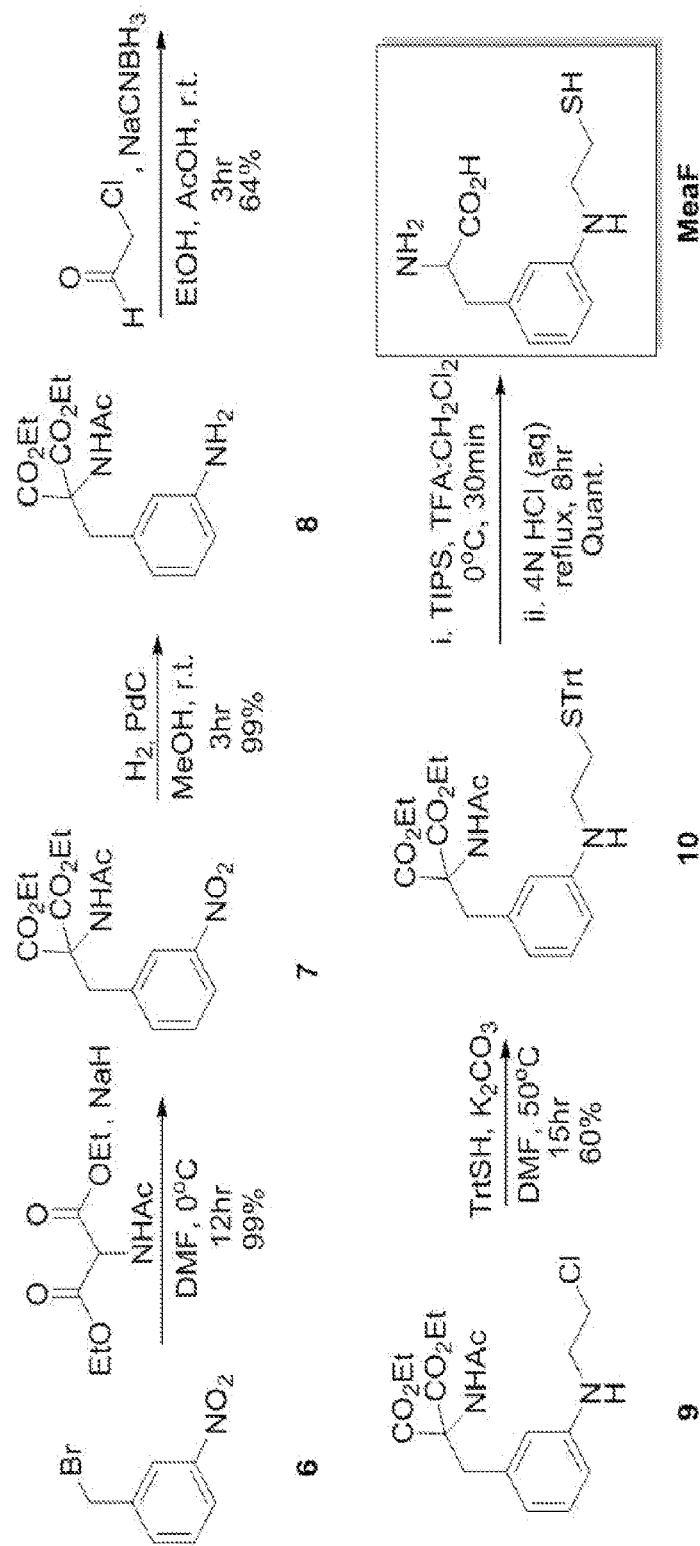

This compound was synthesized according to the synthetic scheme described in FIG. 5D. To obtain intermediate 7, NaH (60% dispersion in mineral oil) (1.11 g, 27.7 mmol, 1.2 eq) was added to a dry, argon-filled round bottom flask and dissolved in 150 mL anhydrous DMF. The flask was cooled to 0° C. and to the solution was added diethyl acetomidomalonate (5.53 g, 25.5 mmol, 1.1 eq). After five minutes, compound 6 (5 g, 23.14 mmol, 1 eq) was added. The reaction proceeded under argon at 0° C. for 16 hours. After extraction, 7 was obtained as a white solid (8 g, 98% yield). $^1$H NMR (400 MHz, CDCl$_3$) δ=8.12 (d, J=8 Hz, 1H), 7.90 (s, 1H), 7.46, (t, J=7.6 Hz, 1H), 7.36 (d, J=7.2 Hz, 1H), 6.61 (s, 1H), 4.27 (q, J=8 Hz, 4H), 3.78 (s, 2H), 2.39 (s, 3H), 1.48 ppm (t, J=6.8 Hz, 6H); MS (ESI): calcd for $C_{16}H_{20}N_2O_7$: 375.34 [M+Na]$^+$; found: 375.85. To compound 7 (5 g, 14.2 mmol, 1 eq), 1 g Pd/C was added in an argon-filled flask and the flask. 115 mL degassed methanol was added and the reaction mixture was sparged with H$_2$ for for 3 h at r.t. After extraction, compound 8 was obtained as a off-white solid (4.45 g, 97%). $^1$H NMR (500 MHz, CDCl$_3$) δ=8.12 (d, J=8.5 Hz, 1H), 7.90 (s, 1H), 7.45 (t, J=7.5 Hz, 1H), 7.36 (d, J=7.5 Hz, 1H), 6.55 (s, 1H), 4.29 (q, J=7 Hz, 4H), 3.78 (s, 2H), 2.06 (s, 1H), 1.32 ppm (t, J=7 Hz, 6H); MS (ESI): calcd for $C_{16}H_{22}N_2O_5$: 345.36 [M+Na]$^+$; found: 345.19. Compound 8 (4.5 g, 14 mmol, 1 eq) was added to a round bottom flask and dissolved in 90 mL ethanol. NaCNBH$_3$ (0.97 g, 15.4 mmol, 1.1 eq) was added and the mixture was sonicated to aid solubility. Chloroacetaldehyde (2.7 mL, 15.4 mmol, 1.1 eq) was added followed by glacial acetic acid (0.81 mL, 14 mmol, 1 eq). The reaction was run at r.t. under argon for 4 h. After purification by flash chromatography, compound 9 was obtained as a yellow oil (3.46 g, 9 mmol, 64.2% yield). $^1$H NMR (400 MHz, CDCl$_3$) δ=6.91 (t, J=8 Hz, 1H), 6.42 (d, J=8 Hz, 1H), 6.21 (d, J=7.6 Hz, 1H), 6.19 (s, 1H), 4.18-4.06 (m, 4H), 3.52 (t, J=6.4 Hz, 2H), 3.41-3.29 (m, 4H), 1.91 (s, 3H), 1.16 ppm (t, J=7.2 Hz, 6H); MS (ESI): calcd for $C_{18}H_{25}ClN_2O_5$: 407.86 [M+Na]$^+$; found: 407.33. Compound 9 (3.46 g, 9 mmol, 1 eq) was dissolved in 85 mL anhydrous DMF. To this was added triphenyl methylmercaptan (2.73 g, 9.9 mmol, 1.1 eq) followed by potassium carbonate (1.5 g, 10.8 mmol, 1.2 eq) and stirring at 50° C. for 12 h. The crude product purified on silica gel by flash chromatography to yield compound 10 as a yellow oil (3.38 g, 5.4 mmol, 60% yield). $^1$H NMR (500 MHz, CDCl$_3$) δ=7.39 (d, J=7.5 Hz, 6H), 7.26 (t, J=7.2 Hz, 3H), 7.22 (d, J=7.1 Hz, 6H), 7.19 (s, 1H), 7.00 (t, J=7.8 Hz, 1H), 6.51 (s, 1H), 6.32 (d, J=7.1 Hz, 2H), 6.13 (s, 1H), 4.25 (p, J=7.2 Hz, 4H), 3.53 (s, 2H), 2.98 (t, J=6.6 Hz, 2H), 2.47 (t, J=6.5 Hz, 2H), 1.96 (s, 3H), 1.27 ppm (t, J=7.1 Hz, 6H); MS (ESI): calcd for $C_{37}H_{40}N_2O_5S$: 647.80 [M+Na]$^+$; found: 647.91. Compound 10 (3.38 g, 5.4 mmol, 1 eq) was deprotected with 8 mL TFA for 20 minutes at 0° C. The dried residue was dissolved in 35 mL of 4N HCl (aq) and heated at reflux overnight. After purification, MeaF was obtained as a mixture of monomer and dimer (light-brown solid; 1.5 g, 5.4 mmol, 99.9%). $^1$H NMR (500 MHz, D$_6$-DMSO) δ=8.69 (s, 1H), 7.41-7.2 (m, 3H), 4.16 (t, J=10 Hz, 1H), 3.37 (t, J=5 Hz, 2H), 3.18-3.10 (m, 2H), 2.79 (t, J=10 Hz, 2H), 2.50 (s, 1H); $^{13}$C NMR (126 MHz, MeOD) δ=170.86, 138.87, 136.78, 132.19, 132.13, 125.21, 123.43, 55.71, 54.77, 36.86, 20.72 ppm; MS (ESI): calcd for $C_1H_{16}N_2O_2S$: 241.32 [M+H]$^+$; found: 241.61.

Synthesis of L-6-Chloro-Tryptophan

This compound was synthesized according to the synthetic scheme described in FIG. 6. To the solution 6-chloroindole (500 mg, 3.31 mmol, 1 eq) in acetic acid (10 mL) L-serine (695 mg, 6.62 mmol, 2 eq) and acetic anhydride (3.1 mL, 33.1 mmol, 10 eq) were added and the mixture was stirred under Ar at 73° C. for 4 h. The reaction mixture was concentrated to half of the volume, diluted with water and extracted with EtOAc. The organic layers were combined, dried over sodium sulfate and evaporated to yield crude product N$^\alpha$-acetyl-6-chloro-D,L-tryptophan (686 mg, 74% yield). $^1$H NMR (500 MHz, CD$_3$OD) δ1.91 (s, 3H), 3.15-3.31 (m, 2H), 4.67 (t, 1H), 6.97 (dd, 1H), 7.10 (s, 1H), 7.33

(d, 1H), 7.53 (d, 1H). The N$^\alpha$-acetyl-6-chloro-D,L-tryptophan (686 mg, 2.45 mmol) was dissolved in phosphate buffer (50 mL) containing 1 mM CoCl$_2$.6H$_2$O and pH 8.0. To the reaction mixture acylase I was added (500 mg) and the reaction was stirred at 37° C. for 24 h with occasional adjustment of pH to 8.0 with LiOH. The reaction mixture was heated to 60° C. for 5 mM, cooled to room temperature and filtered through celite. The filtrate was acidified to pH around 3 using HCl and extracted with EtOAc. The aqueous layer was lyophilized and used as crude product for the next reaction. Estimated yield of 43% (based on theoretical yield for the L-enantiomer), 125.4 mg. 6-chloro-L-tryptophan (125.4 mg, 0.527 mmol, 1 eq) was dissolved in a water/acetone mixture (1:1, v/v) to which NaHCO$_3$ (88.5 mg, 1.05 mmol, 2 eq) was added. Fmoc-OSu (195.6 mg, 0.58 mmol, 1.1 eq) was dissolved in acetone and added to the reaction mixture portion wise over the course of 3 h. Following reaction completion the acetone was evaporated and the aqueous layer acidified with acetic acid to pH about 3 followed by EtOAc extraction. The organic layers were combined, dried over sodium sulfate and evaporated. The crude product was purified with flash column chromatography and solvent system hexanes:EtOAc:AcOH (10:9:1) to yield pure Fmoc-6-chloro-L-tryptophan (237 mg, 98%). $^1$H NMR (500 MHz, CD$_3$OD), δ3.16-3.32 (m, 2H), 4.65 (t, 1H), 6.98 (dd, 1H), 7.12 (s, 1H), 7.3-7.55 (m, 8H), 7.79 (d, 2H). MS (ESI) calculated for C$_{26}$H$_{21}$ClN$_2$O$_4$ [M+H]$^+$: m/z 460.12, found 460.4.

6.3 Example 3. Synthesis of Macrocycle-Forming Linker Reagents

This Example demonstrates the synthesis of various macrocycle-forming linker reagents that can be useful for preparing macrocyclic peptidomimetics according to the methods presented herein. In particular, this example demonstrates of the synthesis of oxyamino/amino-thiol functionalized macrocycle-forming linker reagents such as those presented in FIG. 8, which can be useful for preparing macrocyclic peptidomimetics according to the representative methods described in FIGS. 3 and 4.

Synthesis of SP4, SP5, SP6 and SP7

These compounds were prepared according to the scheme presented in FIG. 7 and as described in (Frost, Vitali et al. 2013).

Synthesis of SP8 and SP9

Starting with 1 (FIG. 5C), this compound was hydrolyzed to the corresponding free carboxylic acid derivative (=3-((tert-butoxycarbonyl)amino)-4-((tritylthio)methyl)benzoic acid). 0.677 g of this intermediate (1.31 mmol) was dissolved in dichloromethane (15 mL) and the solution was added with tert-butyl-3-aminopropoxycarbamate (0.25 g, 1.31 mmol), HBTU (0.745 g, 1.96 mmol), and DIPEA (0.55 mL, 3.15 mmol) under argon. After extraction and purification by flash chromatography, tert-butyl(5-((3-(((tert-butoxycarbonyl)amino)oxy)propyl)carbamoyl)-2-((tritylthio)methyl)-phenyl)carbamate was isolated (0.658 g, 72%). $^1$H NMR (400 MHz, CDCl$_3$): δ 1.45 (s, 9H), 1.52 (s, 9H), 1.85-1.90 (m, 2H), 3.18 (s, 2H), 3.56-3.61 (m, 2H), 3.98 (t, 2H, J=5.6), 7.14 (d, 1H, J=8.0), 7.22-7.26 (m, 3H), 7.30-7.34 (m, 6H), 7.48-7.52 (m, 7H), 8.18 (s, 1H). This intermediate (0.48 g, 0.69 mmol) was dissolved in dicholoromethane (7.5 mL) under argon at 0° C. Triisopropylsilane (0.36 mL, 1.75 mmol) was added, followed by TFA (1.6 mL, dropwise). The reaction was stirred for 30 minutes at 0° C. Volatiles were then removed in vacuo and the yellow residue placed under high vacuum over night. The product was triturated with ice-cold hexanes and dried in vacuo to yield SP8 as a solid (0.18 g, quant.). $^1$H NMR (500 MHz, d$_4$-MeOD): δ 1.95-2.01 (m, 2H), 3.48 (t, J=6.8, 2H), 3.72 (s, 2H), 4.11 (t, 2H, J=6.0), 7.09 (d, J=8.0, 1H), 7.13 (d, J=8.0, 1H), 7.23 (s, 1H). $^{13}$C NMR (125 MHz, d$_4$-MeOD): δ 29.14, 37.34, 40.14, 74.16, 116.3, 116.6, 117.8, 126.5, 132.7, 135.9, 170.5. MS (ESI) calcd for C$_{11}$H$_{17}$N$_3$O$_2$S [M+H]$^+$m/z: 256.34; found: 255.92.

6.4 Example 4. Chemobiosynthetic Synthesis of p53 Macrocyclic Peptidomimetics This Example demonstrates the preparation of macrocyclic peptidomimetics of the present disclosure according to the representative method (embodiment) illustrated in FIG. 4.

Synthesis of Biosynthetic Precursors in *E. coli*

Briefly, protein precursors containing the target peptide sequence (GTSFA(pAcF)YWNLLA) (SEQ ID NO. 38) and (G(pAcF)SFAEYWNLLA) (SEQ ID NO. 39) followed by Mxe GyrA(N198A) intein and a C-terminal His tag were prepared as follows. First, genes that encode for these peptide sequences (an amber stop codon, TAG, is used for incorporation of pAcF) fused to the GyrA gene were generated by PCR using the pET22b-based plasmid pMG-G8T (Frost, Vitali et al. 2013) as template, forward primers PMI_for1 5'-GCGATTGGAACCTGCTGGCGTGCAT-CACGG-GAGATGCACTAGT-3' (SEQ ID NO. 40) and PMI_for2 5'-CTAGACATAT-GGGCTAGAGCTTCGCG-GAATATTGGAACCTGCTGGCGTGCAT-3' (SEQ ID NO. 41), and the reverse primer T7_terminator 5'-GCTAGTTAT-TGCTCAGCGGTGGC-3' (SEQ ID NO. 42). The resulting PCR products (~0.75 Kbp) were cloned into pET22 plasmid (Novagen) using Nde I and Xho I restriction enzymes, to produce the plasmids pPMI-2-GyrA and pPMI-3-GyrA. In these constructs, the gene encoding for the biosynthetic precursor protein is under the control of an IPTG-inducible T7 promoter. The precursor proteins were expressed by co-transforming pPMI-2-GyrA (or pPMI-3-GyrA) and a pEVOL-based vector encoding for a reported Mj tRNA$_{CUA}$/aminoacyl-tRNA synthetase pair (Wang, Zhang et al. 2003) for amber stop codon suppression with para-acetylphenylalanine (pAcF), into BL21(DE3) *E. coli* cells. Protein expression was carried out as described (Frost, Vitali et al. 2013). After expression, the proteins were purified Ni-affinity chromatography as described above. The identity of the isolated protein was confirmed by MALDI-TOF and SDS-PAGE. MS analysis indicated complete cleavage of the initial methionine in the purified proteins.

Synthesis and Isolation of Macrocyclic Peptidomimetics

Compounds P3 through P5 (SEQ ID NO. 38), P6 (SEQ ID NO. 44), and P7 through P9 (SEQ ID NO. 39) of FIG. 10 were prepared by large scale macrocyclization reactions between precursor protein PMI-2-GyrA (or PMI-3-GyrA) and the appropriate synthetic precursor (SP6, SP8, or SP4). In a typical reaction, the protein (200 μM in potassium phosphate 50 mM, NaCl 150 mM buffer (pH 7.5)) was mixed with 10 mM synthetic precursor and 10 mM TCEP (total volume: 6 mL). After 30 hrs, the pH of the reaction mixture was adjusted to 8.5 and incubated with iodoacetamide (15 mM) for 1 hour to cap the free thiol group. The reaction was centrifuged at 4000×g for 2 minutes, after which the supernatant (a) was separated from the pellet. The pellet was resuspended in 20% acetonitrile/$H_2O$ by vortexing for several minutes to dissolve the Macrocycle product, then centrifuged at 4000×g for 2 minutes to provide supernatant (b). The supernatants (a and b) were combined and applied to a solid-phase extraction $C_{18}$ column pre-washed with 10 column volumes (CV) MeOH, 10 CV acetonitrile, and 10 CV water. The macrocyclic product was eluted using a gradient of acetonitrile in water from 10% to 80%. The eluted macrocyle was further purified by HPLC using a GraceSmart RP C18 column (250×4.6 mm, 5 μm) maintained at 25° C., a flow rate of 0.9 mL/min, a binary mobile phase system consisting of A: water+0.1% TFA and B: acetonitrile+0.1% TFA, and a linear gradient from 10% to 90% solvent B (12 min). The identity of the isolated macrocyle was confirmed by LC-MS and MS/MS. Masses for all macrocyclic products are listed in the table below.

| Macrocycle | Mass Calc. $[M + H]^+$ | Mass Obs. $[M + H]^+$ |
|---|---|---|
| P3 | 1718.5 | 1719.1 |
| P4 | 1708.9 | 1708.4 |
| P5 | 1637.9 | 1637.5 |
| P7 | 1746.4 | 1746.2 |
| P8 | 1736.9 | 1737.3 |
| P9 | 1608.8* | 1608.5* |

*denotes free thiol (no acetamide alkylation)

6.5 Example 5. Solid-Phase Synthesis of p53 Macrocyclic Peptidomimetics

This Example demonstrates the preparation of macrocyclic peptidomimetics of the present disclosure according to the representative method (embodiment) illustrated in FIG. 3.

Synthesis and Isolation of Macrocyclic Peptidomimetics

Macrocycles P12 (SEQ ID NO. 39 and P13 through P19 (SEQ ID NO. 12) of FIG. 10 were prepared by first assembling the corresponding acyclic precursor molecule by standard Fmoc solid-phase peptide synthesis on the safety-catch resin, followed by on-resin or in-solution cyclization in the presence of the corresponding macrocycle-forming linker reagent (i.e. SP8 or SP9, FIG. 8). Briefly, all amino acid couplings in the SPPS step were performed using 2 eq of Fmoc-protected amino acid, HBTU and HOBt (2 eq each) as coupling reagents and 0.4 M NMM/DMF for 1 h. All of the amino acid analogs (i.e., N-Fmoc-protected pAcF, mAcF, or 6Cl-Trp) were coupled using the same conditions as well. The removal of Fmoc group was performed using 20% piperidine/DMF for 20 min. All of the peptides were acetylated at the N-terminus using acetic anhydride and DIPEA. All of the steps were monitored using standard Kaiser protocol for detection of free amines. Following the formation of the linear precursor molecule, the sulfonamide linker was activated by treatment with excess (50 eq) of iodoacetonitrile overnight with gentle shaking. Upon wash the resin was subjected to treatment with either the appropriate macrocycle-forming linker reagent (i.e., SP8, SP9, or SP4)

alone or with addition of benzylmercaptan to facilitate the cleavage of the peptide from the solid support and subsequent S—N acyl transfer (THF, overnight). The reaction was performed in the presence of TCEP to prevent disulfide formation and was monitored by MALDI-TOF MS. After the completion of the cyclization reaction, the peptide was subjected to treatment with TFA (TFA:triisopropylsilane:water=95:2.5:2.5, v/v/v) to remove all of the protecting groups and precipitated in cold diethyl ether. The crude product was subsequently treated with iodoacetamide (1 h, 20% DMSO/water) to alkylate the remaining thiol group and purified using RP-HPLC and gradient of 5-95% of acetonitrile in water (with 0.1% TFA) over 30 min. The identity of the purified peptides was confirmed using MALDI-TOF MS (Table 5).

The synthesis of the fluorescein (FITC)-labeled peptides was performed in the same manner except that the N-terminal β-Ala was added at the N-terminus instead of the acetylation. Upon removal of the Fmoc protecting group from β-Ala, FITC was coupled using 2 eq excess and DIPEA in DMF. The peptides were further treated the same as described above. The identity of the purified peptides was confirmed using MALDI-TOF MS (Table 5).

TABLE 5

ESI-MS data for macrocyclic peptidomimetics and reference linear peptides.

| Name Compound | calc. $[M + H]^+$ | obs. $[M + Na]^+$ |
|---|---|---|
| P12 | 1776.80 | 1799.02 |
| P13 | 1719.78 | 1741.87 |
| P14 | 1719.78 | 1741.93 |
| P15 | 1710.73 | 1732.81 |
| P16 | 1710.73 | 1732.87 |
| P17 | 1697.74 | 1719.88 |
| P18 | 1697.74 | 1719.83 |
| P19 | 1620.71 | 1642.89 |
| P10 | 1443.67 | 1465.76 |
| P11 | 1434.63 | 1456.81 |
| P1 | 1847.89 | 1869.91 |
| FITC-β-Ala-P13 | 2139.85 | 2161.96 |
| FITC-β-Ala-P15 | 2130.81 | 2152.96 |
| FITC-β-Ala-P19 | 2040.79 | 2062.87 |
| FITC-β-Ala-P10 | 1863.74 | 1885.91 |
| FITC-β-Ala-P1 | 2267.97 | 2290.03 |

6.6 Example 6. In Vitro Inhibitory Activity

This Example demonstrates the functionality of the designer p53 macrocyclic peptidomimetic molecules described in Example 1 toward disrupting the protein interaction between p53 and HDM2 or HDMX.

The ability of compounds P1 (SEQ ID NO. 1), P2 (SEQ ID NO. 43), P3 through P5 (SEQ ID NO. 38), P6 (SEQ ID NO. 44), P7 through P9 (SEQ ID NO. 39), P10 and P11 (SEQ ID NO. 12), P12 (SEQ ID NO. 39), and P13 through P19 (SEQ ID NO. 12) (FIG. 10) to disrupt the p53:HDM2/X interaction was assessed using a surface plasmon resonance (SPR) inhibition assay. Briefly, biotin-conjugated $p53_{(15-20)}$ peptide was first immobilized on a streptavidin-coated biosensor chip and increasing concentrations of the inhibitors were added to a fixed concentration of HDM2 or HDMX. From the corresponding dose-response curves (FIGS. 12A-12B), half-maximal inhibitory concentrations ($IC_{50}$) were determined for the compounds as summarized in FIG. 10. Interestingly, these studies revealed that both P3 (SEQ ID NO. 38) and P4 (SEQ ID NO. 38) possess improved inhibitory activity as compared to the acyclic counterpart P2, exhibiting an approximately 2-fold lower IC$_{50}$ for HDMX (P4 (SEQ ID NO. 38)) or for both HMD2 and HDMX (P3) (SEQ ID NO. 38). In addition, the SP4-based macrocycle P5 (SEQ ID NO. 38) showed very weak inhibition (IC$_{50}$≈10 μM), thus showing the deleterious effect of a mismatch between the length of the synthetic linker and the target side-chain···C-terminus bridging distance as anticipated.

The i/i+10(CO)-linked macrocycles P7 (SEQ ID NO. 39) and P8 (SEQ ID NO. 39) exhibited significantly improved ability to disrupt p53 interaction with HMD2/X as compared to P3 (SEQ ID NO. 38) and P4 (SEQ ID NO. 38) (FIG. 10). A notable effect of the type of non-peptidic linker on the binding properties of the corresponding macrocycle was also apparent. Notably, the SP4-containing P9 (SEQ ID NO. 39) was found to possess negligible inhibitory activity against HDM2 or HDMX (IC$_{50}$>50 μM), confirming that cyclization via the 'mismatching' SP4 strongly disfavored adoption of the bioactive α-helical conformation by the embedded PMI-derived peptide sequence. In stark contrast, much higher inhibitory activity was observed in the presence of the 'distance-matching' SP6, leading to a compound with sub-micromolar IC$_{50}$ values for both protein homologues. Interestingly, the simple replacement of the triazole unit in P7 (SEQ ID NO. 39) with the alkyl chain in P8 (SEQ ID NO. 39) led to a significant further improvement of inhibitory activity (3- to 4-fold) against both HDM2 (IC$_{50}$: 110 vs. 475 nM) and HDMX (IC$_{50}$: 340 vs. 910 nM, FIG. 10). Intriguingly, the nature of the linker was found to have an effect also on the selectivity of the compounds against the two protein homologs. Indeed, while the unconstrained peptide P6 (SEQ ID NO. 44) has stronger preference for HDM2 over HDMX, the macrocyclic counterparts, and in particular P7 (SEQ ID NO. 39), behave more as dual, equipotent inhibitors (IC$_{50(HDMX)}$/IC$_{50(HDM2)}$=5.5 vs. 1.9).

Starting from the most promising macrocycle, P8 (SEQ ID NO. 39), further optimization of the HDM2/X inhibitory activity of this compound was achieved by further shortening and modification of the peptide sequence encompassed by the macrocycle (e.g. 2-fold lower IC$_{50}$ for P15 (SEQ ID NO. 12), FIG. 10). Macrocycles with alternative linkers (e.g. SP9 vs. SP8) as well as alternative amino acid analogs for side-chain tethering (e.g. mAcF vs pAcF) also resulted in potent inhibitors for HDM2 and HDMX (IC$_{50}$<200 nM), showing 5- to 10-fold higher affinity to these proteins as compared to the reference linear p53-derived peptide P1 (SEQ ID NO. 1). Overall, these results demonstrate the utility and versatility of the methods described herein toward developing potent inhibitors of a target α-helix mediated protein-protein interaction.

Cloning, Expression, and Purification of HMD2 and HMDX Proteins.

Genes encoding for the p53-binding domain of human HDM2 (residues 1-109) and human HDMX (residues 1-109) were cloned into a pET22 vector (Novagen). The template for PCR amplification of the HDM2 gene was plasmid pGEX-4T MDM2 WT (AddGene #16237). (Zhou, Liao et al. 2001). In the final plasmid constructs (pET22-HDM2-YFP-His and pET22-HDMX—YFP-His), the HDM2/X protein was C-terminally fused to Yellow Fluorescent Protein (YFP) containing a C-terminal His tag. Fusion to the YFP protein was found to improve the solubility and stability of the protein constructs. To isolate the HDM2-YFP and HDMX-YFP fusion proteins, pET22-HDMX-YFP-His and pET22-HDM2-YFP-His plasmids were each transformed into BL21(DE3) cells followed by plating and overnight growth in LB medium containing ampicillin (50 mg L$^{-1}$).

The overnight cultures were used to inoculate a 500 mL LB culture (ampicillin at 50 mg L$^{-1}$), which was induced with 0.5 mM IPTG at OD$_{600}$~0.6, and incubated for 16 hours at 27° C. Cells were harvested by centrifugation and lysed by sonication. The clarified lysate was loaded onto a Ni-NTA affinity column and the protein was eluted with 50 mM Tris, 150 mM NaCl, 300 mM imidazole (pH 7.4). After buffer exchange with potassium phosphate 50 mM, NaCl 150 mM buffer (pH 7.5), aliquots of the protein solutions were stored at −80° C. Protein concentration was determined using the extinction coefficient at 280 nm ($\varepsilon_{280}$) calculated based on the protein primary sequence. The identity of the isolated protein was confirmed by MALDI-TOF and SDS-PAGE.

Inhibition Assays.

The surface plasmon resonance (SPR)-based inhibition assays were performed using a BIAcore T100 instrument. A HDM2/X binding surface was first generated by immobilizing ~500 RU of a biotinylated p53 peptide (biotin-SGSG-p53$_{15-29}$) on a streptavidin-coated biosensor chip (SA chip, GE Healthcare). Running buffer and sample buffer contained 10 mM HEPES buffer, pH 7.4 with 150 mM NaCl, 3 mM EDTA and 0.05% v/v Tween 20. For the inhibition studies, increasing concentrations of inhibitor were added to a fixed concentration (150 nM) of purified HDM2-YFP or HDMX-YFP and the mixture was injected over the functionalized surface. With increasing concentrations of the inhibitor, binding of HDM2 (or HDMX) to the surface is inhibited, leading to a decrease in biosensor response. HDM2/HDMX plus inhibitor samples were injected at a rate of 30 uL/min over a 2 minute interval by a 2 minute dissociation period and a 10-second regeneration step using 10 mM HCl. Specific binding curves for each concentration of inhibitor were obtained by subtracting the response in the reference surface from the response in the p53-coated surface. The data was analyzed with SigmaPlot 12.5 software and the sigmodial plots fitted to the Hill equation for a one site competitive binding to derive IC$_{50}$ values.

6.7 Example 7. HDM2 Binding Studies

HDM2 binding studies. The equilibrium dissociation constants (K$_D$) for selected macrocycles (e.g. P8 (SEQ ID NO. 39)) and the reference linear p53$_{(15-29)}$ peptide (P1) (SEQ ID NO. 1) toward direct binding to HDM2 were determined using a fluorescence polarization assay. For these studies, fluorescently labeled derivatives of these compounds were prepared by attaching fluorescein to the N-terminus of the macrocycle or peptide via a beta-alanine linker (i.e. FITC-β-Ala-P8 (SEQ ID NO. 39); FITC-β-Ala-P1 (SEQ ID NO. 1)). In the assay, 25-200 nM of the fluorescein-labeled compound and HDM2 concentrations varying from 10 nM to 2 μM were tested. The experiments were performed at room temperature in black 96-well plates with a final volume of 75 μL in PBS buffer with addition of 1% DMSO. Fluorescence was detected at excitation/emission of 470/520 nm and change in fluorescence polarization was plotted against the varying protein concentration. These studies demonstrated that many of the macrocyclic peptidomimetics bind potently to HDM2. For example, P8 (SEQ ID NO. 39) was determined to bind to HMD2 with an estimated K$_D$ of 63 nM, which corresponds to an order of magnitude higher affinity as compared to the linear p53$_{(15-29)}$ peptide (K$_D$~550 nM).

6.8 Example 8. α-Helicity of Macrocyclic Peptidomimetics

To examine the impact of macrocyclization on the peptide conformational properties, circular dichroism (CD) analyses were performed on the representative macrocyclic compounds (P7 (SEQ ID NO. 39) and P8 (SEQ ID NO. 39)) as well as on the linear peptide P6 (SEQ ID NO. 44) as a control (FIG. 13A). Peptide P6 (SEQ ID NO. 44) was found to display minima at 222 nm and 208 nm, which is consistent with the presence of an α-helical conformation. The α-helical content of the peptide was estimated to be about 31%. Cyclization of this sequence with SP6 (P7 (SEQ ID NO. 39)) produced an increase in α-helicity (40%), whereas P8 (SEQ ID NO. 39) showed a slight reduction in the α-helical content of the embedded peptide sequence (21%). Altogether, these studies demonstrate the ability of the macrocyclic peptidomimetics to accommodate and, in certain instances, to stabilize an α-helical motif. The lack of a strict correlation between α-helicity and in vitro inhibitory activity is not surprising as additional factors can affect the binding properties of HDM2/X binding molecules (Bernal, Wade et al. 2010; Muppidi, Wang et al. 2011), including potential interactions of the linker moiety with the protein surface (Brown, Quah et al. 2013).

Circular Dichroism Studies.

CD spectra were recorded with a JASCO J-710 CD spectropolarimeter using a 0.1 cm path length cuvette at room temperature. The purified peptides were dissolved in 5 mM potassium phosphate buffer (pH 7.0) containing 40% trifluoroethanol to a final concentration of 20-50 μM. Spectra were averaged over 2 scans recorded from 195 to 250 nm wavelength range with a speed of 10 nm/min, a response time of 1.0 s, and a resolution of 0.5 nm. The bandwidth was set to 2.0 nm and the sensitivity of the spectrometer set to 100 mdeg. The mean residue ellipticity was plotted vs. wavelength and the helical content of each peptide derived based on the following formula: $[\theta]_{222}/[40000\times(n-4)/n]$ where n=number of peptide bonds. (Johnson and Tinoco 1972)

6.9 Example 9. Proteolytic Stability of Macrocyclic Peptidomimetics

An envisioned potential benefit deriving from macrocyclization of peptide-based molecules according to the methods described herein is an enhancement in proteolytic stability. Despite its high potency in vitro, the linear peptide PMI was indeed found to be ineffective in cell-based assays in part due to rapid proteolysis (Pazgier, Liu et al. 2009). To assess the proteolytic stability of the p53 macrocyclic peptidomimetics, representative macrocycles P7 (SEQ ID NO. 39) and P8 (SEQ ID NO. 39), along with the reference linear peptide P6 (SEQ ID NO. 44), were incubated in the presence of chymotrypsin (FIG. 13B). P6 (SEQ ID NO. 44) was found to undergo rapid proteolytic degradation, with the original peptide becoming undetectable after only 30 minutes. In contrast, the macrocyclic peptides P7 (SEQ ID NO. 39) nd P8 (SEQ ID NO. 39) survived up to 3 and 4 hour incubation with the protease, respectively, exhibiting a 10- to 15-fold longer half-life compared to the acyclic counterpart. These data clearly showed the beneficial effect of the intramolecular linkage in imparting these compounds with increased resistance against proteolysis. It was also interesting to note how the SP6-based linker provided better performance in term of both α-helix stabilization and proteolytic resistance as compared to the SP8-based linker, which may be linked to the reduced conformational flexibility of the former over the latter.

Analysis of Proteolytic Resistance.

Each peptide (10 μM) was dissolved in 50 mM potassium phosphate buffer (pH 7.5) containing 150 mM NaCl and 10% DMSO. Chymotrypsin (Sigma-Aldrich) was added to a final concentration of 1.0 μg/mL and incubated at room temperature. At each time point, a 50 μL aliquot of the mixture was removed, quenched by TFA addition (5 μL) followed by HPLC analysis. Peptide cleavage was monitored based on the decrease of the peak area corresponding to the integer peptide. Experiments were performed at least in duplicate. HPLC analyses were carried out using a GraceSmart RP C18 column (250×4.6 mm, 5 μm) maintained at 25° C., a flow rate of 0.9 mL/min, a binary mobile phase system consisting of A: water+0.1% TFA and B: acetonitrile+0.1% TFA, and a linear gradient from 10% to 90% solvent B in 12 min.

6.10 Example 10. Cell Penetration Properties of Macrocyclic Peptidomimetics

Another envisioned potential benefit deriving from macrocyclization of peptide-based molecules according to the methods described herein is an enhancement in cell penetration. To examine this aspect, a representative p53 macrocyclic peptidomimetic (fluorescein-conjugated P8 (SEQ ID NO. 39)) and the control fluorescein-conjugated linear peptide P10 (SEQ ID NO. 12) were incubated with human cells (HEK-293), followed by analysis with confocal fluorescent miscroscopy. As illustrated by the images presented in FIGS. 14A-14B, the linear peptide showed no detectable levels of cellular uptake. In stark contrast, cells treated with the macrocyclic compound P8 (SEQ ID NO. 39) showed diffuse fluorescence at the intracellular level, thereby demonstrating the ability of the macrocyclic peptidomimetic molecule to efficiently penetrate the cells. Similar results were obtained for other p53 macrocyclic peptidomimetic molecules described in FIG. 10.

Cell Permeability Assays.

The cell permeability properties of the macrocyclic peptidomimetics and reference linear peptides were assessed using HEK-293 cell line. These cells were cultured in the DMEM medium supplemented with 10% fetal bovine serum and penicillin/streptomycin. For the cell permeability evaluations, cells were seated overnight (1×104 cells/well) in 24-well tissue culture treated plates with glass bottom. Following a PBS wash, reduced serum media (DMEM-RS) containing 20 μM concentration of fluorescein-conjugated P8 (SEQ ID NO. 39) or of the control fluorescein-conjugated linear peptide P10 (SEQ ID NO. 12) was added to the cells and incubated for 2 h. Prior to confocal imaging cells were washed with PBS, fixed with 2% paraformaldehyde in PBS and stained with nuclear stain DAPI.

6.11 Example 11. Anticancer Activity of Macrocyclic Peptidomimetics

To investigate the ability of the p53 macrocyclic peptidomimetic molecules to reduce the viability of human cancer cells, further activity studies were performed using SJSA-1 osteosarcoma cells, which exhibit a misregulation of the p53/HDM2/HDMX pathway due to abnormal overexpression of HMD2. As illustrated by the viability curves presented in FIG. 15, the viability of SJSA-1 cells showed no detectable reduction upon treatment with the reference linear peptide P10 (SEQ ID NO. 12). In contrast, a reduction of cell viability was obtained upon treatment of these cells with the p53 macrocyclic peptidomimetic P8 (SEQ ID NO. 39), thereby demonstrating the ability of this compound to kills cancer cells through reactivation of the p53-dependent apoptotic pathway. Similar results were obtained for other p53 macrocyclic peptidomimetic molecules described in FIG. 10, resulting in $LD_{50}$ in the low micromolar range. The responsiveness of the cells to p53-HDM2 inhibition was confirmed in parallel experiments with nutlin-3, a known potent and cell-permeable small-molecule inhibitor of HDM2.

Cell Viability Assay.

Cultured SJSA-1 cells were maintained in the RPMI-1640 medium supplemented with 10% fetal bovine serum. For viability evaluation cells were seated in 96-well, tissue culture treated plates (2×104 cells/well) and incubated overnight. Following a PBS wash, was added followed by varying concentrations of nutlin-3, of the macrocyclic peptidomimetic compounds, or one of the reference linear peptide(s). The cells were treated overnight and the viability was assessed by a standard MTT (3-(4,5-dimethylthiazol-2-yl)-2,5-diphenyltetrazolium bromide) assay. The viability is expressed as percentage of viability of the non-treated cells.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

While embodiments of the present disclosure have been particularly shown and described with reference to certain examples and features, it will be understood by one skilled in the art that various changes in detail may be effected therein without departing from the spirit and scope of the present disclosure as defined by claims that can be supported by the written description and drawings. Further, where exemplary embodiments are described with reference to a certain number of elements it will be understood that the exemplary embodiments can be practiced utilizing either less than or more than the certain number of elements.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

REFERENCES

Bernal, F., M. Wade, et al. (2010). *Cancer Cell* 18(5): 411-422.
Blackwell, H. E. and R. H. Grubbs (1998). *Angew. Chem. Int. Ed.* 37(23): 3281-3284.
Brown, C. J., S. T. Quah, et al. (2013). *ACS Chem. Biol.* 8(3): 506-512.
Brunel, F. M. and P. E. Dawson (2005). *Chem. Commun.* (20): 2552-2554.
Dias, R. L. A., R. Fasan, et al. (2006). *J. Am. Chem. Soc.* 128(8): 2726-2732.
Driggers, E. M., S. P. Hale, et al. (2008). *Nat Rev Drug Discov* 7(7): 608-624.
Fairlie, D. P., J. D. A. Tyndall, et al. (2000). *J. Med. Chem.* 43(7): 1271-1281.
Frost, J. R., F. Vitali, et al. (2013). *Chembiochem* 14(1): 147-160.
Henchey, L. K., A. L. Jochim, et al. (2008). *Curr. Opin. Chem. Biol.* 12(6): 692-697.
Henchey, L. K., J. R. Porter, et al. (2010). *Chembiochem* 11(15): 2104-2107.
Hu, B., D. M. Gilkes, et al. (2006). *J Biol Chem* 281(44): 33030-33035.
Jackson, D. Y., D. S. King, et al. (1991). *J. Am. Chem. Soc.* 113(24): 9391-9392.
Jo, H., N. Meinhardt, et al. (2012). *J. Am. Chem. Soc.* 134(42): 17704-17713.
Jochim, A. L. and P. S. Arora (2009). *Mol. Biosyst.* 5(9): 924-926.
Johnson, W. C., Jr. and I. Tinoco, Jr. (1972). *J. Am. Chem. Soc.* 94(12): 4389-4392.
Katsara, M., T. Tselios, et al. (2006). *Curr Med Chem* 13(19): 2221-2232.
Kawamoto, S. A., A. Coleska, et al. (2012). *J. Med. Chem.* 55(3): 1137-1146.
Kussie, P. H., S. Gorina, et al. (1996). *Science* 274(5289): 948-953.
Marine, J. C., M. A. Dyer, et al. (2007). *J. Cell. Sci.* 120(Pt 3): 371-378.
Marsault, E. and M. L. Peterson (2011). *Journal of Medicinal Chemistry* 54(7): 1961-2004.
Muppidi, A., Z. Wang, et al. (2011). *Chem. Commun.* 47(33): 9396-9398.
Obrecht, D., J. A. Robinson, et al. (2009). *Current Medicinal Chemistry* 16(1): 42-65.
Osapay, G. and J. W. Taylor (1992). *J. Am. Chem. Soc.* 114(18): 6966-6973.
Pazgier, M., M. Liu, et al. (2009). *Proc. Natl. Acad. Sci. USA* 106(12): 4665-4670.
Popowicz, G. M., A. Czarna, et al. (2008). *Cell Cycle* 7(15): 2441-2443.
Popowicz, G. M., A. Czarna, et al. (2007). *Cell Cycle* 6(19): 2386-2392.
Rezai, T., J. E. Bock, et al. (2006). *Journal of the American Chemical Society* 128(43): 14073-14080.
Rezai, T., B. Yu, et al. (2006). *Journal of the American Chemical Society* 128(8): 2510-2511.
Schafmeister, C. E., J. Po, et al. (2000). *J. Am. Chem. Soc.* 122(24): 5891-5892.
Scrima, M., A. Le Chevalier-Isaad, et al. (2010). *Eur. J. Org. Chem.* (3): 446-457.
Spokoyny, A. M., Y. Zou, et al. (2013). *J. Am. Chem. Soc.* 135(16): 5946-5949.
Tang, Y. Q., J. Yuan, et al. (1999). *Science* 286(5439): 498-502.
Wade, M., E. T. Wong, et al. (2006). *J. Biol. Chem.* 281(44): 33036-33044.
Wahl, G. M. and M. Wade (2009). *Mol. Cancer Res.* 7(1): 1-11.
Walensky, L. D., A. L. Kung, et al. (2004). *Science* 305 (5689): 1466-1470.
Wang, D., W. Liao, et al. (2005). *Angew Chem Int Ed Engl* 44(40): 6525-6529.
Wang, D., W. Liao, et al. (2005). *Angew. Chem. Int. Ed.* 44(40): 6525-6529.
Wang, L., Z. Zhang, et al. (2003). *Proc. Natl. Acad. Sci. USA* 100(1): 56-61.
Zhang, F. Z., O. Sadovski, et al. (2007). *J. Am. Chem. Soc.* 129(46): 14154-14155.
Zhou, B. P., Y. Liao, et al. (2001). *Nat Cell Biol* 3(11): 973-982.

What is claimed is:

1. A macrocyclic peptidomimetic molecule of Formula (I):

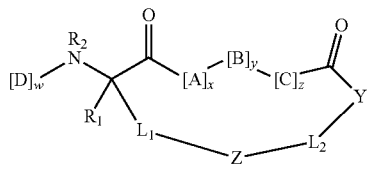

wherein:
each of A, C, and D is independently a natural or non-natural amino acid;
B is a natural amino acid, non-natural amino acid, an amino acid comprising at least one additional methylene groups between the amino and carboxyl group, an amino acid comprising an amino group which is a secondary or tertiary amine, an amino acid comprising a carboxy group replaced by an ester, [—NHN($R_3$)C(O)—], [—NH-$L_3$-CO—], [—NH-$L_3$-SO$_2$—], or [—NH-$L_3$-];
Y is —NH—, —N($R_4$)—, —NHN($R_4$)—, —NH—O—, —O—, or —S—;
Z is —SCH($R_6$)—, —CHR$_6$S—, —C≡C—, —N($R_5$)CO—, —CON($R_6$)—, —C($R_5$)=N($R_6$)—, —CH($R_5$)—NH($R_6$)—, —C($R_5$)=N—O—, —CH($R_5$)—NH—O—, —C($R_5$)=N—NH($R_6$)—, —CH($R_5$)—NH—NH($R_6$)—, or a triazole group;
$L_1$, $L_2$, and $L_3$ are independently aliphatic, aryl, substituted aliphatic, substituted aryl, heteroatom-containing aliphatic, heteroatom-containing aryl, substituted heteroatom-containing aliphatic, or substituted heteroatom-containing aryl groups, each being unsubstituted or substituted with $R_7$;
$R_1$, $R_2$, $R_3$, $R_4$, $R_5$, and $R_6$ are independently —H, an aliphatic, a substituted aliphatic, aryl, or a substituted aryl group;
each $R_7$ is independently —H, an aliphatic, a substituted aliphatic, an aryl, a substituted aryl group;
x is an integer from 0-10;
y is an integer from 0-10;
z is an integer from 0-10;
w is an integer from 1-1000;
x+y+z is at least 3; and
wherein the macrocyclic peptidomimetic molecule comprises an alpha-helix and is constrained by side-chain-to-C-end non-peptidic tethers, and wherein the macrocyclic peptidomimetic molecule does not have the formula:

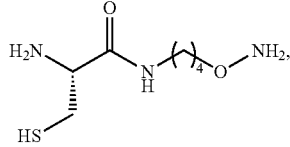

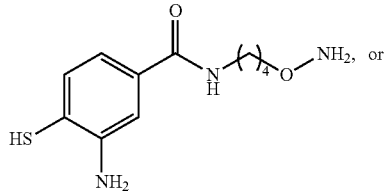

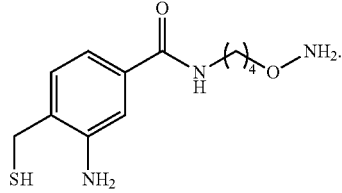

2. The macrocyclic peptidomimetic molecule of claim 1, wherein the macrocyclic peptidomimetic molecule has increased stability compared to a corresponding non-macrocyclic polypeptide, wherein the non-macrocyclic polypeptide lacks [Z-$L_2$-Y].

3. The macrocyclic peptidomimetic molecule of claim 1, wherein a secondary structure of the macrocyclic peptidomimetic molecule is more stable than a corresponding secondary structure of a corresponding non-macrocyclic polypeptide, wherein the non-macrocyclic polypeptide lacks [Z-$L_2$-Y].

4. The macrocyclic peptidomimetic molecule of claim 3, wherein the secondary structure of the macrocyclic peptidomimetic molecule corresponds to an alpha-helix.

5. The macrocyclic peptidomimetic molecule of claim 1, wherein the macrocyclic peptidomimetic molecule has increased proteolytic stability compared to a corresponding non-macrocyclic polypeptide, wherein the non-macrocyclic polypeptide lacks [Z-L$_2$-Y].

6. The macrocyclic peptidomimetic molecule of claim 1, wherein the macrocyclic peptidomimetic molecule has increased biological activity compared to a corresponding non-macrocyclic polypeptide, wherein the non-macrocyclic polypeptide lacks [Z-L$_2$-Y].

7. The macrocyclic peptidomimetic molecule of claim 1, wherein the macrocyclic peptidomimetic molecule has ability to penetrate living cells compared to a corresponding non-macrocyclic polypeptide, wherein the non-macrocyclic polypeptide lacks [Z-L$_2$-Y].

8. The macrocyclic peptidomimetic molecule of claim 1, wherein the alpha-helix comprises from one (1) turn to 5 turns.

9. The macrocyclic peptidomimetic molecule of claim 1, wherein [-L$_1$-Z-L$_2$-Y-] spans from one (1) turn to 5 turns of the alpha-helix.

10. The macrocyclic peptidomimetic molecule of claim 1, wherein the length of [-L$_1$-Z-L$_2$-Y-] is 4 Å to 12 Å per turn of the alpha-helix.

11. The macrocyclic peptidomimetic molecule of claim 1, wherein [-L$_1$-Z-L$_2$-Y-] spans one (1) turn of the alpha-helix.

12. The macrocyclic peptidomimetic molecule of claim 11, wherein the length of [-L$_1$-Z-L$_2$-Y-] is equal to the length of from 5 carbon-carbon bonds to 11 carbon-carbon bonds.

13. The macrocyclic peptidomimetic molecule of claim 11, wherein the macrocycle comprises a ring of 15 atoms to 21 atoms.

14. The macrocyclic peptidomimetic molecule of claim 1, wherein [-L$_1$-Z-L$_2$-Y-] spans two (2) turns of the alpha-helix.

15. The macrocyclic peptidomimetic molecule of claim 14, wherein the length of [-L$_1$-Z-L$_2$-Y-] is equal to the length of from 7 carbon-carbon bonds to 17 carbon-carbon bonds.

16. The macrocyclic peptidomimetic molecule of claim 14, wherein the macrocycle comprises a ring of 28 atoms to 38 atoms.

17. The macrocyclic peptidomimetic molecule of claim 1, wherein the macrocycle-forming linker [-L$_1$-Z-L$_2$-Y-] is selected from a group of macrocycle-forming linkers consisting of

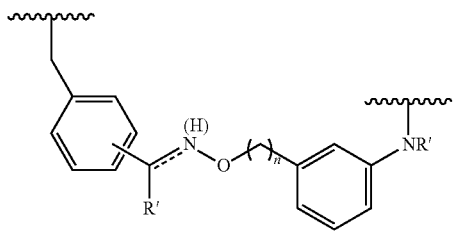

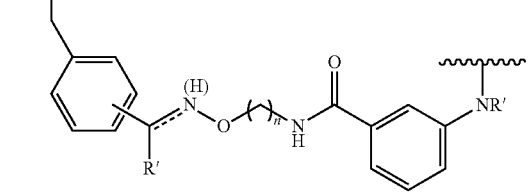

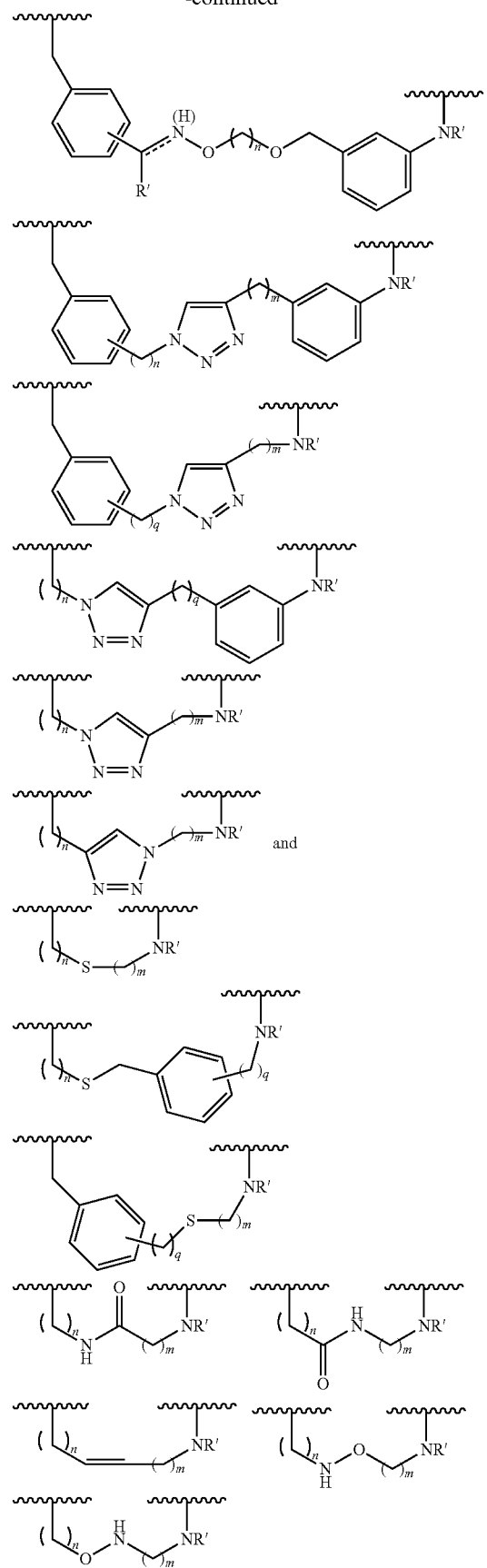

-continued

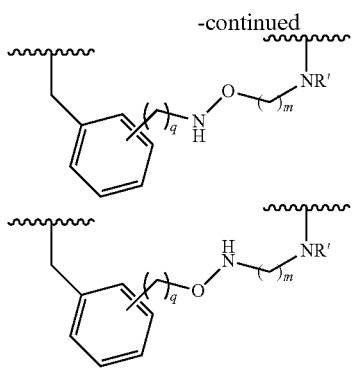

wherein
the symbol

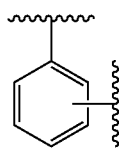

indicates an ortho-, meta- or para-disubstituted phenyl ring;
'm' and 'n' are each independently an integer number ranging from 1 to 10;
'q' is an integer number from 0 to 5; and
each R' is independently —H or —CH$_3$.

18. A method for synthesizing a macrocyclic peptidomimetic molecule, comprising contacting a precursor peptidomimetic molecule of Formula (IV):

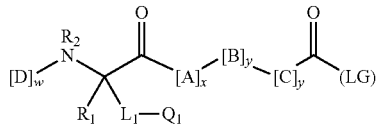

(IV)

with a compound of Formula (V):

$$Q_2\text{-}L_2\text{-}Y\text{—}H \quad (V)$$

wherein
each of A, C, and D is independently a natural or non-natural amino acid;
B is a natural amino acid, non-natural amino acid, an amino acid comprising at least one additional methylene groups between the amino and carboxyl group, an amino acid comprising an amino group which is a secondary or tertiary amine, an amino acid comprising a carboxy group replaced by an ester, [—NHN(R$_3$)C(O)—], [—NH-L$_3$-CO—], [—NH-L$_3$-SO$_2$—], or [—NH-L$_3$-];
Y is —NH—, —N(R$_4$)—, —NHN(R$_4$)—, —O—NH—, —O—, or —S—;
L$_1$, L$_2$, and L$_3$ are independently aliphatic, aryl, substituted aliphatic, substituted aryl, heteroatom-containing aliphatic, heteroatom-containing aryl, substituted heteroatom-containing aliphatic, substituted heteroatom-containing aryl groups, each being unsubstituted or substituted with R$_7$;

Q$_1$ is selected from a group consisting of sulphydryl (—SH), amino (—NHR$_5$), alkenyl (—C=CH$_2$), alkynyl (—C≡CH), azido (—N$_3$), keto (—C(O)R$_5$—), and carboxy (—C(O)OH) group;
Q$_2$ is selected from a group consisting of —CH(R$_6$)X, where X is F, Cl, Br, or I, amino (—NHR$_6$), oxyamino (—ONH$_2$), hydrazino (—NR$_6$NH$_2$), alkenyl (—C=CH$_2$), alkynyl (—C≡CH), azido (—N$_3$), keto (—C(O)R$_6$—), and carboxy (—COOH) group;
R$_1$, R$_2$, R$_3$, R$_4$, R$_5$, and R$_6$ are independently —H, aliphatic, substituted aliphatic, aryl, or substituted aryl group;
each R$_7$ is independently —H, an aliphatic, substituted aliphatic, an aryl, a substituted aryl group;
x is an integer from 0-10;
y is an integer from 0-10;
z is an integer from 0-10;
w is an integer from 1-1000;
x+y+z is at least 3; and
(LG) is a group that activates the terminal carboxylic acid carbonyl group toward nucleophilic substitution;
wherein the contacting results in a covalent linkage being formed between the side-chain group, L$_1$, and the C-terminal carboxyl group of the compound of Formula (IV) via a linker moiety, and
wherein the macrocyclic peptidomimetic molecule comprises an α-helix.

19. A macrocyclic peptidomimetic molecule for use in the treatment of a p53/HDM2/HDMX-related disease in a subject, this macrocyclic peptidomimetic molecule having the structure of Formula (VII):

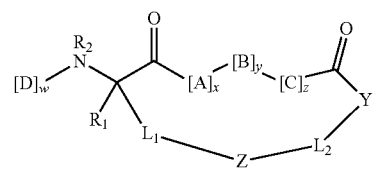

(VII)

wherein:
each A, C, and D is independently a natural or non-natural amino acid;
B is a natural amino acid, non-natural amino acid, an amino acid comprising at least one additional methylene groups between the amino and carboxyl group, an amino acid comprising an amino group which is a secondary or tertiary amine, an amino acid comprising a carboxy group replaced by an ester, [—NHN(R$_3$)C(O)—], [—NH-L$_3$-CO—], [—NH-L$_3$-SO$_2$—], or [—NH-L$_3$-];
Y is —NH—, —N(R$_4$)—, —NHN(R$_4$)—, —NH—O—, —O—, or —S—;
Z is —SCHR$_6$—, —CHR$_6$S—, —C=C—, —N(R$_5$)CO—, —CON(R$_6$)—, —C(R$_5$)=N(R$_6$)—, —CH(R$_5$)—NH(R$_6$)—, —C(R$_5$)=N—O—, —CH(R$_5$)—NH—O—, —C(R$_5$)=N—NH(R$_6$)—, —CH(R$_5$)—NH—NH(R$_6$)—, or a triazole group;
L$_1$, L$_2$, and L$_3$ are independently aliphatic, aryl, substituted aliphatic, substituted aryl, heteroatom-containing aliphatic, heteroatom-containing aryl, substituted heteroatom-containing aliphatic, substituted heteroatom-containing aryl groups, each being unsubstituted or substituted with R$_7$;

R₁, R₂, R₃, R₄, R₅, and R₆ are independently —H, aliphatic, substituted aliphatic, aryl, or substituted aryl group;

each R₇ is independently —H, an aliphatic, substituted aliphatic, an aryl, and a substituted aryl group;

x is an integer from 0-10;

y is an integer from 0-10;

z is an integer from 0-10;

w is an integer from 1-1000;

x+y+z is at least 3; and wherein the macrocyclic peptidomimetic molecule comprises an amino acid sequence which is at least 50% identical to an amino acid sequence selected from a group consisting of the amino acid sequences of SEQ ID NOS. 1 through 37.

20. The macrocyclic peptidomimetic molecule of claim 19, wherein the amino acid sequence comprised in the macrocyclic peptidomimetic molecule is an amino acid sequence selected from a group consisting of the amino acid sequences of SEQ ID NOS. 1 through 37.

21. The macrocyclic peptidomimetic molecule of claim 19, wherein the macrocyclic peptidomimetic molecule comprises a fluorescent label, an affinity label, a radioisotopic label, a targeting agent, or a therapeutic agent.

22. The macrocyclic peptidomimetic molecule of claim 19, wherein the macrocycle-forming linker [-L₁-Z-L₂-Y-] is selected from a group of macrocycle-forming linkers consisting of

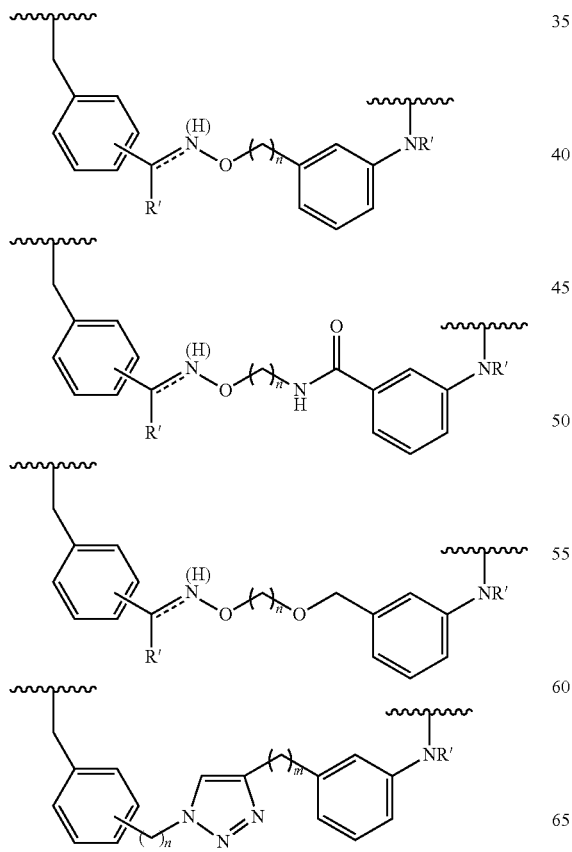

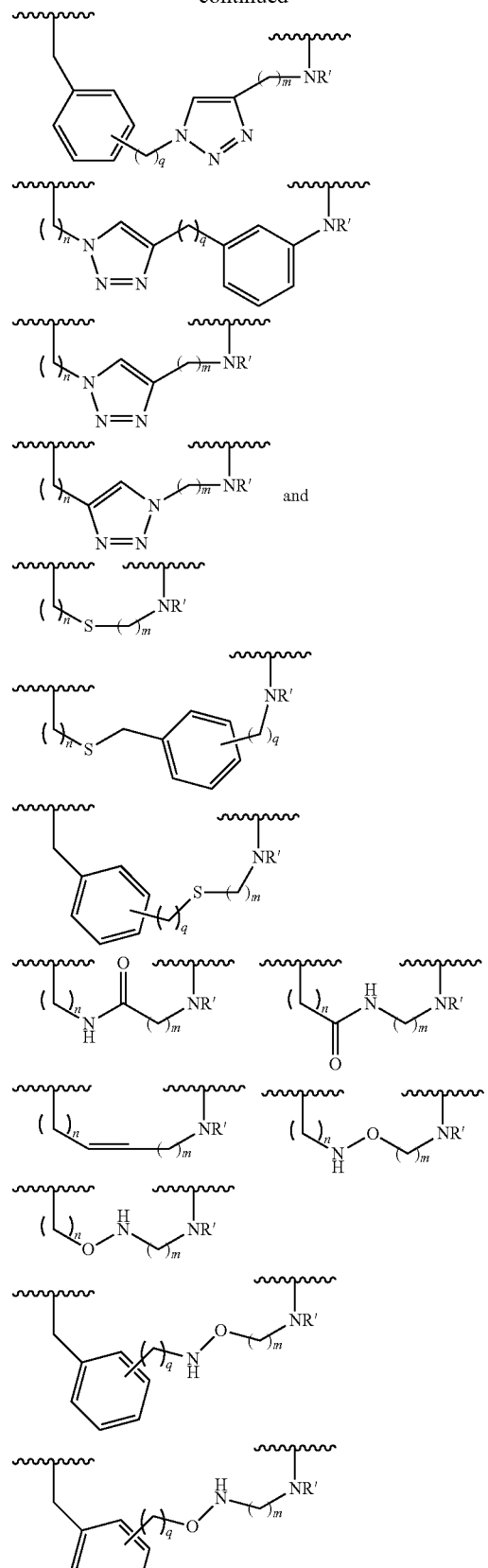

wherein
the symbol

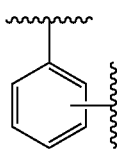

indicates an ortho-, meta- or para-disubstituted phenyl ring;

'm' and 'n' are each independently an integer number ranging from 1 to 10;

'q' is an integer number from 0 to 5; and each R' is independently —H or —CH₃.

23. The macrocyclic peptidomimetic molecule of claim 19, wherein the p53/HDM2/HDMX-related disease is a cancer or a neoplastic disease.

24. The macrocyclic peptidomimetic molecule of claim 19, wherein the p53/HDM2/HDMX-related disease is sarcoma, gastric cancer, esophageal cancer, rectal cancer, pancreatic cancer, ovarian cancer, prostate cancer, uterine cancer, skin cancer, brain cancer, carcinoma, cervical cancer, testicular cancer, lung cancer, bladder cancer, leukemia, or lymphoma.

25. The macrocyclic peptidomimetic molecule of claim 19, wherein the p53/HDM2/HDMX-related disease is an inflammatory, a neurodegenerative, or an autoimmune disease.

26. A method for treating a p53/HDM2/HDMX-related disease in a subject, comprising:
administering to a subject to be treated a macrocyclic peptidomimetic molecule having the structure of Formula (VII):

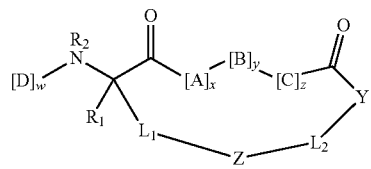

(VII)

wherein:
each A, C, and D is independently a natural or non-natural amino acid;
B is a natural amino acid, non-natural amino acid, an amino acid comprising at least one additional methylene groups between the amino and carboxyl group, an amino acid comprising an amino group which is a secondary or tertiary amine, an amino acid comprising a carboxy group replaced by an ester, [—NHN(R₃)C(O)—], [—NH-L₃-CO—], [—NH-L₃-SO₂—], or [—NH-L₃-];
Y is —NH—, —N(R₄)—, —NHN(R₄)—, —NH—O—, —O—, or —S—;
Z is —SCHR₆—, —CHR₆S—, —C≡C—, —N(R₅)CO—, —CON(R₆)—, —C(R₅)=N(R₆)—, —CH(R₅)—NH(R₆)—, —C(R₅)=N—O—, —CH(R₅)—NH—O—, —C(R₅)=N—NH(R₆)—, —CH(R₅)—NH—NH(R₆)—, or a triazole group;
L₁, L₂, and L₃ are independently aliphatic, aryl, substituted aliphatic, substituted aryl, heteroatom-containing aliphatic, heteroatom-containing aryl, substituted heteroatom-containing aliphatic, substituted heteroatom-containing aryl groups, each being unsubstituted or substituted with R₇;
R₁, R₂, R₃, R₄, R₅, and R₆ are independently —H, aliphatic, substituted aliphatic, aryl, or substituted aryl group;
each R₇ is independently —H, an aliphatic, substituted aliphatic, an aryl, and a substituted aryl group;
x is an integer from 0-10;
y is an integer from 0-10;
z is an integer from 0-10;
w is an integer from 1-1000;
x+y+z is at least 3; and
wherein the macrocyclic peptidomimetic molecule comprises an amino acid sequence which is at least 50% identical to an amino acid sequence selected from a group consisting of the amino acid sequences of SEQ ID NOS. 1 through 37.

27. The method of claim 26, wherein the amino acid sequence comprised in the macrocyclic peptidomimetic molecule is an amino acid sequence selected from a group consisting of the amino acid sequences of SEQ ID NOS. 1 through 37.

28. The method of claim 26, wherein the macrocyclic peptidomimetic molecule comprises a fluorescent label, an affinity label, a radioisotopic label, a targeting agent, or a therapeutic agent.

29. The method of claim 26, wherein the macrocycle-forming linker [-L₁-Z-L₂-Y-] is selected from a group of macrocycle-forming linkers consisting of

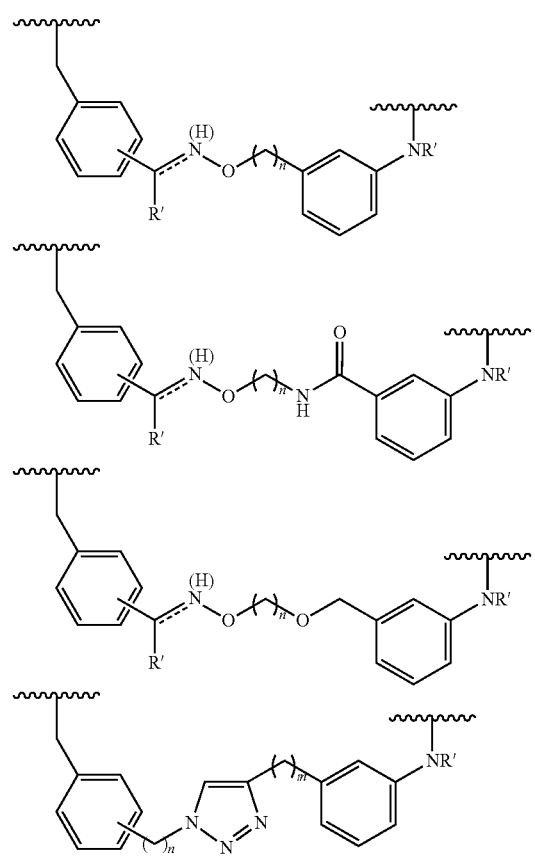

-continued

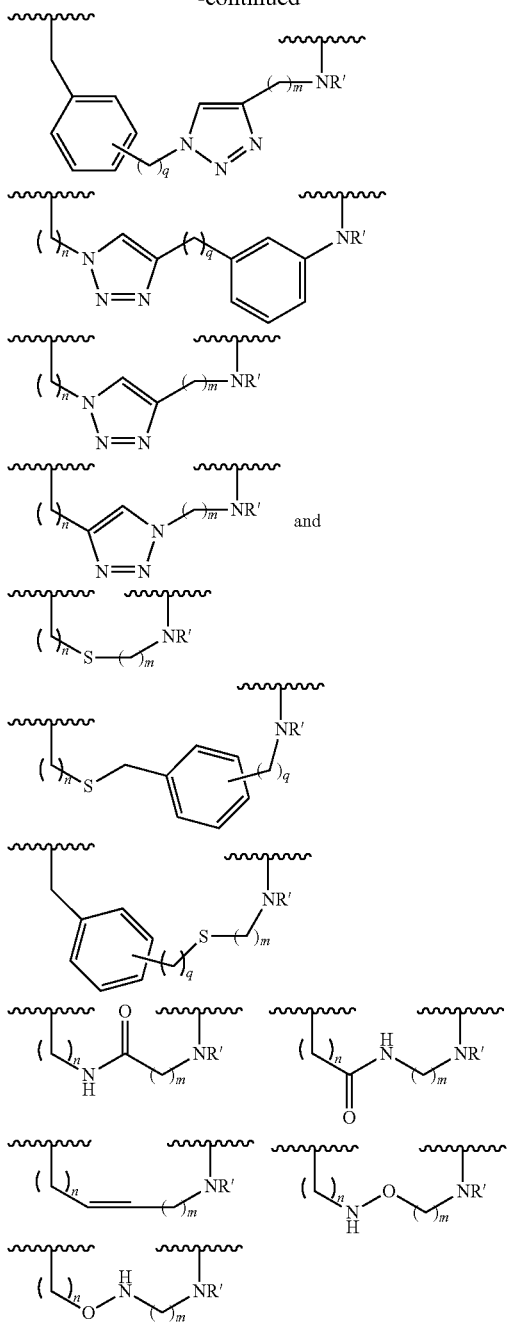

and

-continued

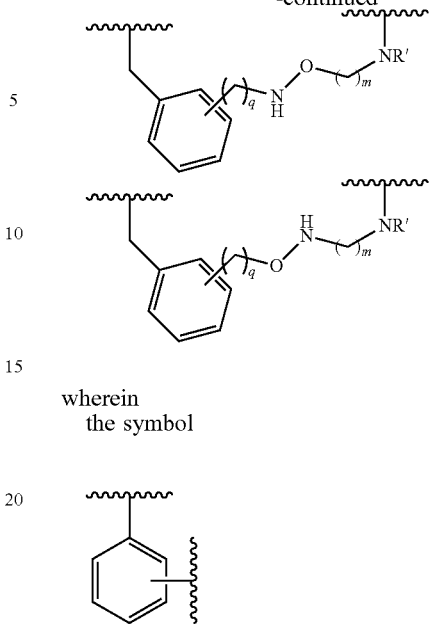

wherein
the symbol

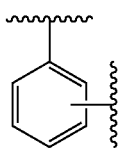

indicates an ortho-, meta- or para-disubstituted phenyl ring;
'm' and 'n' are each independently an integer number ranging from 1 to 10;
'q' is an integer number from 0 to 5; and
each R' is independently —H or —CH$_3$.

30. The method of claim 26, wherein the p53/HDM2/HDMX-related disease is a cancer or a neoplastic disease.

31. The method of claim 30, wherein the p53/HDM2/HDMX-related disease is sarcoma, gastric cancer, esophageal cancer, rectal cancer, pancreatic cancer, ovarian cancer, prostate cancer, uterine cancer, skin cancer, brain cancer, carcinoma, cervical cancer, testicular cancer, lung cancer, bladder cancer, leukemia, or lymphoma.

32. The method of claim 26, wherein the p53/HDM2/HDMX-related disease is an inflammatory, a neurodegenerative, or an autoimmune disease.

33. The macrocyclic peptidomimetic molecule of claim 19, wherein the amino acid sequence comprised in the p53 macrocyclic peptidomimetic molecule is at least 60% identical to the polypeptide sequences corresponding to SEQ ID NOS: 1 through 37.

34. The method of claim 26, wherein the amino acid sequence comprised in the p53 macrocyclic peptidomimetic molecule is at least about 60% identical to the polypeptide sequences corresponding to SEQ ID NOS: 1 through 37.

* * * * *

UNITED STATES PATENT AND TRADEMARK OFFICE
CERTIFICATE OF CORRECTION

PATENT NO. : 10,294,273 B2
APPLICATION NO. : 15/301084
DATED : May 21, 2019
INVENTOR(S) : Rudi Fasan Page 1 of 1

It is certified that error appears in the above-identified patent and that said Letters Patent is hereby corrected as shown below:

In the Claims

Column 119, Claim number 1, Line numbers 41-42, please delete "methylene groups" and replace with --methylene group--

Column 123, Claim number 18, Line numbers 53-54, please delete "methylene groups" and replace with --methylene group--

Column 123, Claim number 18, Figure IV, please delete "$[C]_y$" and replace with --$[C]_z$--

Column 124, Claim number 19, Line numbers 48-49, please delete "methylene groups" and replace with --methylene group--

Column 127, Claim number 26, Line numbers 51-52, please delete "methylene groups" and replace with --methylene group--

Signed and Sealed this
Twenty-seventh Day of August, 2019

Andrei Iancu
*Director of the United States Patent and Trademark Office*